United States Patent [19]
Tomich et al.

[11] Patent Number: 6,077,826
[45] Date of Patent: Jun. 20, 2000

[54] SYNTHETIC MACROMOLECULAR CHANNEL ASSEMBLY FOR TRANSPORT OF CHLORIDE IONS THROUGH EPITHELIUM USEFUL IN TREATING CYSTIC FIBROSIS

[75] Inventors: John M. Tomich; Takeo Iwamoto, both of Manhattan; Lawrence P. Sullivan, Shawnee, all of Kans.

[73] Assignee: Kansas State University Research Foundation, Manhattan, Kans.

[21] Appl. No.: 09/093,227

[22] Filed: Jun. 8, 1998

Related U.S. Application Data

[63] Continuation of application No. 08/789,155, Jan. 24, 1997, abandoned.

[51] Int. Cl.$^7$ .......................... C07K 14/00; A61K 38/16
[52] U.S. Cl. ........................... 514/12; 514/13; 530/324; 530/325; 530/326
[58] Field of Search ................ 514/12–13; 530/324–326

[56] References Cited

U.S. PATENT DOCUMENTS

| | | | |
|---|---|---|---|
| 5,045,531 | 9/1991 | Berkowitz et al. | 514/12 |
| 5,368,712 | 11/1994 | Tomich et al. | 204/403 |
| 5,543,399 | 8/1996 | Riordan et al. | 514/21 |

OTHER PUBLICATIONS

Reddy et al., J. Biol. Chem. vol. 268, No. 20 pp. 14608–14615, Jul. 1993.
Samsom, Prog. Bioph. Mol. Biol. vol. 55 pp. 139–235 and 217–222, Feb. 1991.
Montal et al., PNAS USA vol. 91 pp. 1495–1499, Feb. 1994.
Davidow et al. (AN 1390) and Devuyst et al. (AN 1167), J. Amer. Soc. Neph. vol. 6, No. 3 p. 693, Sep. 1995.
Spatola, Chemistry & Biochemistry of Amino acids and Peptides (Marcel Dekker) pp. 338–339, 1983.

*Primary Examiner*—Bennett Celsa
*Attorney, Agent, or Firm*—Hovey, Williams, Timmons & Collins

[57] ABSTRACT

The present invention is directed to multiple-peptide channel assemblies for transport of anions such as chloride ions through epithelial cells, synthetic peptides capable of forming such channel assemblies and methods for using channel assemblies in therapeutic contexts for altering the flux of water across epithelial cells. The channel assemblies are composed of a plurality of peptides that transport through the membrane of an epithelial cell and provide for alteration of the flux of water through the cell. The peptides are soluble in water to a level of at least 10 mM and exhibit at least about 50% helical content when dispersed in a 40% trifluoroethanol/60% water solution. The peptides ideally have the amino acid sequence $ABC(X)_n DEF$, where A, B, C, D, F and X are individual amino acid residues, n ranges from 12–24 and at least one of the amino acids selected from the group consisting of A, B, and C is a charged amino acid, and at least one of the amino acids selected from the group consisting of D, E, and F is a charged amino acid. The method hereof provides for altering flux of water from an epithelial cell and includes providing from 3–6 peptides capable of forming a channel assembly with each of such peptides having from about 18–30 amino acid residues therein, then contacting the peptides with a surface of an epithelial cell to cause the peptides to embed therein and alter the flux of water across the cell.

4 Claims, 21 Drawing Sheets

M2GlyR

NH2-Pro-Ala-<u>Arg</u>-Val-Gly-Leu-Gly-Ile-Thr-Thr-Val-Leu-Thr-Met-Thr-Thr-Gln-Ser-Ser-Gly-Ser-<u>Arg</u>-Ala-COOH

23 Amino Acids            MW = 2304

*Fig. 1*

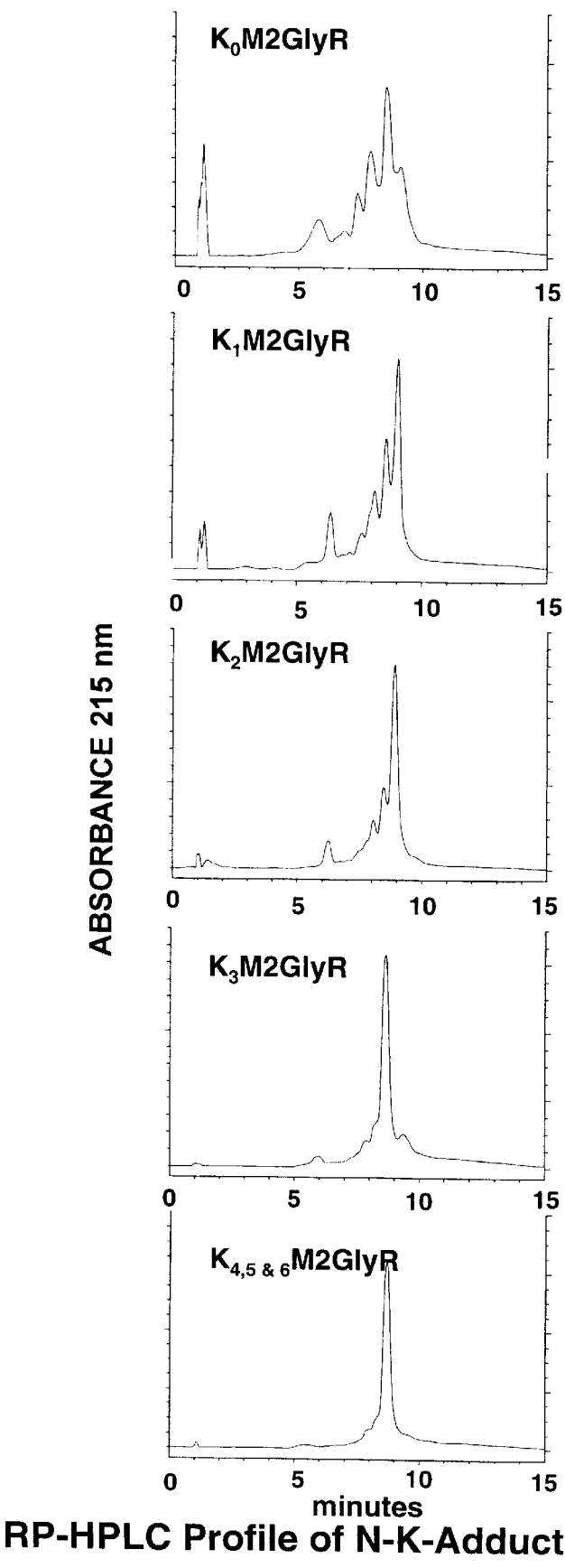
RP-HPLC Profile of N-K-Adducts of M2GlyR

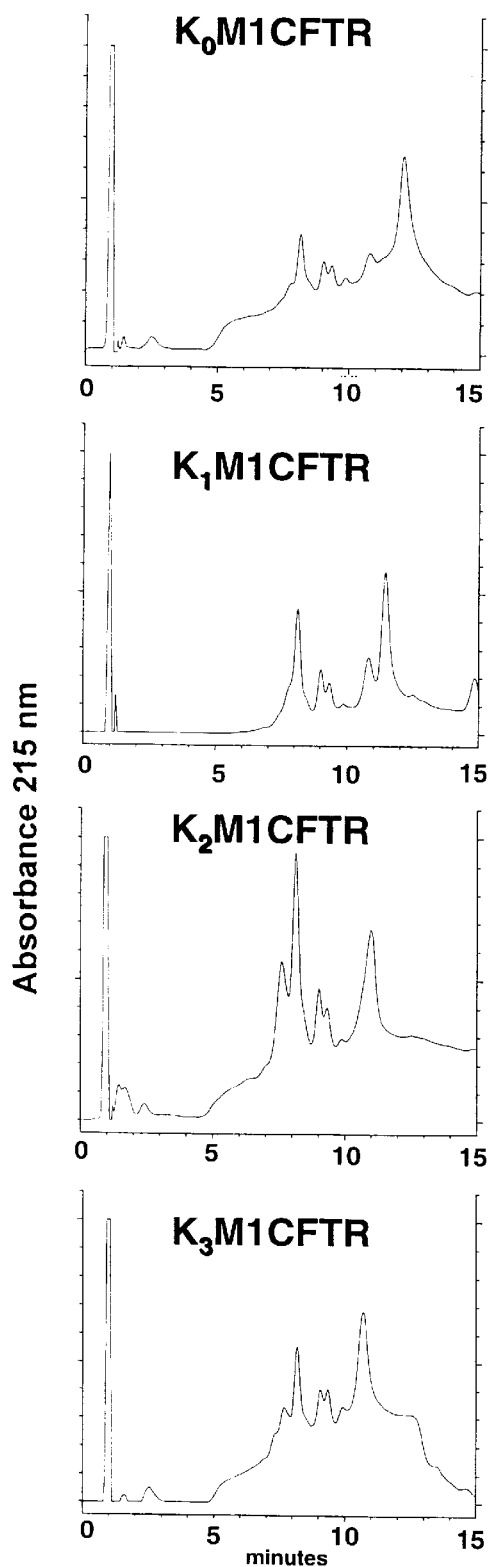
RP-HPLC Profile of N-K-Adducts of M1CFTR

RP-HPLC Profile of N-K-Adducts of M1CFTR

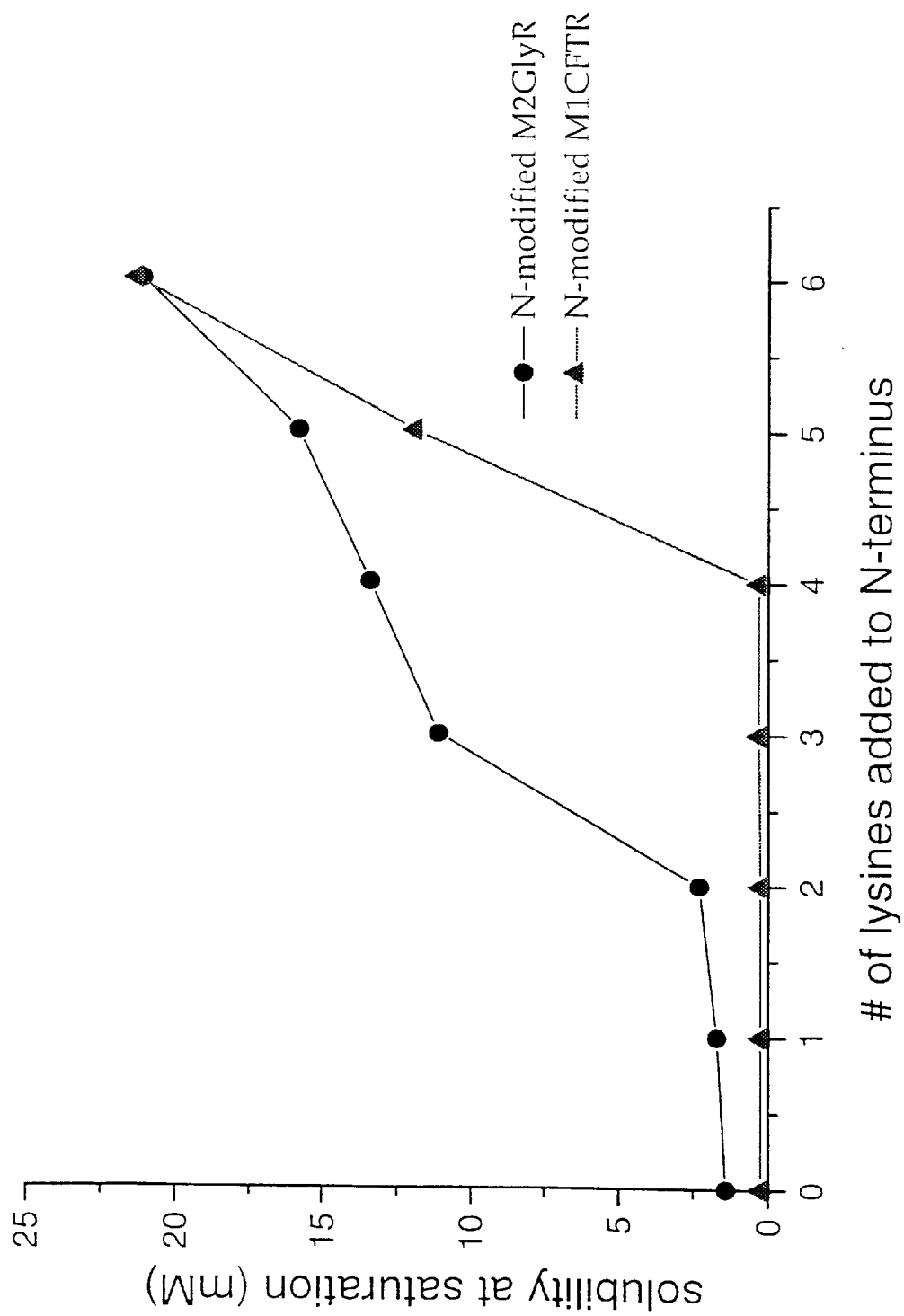

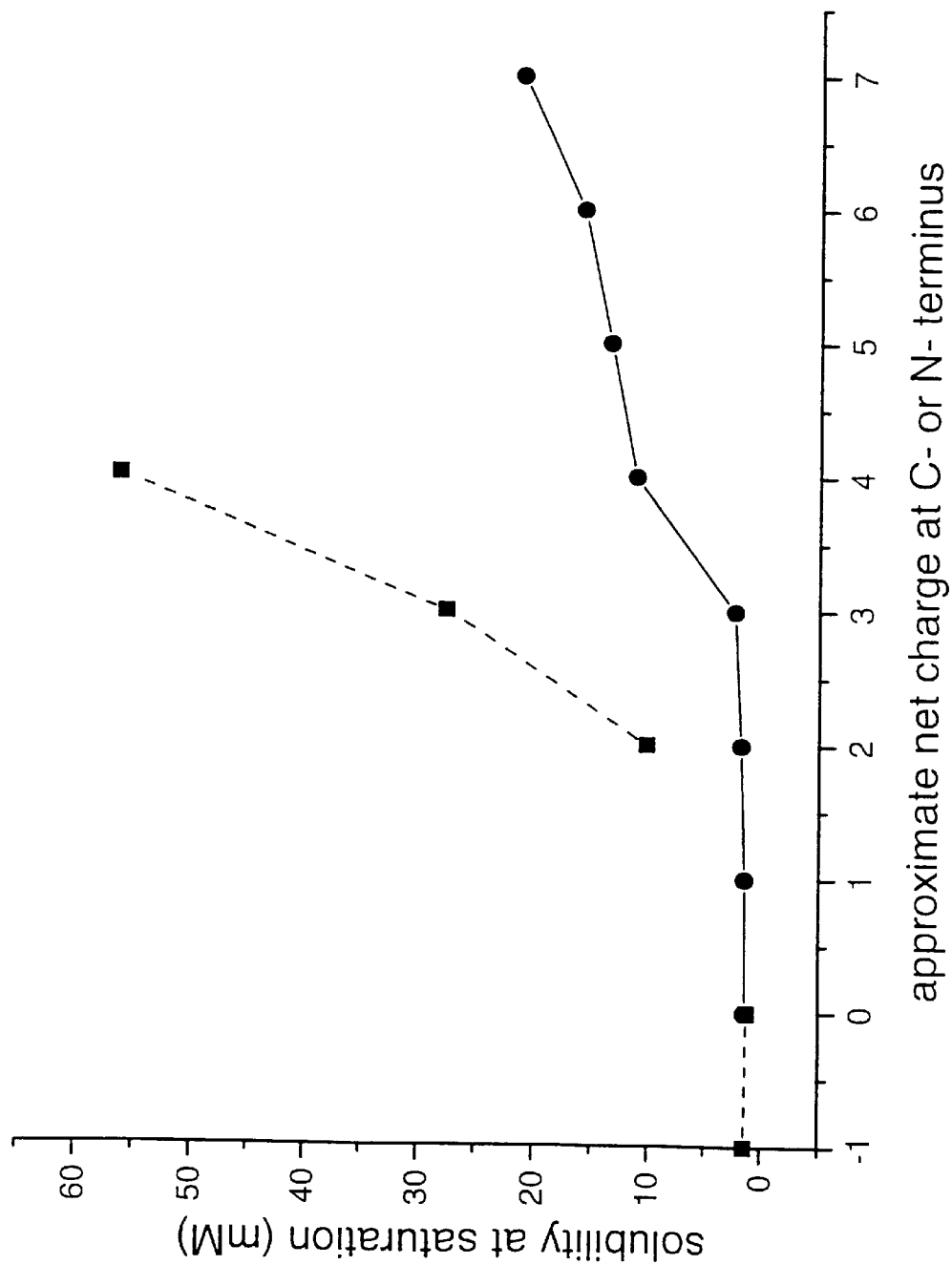

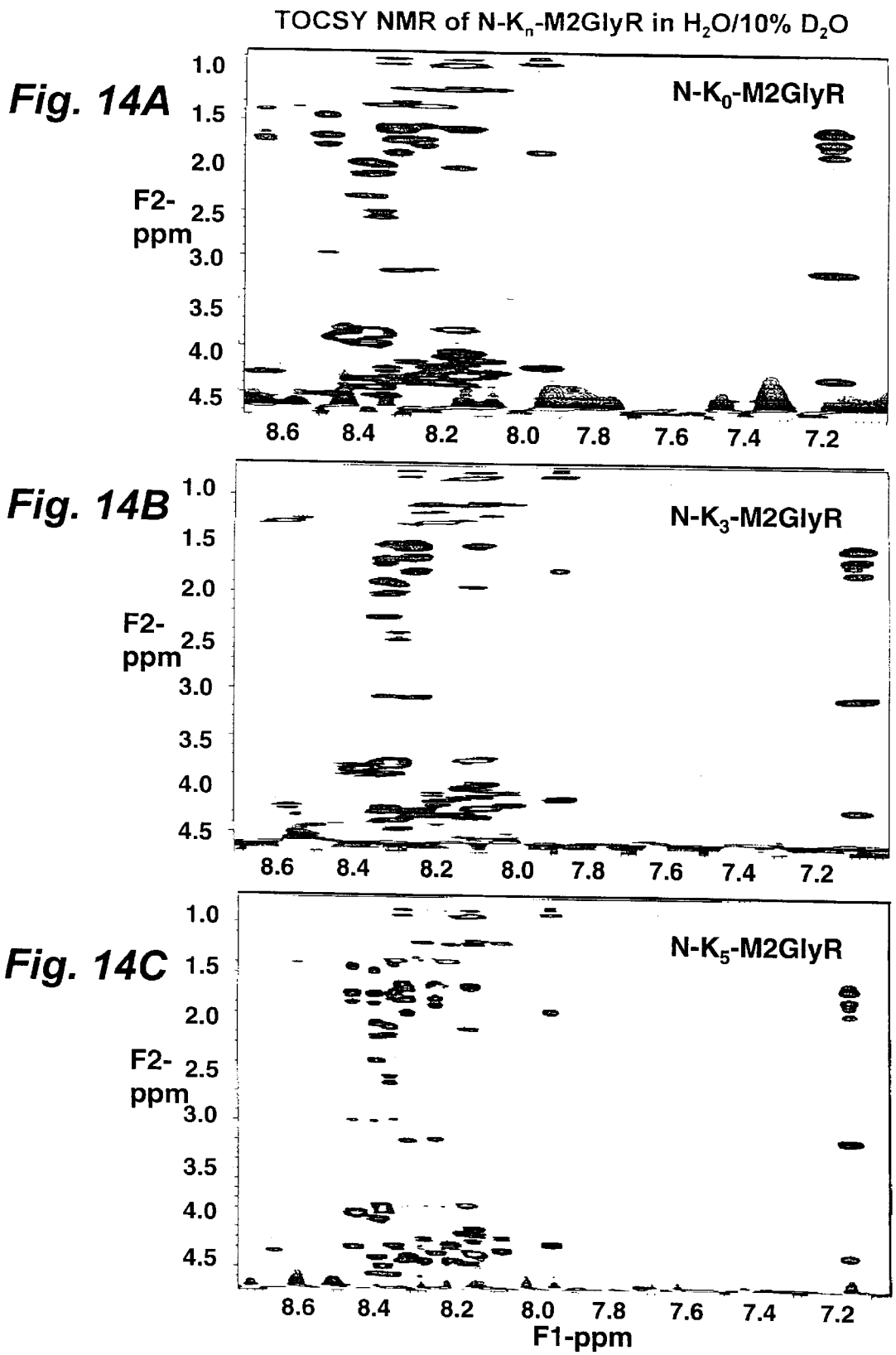

CONTROL

PEPTIDE-TREATED

6,077,826

SYNTHETIC MACROMOLECULAR CHANNEL ASSEMBLY FOR TRANSPORT OF CHLORIDE IONS THROUGH EPITHELIUM USEFUL IN TREATING CYSTIC FIBROSIS

This Application is a continuation application of Ser. No. 08/789,155, filed Jan. 24, 1997, now abandoned, MACROMOLECULAR CHANNEL ASSEMBLY FOR TRANSPORT OF CHLORIDE IONS THROUGH EPITHELIUM USEFUL IN THE TREATING CYSTIC FIBROSIS, the teachings of which are incorporated herein by reference.

FEDERALLY SPONSORED RESEARCH OR DEVELOPMENT

This invention was made with government support under Grants GM43617 and DK13476 awarded by the Department of Health and Human Services/National Institutes of Health. The government has certain rights in the invention.

SEQUENCE LISTING

A printed Sequence Listing accompanies this application, and has also been submitted with identical contents in the form of a computer-readable ASCII file on a floppy diskette.

BACKGROUND OF THE INVENTION

1. Field of the Invention

The present invention is broadly concerned with a multiple-peptide channel assembly which provides transport of anions through epithelial cell membranes wherein the preferred peptides have from about 18–30 amino acid residues and are soluble in water to a level of at least 10 mM; such channel assemblies can be used in the treatment of diseases such as cystic fibrosis (CF) and adult polycystic kidney disease (APKD). More particularly, the invention pertains to such channel assembly forming peptides, and corresponding methods of use, wherein the peptides are a segment of a native (i.e., naturally occurring) channel protein and have their water solubilities enhanced by modification of the C- or N-ends thereof modified with a plurality of polar amino acid residues such as lysine.

2. Description of Prior Art

Introduction. A major problem in CF is the inability of airway epithelia to secrete fluid. The resulting changes in the composition of the mucous coating the airway epithelia result in infection and subsequent inflammation, scarring, and eventual pulmonary destruction. The basis of the problem is the absence of functional cystic fibrosis transmembrane conductance regulator (CFTR) in the apical membrane of the epithelial cells. This leads to an increase in the absorption of salt and water and an inability to respond to appropriate stimuli by secreting chloride and water. CFTR is a chloride channel; in addition it down-regulates sodium channels and up-regulates another population of chloride channels, the outwardly rectifying chloride channel (ORCC) (1). These properties of CFTR enable the airway cells to secrete chloride and this drives the secretion of sodium and water.

Two groups reported that a synthetic-23-residue α-helical peptide forms anion-selective channels in phospholipid bilayers. The peptide has the amino acid sequence of the putative transmembrane segment M2 of the strychnine-binding a subunit of the inhibitory glycine receptor and is named M2GlyR (FIG. 1; Sequence ID No. 1) (2, 3).

The origin and properties of M2GlyR. The glycine receptor is a membrane protein present in post-synaptic membranes. Binding of glycine activates a $Cl^-$ conducting channel, leading to hyperpolarization of the membrane and inhibition of the synapse. The receptor consists of two major glyco-polypeptides, an αsubunit of 48 kd and a β subunit of 58 kd, and a receptor-associated cytoplasmic protein of 93 kd (4). Strychnine, an antagonist of the glycine receptor, binds only to the a subunit. Messenger RNA corresponding to this subunit leads to the expression of functional, glycine-activated, $Cl^-$ channels upon injection into *Xenopus oocytes* (5–7).

The glycine receptor channel in cultures of embryonic mouse spinal cord is selective for monovalent anions, with conductances of 27 and 46 pS in 145 mM $Cl^-$ solution (8,9). Pharmacological studies suggested the presence of two sequentially occupied anion binding sites in the channel. These sites are considered to be the functional correlates of the positively charged amino acids bordering the M2 segment of the a subunits (8). This finding led to the development of the synthetic peptide with the sequence of the M2 segment of the glycine receptor.

Electrical recordings from phospholipid bilayers containing M2GlyR showed single-channel conductances of 25 pS and 49 pS in symmetric 0.5 M KCl with channel open lifetimes in the millisecond range. Single channel events occurred in 0.5 M N-methyl-D-glucamine HCl but not in sodium gluconate, indicating that the channel is anion selective. A transference number for anions of 0.85 was calculated from reversal potential measurements under a 5-fold KCl concentration gradient (10).

After insertion into the lipid bilayers the monomeric peptides self-assemble to form conductive oligomers of different amplitudes. To gain control over the aggregate number, four identical M2GlyR peptide units were tethered to a 9-amino acid carrier template to form a four-helix bundle protein. This tetramer, incorporated into lipid bilayers, formed channels of uniform unitary conductance of 25 pS. The 49 pS conductance described above is presumed to be due to the presence of a pentamer (10).

The tetrameric channel was blocked by the $Cl^-$ channel blockers 9-anthracene carboxylic acid (9-AC) and niflumic acid (NFA). It was not blocked by QX-222, an analogue of lidocaine and a blocker of cation-selective channels. Strychnine, an antagonist of the glycine receptor, does not block the channel-forming tetramer. Strychnine is presumed to bind to the ligand-binding domain of the receptor exposed to the extracellular surface but not to the channel domain (10).

Structure of channel forming peptides. While great strides have been made in the area of channel function and regulation, using the intact protein or in some cases purified channel proteins reconstituted into model membranes, many aspects of channel function remain unresolved. A key element, an atomic coordinate three dimensional structure of any mammalian channel protein, is not yet available. These data sets are crucial for the unambiguous assignment of the contributions individual segments make to the overall geometry of the intact protein and would contribute greatly to the understanding of the dynamics involved in channel function. The lack of structural data is due in part to the large size of these molecules but more likely due to the difficulty encountered in crystallizing membrane proteins (11). Solution NMR structural data are lacking primarily due to the large size and hence slow tumbling of the proteins embedded in lipid micelles.

Structural data does exist for the related class of channel forming peptides (CFPs). These channels are much smaller in size and contain only a ring of short peptide chains organized around the central ion conducting pore in the lipid bilayer. These channels are unique in that they assemble by the oligomerization of a single peptide. These structures are models for studying the structure and function of the various regulated channels that occur in nature. This class of CFPs includes: the α-aminoisobutyric acid-containing channels such as alamethicin and zervamicin, and a number of toxins and venoms such as melittin, cecropins, mast cell degranulating peptides, and the defensins. Melittin is somewhat of a special case because it forms channels only at low concentrations; at higher concentrations it acts as a lytic agent (12). In some cases CFPs assemble spontaneously upon insertion into the bilayer while in the remaining cases the assembly requires an electrical potential across the membrane ($V_m$).

The structure of the channels arising from the assembly of these peptides vary from trimers to hexadecamers associated in the form of helical bundles or β-barrels. The most widely accepted model which is in accord with the model for channel proteins has the helices arranged with their dipoles all pointing in the same direction (parallel) (13,14). Since CFP channels, unlike authentic channel proteins, are not generated from the association of large protein subunits, alternative stabilization schemes must be invoked to account for the presence of this higher energy arrangement of parallel segments. These could include aligning the dipoles in response to the presence of the membrane potential and/or an increase in the favorable inter-molecular interactions promoted by the parallel assembly. Most CFPs form multiple size bundles of parallel segments (e.g., n=4, 5, 6) that can spontaneously increase or decrease in size upon the addition or deletion of a peptide monomer from the channel assembly. These Observations imply that enough information is contained in a single channel forming polypeptide to drive the correct folding, assembly, and activity of these channels.

The activity of these assembled molecules, the opening and closing of the channels on the millisecond time scale, has been ascribed to numerous effects. Three different helical motions have been implicated (15): the bending and twisting of the helices, rigid-body fluctuations of the entire assembled structure with the lipid bilayer, and rotational motions of the polypeptide around its helical axis. Another hypothesis suggests that channel activity is a consequence of a conformational change that is transmitted along the helical axis (16,17). Others suggest that the movement of individual amino acid side-chains could provide this function (18), and one group contends that an electron transfer could disrupt a hydrogen bonding of four tyrosines in $K^+$ channels (19).

Fluorescence (15,20–22), Fourier transform infrared spectroscopy (FTIR) (23–25), and circular dichroism (CD) measured in organic solvents, phospholipid micelles, liposomes, or oriented phospholipid bilayers (15,20,21, 24–34) have been successfully used to probe the solution and membrane-bound conformations of these peptides. Computer modeling studies have been performed to estimate the energetics of moving a charged ion across a lipid bilayer through a pore generated by a bundle of transmembrane helices (35–37). Structural experiments using NMR are yielding important results (12,38–41). In general, these studies have provided several conclusions concerning the solution behavior and membrane interactions of CFPs. Amphipathic helical peptides can exist as monomers and aggregates in solution. Monomers are able to interact much more readily with lipid bilayers and micelles. Depending on the peptide to lipid ratios, type of lipid, ionic strength, pH of the solution, and the hydration of the lipid, the peptide will preferentially orient itself either parallel to or perpendicular to the plane of the bilayer. Many CFPs do not require a potential difference across the bilayer to insert spontaneously into the bilayer. Once in the membrane, the helices associate in a time and concentration dependent manner to form the multistate helical bundles. It is these assemblies that conduct the ions across the bilayer. These studies, when considered together, reveal the transmembrane amphipathic helix to be a dynamic structure. The ability to oligomerize in the membrane into stable ring structures, with a central aqueous pore capable of opening and closing, appears to be driven by the asymmetric alignment of hydrophilic and hydrophobic amino acid residues that seem to obey a unique set of rules.

Putative channel forming segments from large channel proteins behave much like the small naturally occurring CFPs described above. They spontaneously insert into bilayers and self-assemble into an ion-conducting structure, presumably comprised of a parallel array of α-helices. These structures also retain biological activities reminiscent of the native proteins they were modeled after (10, 42–47). These structures are reasonable models for exploring both the oligomerization of transmembrane segments and for defining the molecular events that give rise to channel activity. The beauty of this system emanates from the appearance of a measurable activity that arises from the assembly of an amphipathic transmembrane helix. The activity allows measurement of the effects of amino acid substitutions on either the size of the assemblies or the contribution of the residues to ion selectivity or translocation. The number of helices per channel can be precisely controlled, thus preventing multiple oligomerization states, by tethering the helical segments to a peptide backbone during synthesis. The small size of these assemblies makes them ideally suited for NMR structural studies using either detergent micelle solution NMR or oriented bilayer solid-state NMR.

Pharmacological studies have been a relatively recent addition to the single channel analysis of these model CFP channels. Using a four helix bundle CFP derived from the human L-type dihydropyridine sensitive $Ca^{2+}$ channel, the binding of a local anaesthetic as well as a number of calcium channel blockers with binding affinities on the order of those observed for the full length calcium channel protein have been observed (42,43,48). This avenue of investigation adds a sensitive method of discriminating between channels that truly mimic their parent structures as opposed to those that might produce non-discriminating ionic pores. Once the three dimensional structure for one of the synthetic channels has been solved, rational drug design of both channel agonists and antagonists may be attempted using these coordinates.

Membrane proteins are generally acknowledged to be the most difficult class of proteins for detailed structural analysis. The studies presented above clearly demonstrate the utility of working with channel forming peptides, as model systems, to study events involved in peptide association with the bilayer, insertion into membranes, and assembly into oligomers. The amphipathic helix is a suitable structural motif for the pore of channel proteins that also contributes to the organization, size, function, and stabilization of ionic channels. As an assembled structure these helical bundles can be used to investigate the structure, organization, and function of channels.

Application of synthetic peptides to biological membranes. A synthetic peptide with the sequence of the M2δ segment of the nicotinic acetylcholine receptor from *Torpedo californica* forms ion channels in lipid bilayers that emulate those of authentic acetylcholine receptor ion channels (49). Human erthyrocytes exposed to the synthetic peptide released hemoglobin and K⁻. Evidently the peptide molecules self-assembled in the membrane to form trimers and pentamers (49). Extensive evidence indicates that Cl⁻ secretion drives fluid secretion in Madin-Darby canine kidney (MDCK) cells and in cells cultured from the cystic epithelium of the kidneys of patients with autosomal dominant polycystic kidney disease (APKD), and that a Cl⁻ channel is involved in fluid secretion (50–54). Indeed there is now extensive data indicating that CFTR is the channel involved in that secretion by ADPKD cells (55–57). Apparently, a net secretion of Cl⁻ into the lumen of the cysts leads to an increase in water volume in the cysts, ultimately resulting in kidney dysfunction. However, although there is a precedent for the application of synthetic channel-forming peptides to cells, no one previously has used channel-forming peptides to treat symptoms of any disease.

U.S. Pat. No. 5,543,399 describes the purification and lipid reconstitution of CFTR protein and CF therapy making use of that protein. There is no teaching or suggestion in this reference of the use of relatively small, easily prepared pure peptides, and particularly peptides which are fragments of channel-forming proteins.

U.S. Pat. No. 5,368,712 teaches the use of small peptides reconstituted in artificial membranes as diagnostic tools. This patent does not describe any therapeutic applications using such peptides.

SUMMARY OF THE INVENTION

The present invention is directed to 1) multiple-peptide channel assemblies for transport of anions (e.g., Cl⁻) through epithelial cells, 2) synthetic peptides capable of forming such channel assemblies, and 3) methods of using the channel assemblies in therapeutic contexts for altering the flux of water across epithelial cells.

In preferred forms, the channel assemblies of the invention comprise from 3–6 peptides each having from about 18–30 amino acid residues, and more preferably from about 21–27 residues. The peptides are characterized by the ability of providing, in an embedded channel assembly, transport of anions through a membrane of an epithelial cell and modulation (alteration) of the flux of water through the cell. Moreover, the preferred peptides are soluble in water to a level of at least 10 mM, and more preferably about 25 mM. The peptides of the invention also should exhibit at least about 50% helical content (advantageously at least about 65% helical content) when dispersed in a 40% trifluoroethanol/60% water solution and measured using circular dichroism spectroscopy (CD).

In the case of CF therapies, the channel assemblies are embedded in the cytoplasmic membrane of affected epithelial cells. These peptides spontaneously insert into the cytoplasmic membrane on contact, and spontaneously aggregate within the membrane to form a channel assembly having a hydrophilic internal pore through which Cl⁻ may pass, and an lipophilic external surface allowing solubility of the assembly in the membrane. Preferably, the peptides making up the channel assemblies are identical. In another use, the peptides may spontaneously insert into the basolateral membrane of renal epithelial cells in order to inhibit the flux of water into the adjacent cysts.

The peptides ideally have the amino acid sequence ABC $(X)_n$DEF, wherein A, B, C, D, F and X are individual amino acid residues, n ranges from 12–24 and at least one of the amino acids selected from the group consisting of A, B, and C, is a charged amino acid, and at least one of the amino acids selected from the group consisting of D, E, and F is a charged amino acid (e.g., lysine, arginine, histidine, aspartic acid and glutamic acid). In preferred forms, positively charged amino acids are located at these positions to facilitate the flow of negatively charged ions through the epithelial channel. Additionally, the peptides ideally have at least one of the sequence motifs $(PNNN)_3$, $(PNNNPNN)_3$, and $(PPNNPNN)_3$, wherein P comprises polar amino acids (e.g., serine, threonine, lysine, asparagine, arginine, glutamine, and histidine), and N comprises nonpolar amino acids (e.g., leucine, isoleucine, valine, and alanine); these motifs impart amphipathic characteristics to the peptide, giving each peptide a hydrophilic face and a lipophilic face and allowing a plurality of these peptides to form the channel assemblies described above.

Advantageously, at least one peptide of the synthetic channel assembly has at least 75% homology as compared with a pore-forming segment of a native channel assembly. Suitable protein segments for use as peptides are present in the strychnine-binding α-subunit of the inhibitory glycine receptor from human brain (i.e., the M2 fragment), the inhibitory γ-aminobutyric acid receptor from human brain (i.e., the M2 fragment), and the cystic fibrosis transmembrane conductance regulator from human epithelium (i.e., the M2, M6, M10, and M12 fragments); these fragments have the amino acid sequences presented in SEQ ID NOS: 1 through 6.

It has also been found that highly water soluble peptides in accordance with the invention can be provided, especially through modification of existing peptide fragments. This can be accomplished through the addition of multiple polar amino acid residues on the C- or N-ends thereof. Such peptides are exemplified as SEQ ID NOS: 7–21. Particularly preferred peptides of this class include SEQ ID NOS: 7 and 17. Alternately, internal positions of existing peptides can be replaced with polar amino acid residues to decrease aggregation tendencies. Such an expedient is illustrated in SEQ ID NOS: 8 and 9. Such modifications are designed to alter the net charge of the peptide in question, and thus include its solubility.

The present invention also includes a method of altering the flux of water from an epithelial cell presenting first and second spaced apart surfaces. The method broadly includes providing from 3–6 peptides capable of forming a channel assembly with each of such peptides having from about 18–30 amino acid residues therein. These peptides are contacted with the first surface of an epithelial cell thereby causing the peptides to embed therein and alter the flux of water across the cell. In accordance with the method aspects of the invention, the epithelial cells may be selected from the group consisting of CF-affected epithelial cells, e.g., cells selected from the group consisting of airway, intestinal, pancreatic duct and epidymus epithelial cells. In the case of airway epithelial cells, the method further comprises a delivery step immediately preceding the contacting step, wherein the channel-forming peptides are aerosolized inhaled. In another representative method, the epithelial cells are cystic epithelium of an APKD-affected individual, and the first surface of the epithelial cells is the basolateral membrane of such cells.

The channel-forming peptides of the invention are normally in the L-stereoconfiguration. However, the invention is not so limited and indeed D-stereoconfiguration peptides can also be used. The latter type of peptides may also have significant advantages as they are not degraded in vivo by proteolytic enzymes nor do they elicit an immune response.

BRIEF DESCRIPTION OF THE DRAWINGS

FIG. 1 shows the aminoacid sequence and molecular weight of M2GlyR, the putative transmembrane segment M2 of the strychnine-binding a subunit of the inhibitory glycine receptor, positively charged arginine residues located near the ends of M2GlyR are underlined;

FIG. 10 is a series of five HPLC chromatographs from a single chemical synthesis in which six lysine residues were sequentially added to the N-terminus of M2GlyR (SEQ ID NO: 1), forming SEQ ID NOS: 1, 14, 15, 16, 17, 18, 19 from top to bottom and depicting increased solubility correlated with stepwise addition of three lysine residues and beyond;

FIG. 12 is a graph depicting the solubility in Ringers solution of N-modified M2GlyR sequences (SEQ ID NOS: 1, 14–19) and N-modified M1CFRT sequences (SEQ ID NOS: 25–31);

FIG. 13 is a comparison of solubility in Ringers solution of certain N-modified M2GlyR sequences (SEQ ID NOS: 1, 14–19) indicated by circle data points versus certain C-modified M2GlyR sequences (SEQ ID NOS: 7,20,21) indicated by box data points, wherein the selected N-modified and C-modified sequences have similar net charges;

FIG. 14 is a series of three TOCSY NMR spectra for SEQ ID NOS: 1, 16 and 18 from top to bottom showing that only SEQ ID NO: 18 is in monomeric form;

DETAILED DESCRIPTION OF THE PREFERRED EMBODIMENTS

Figure 2:
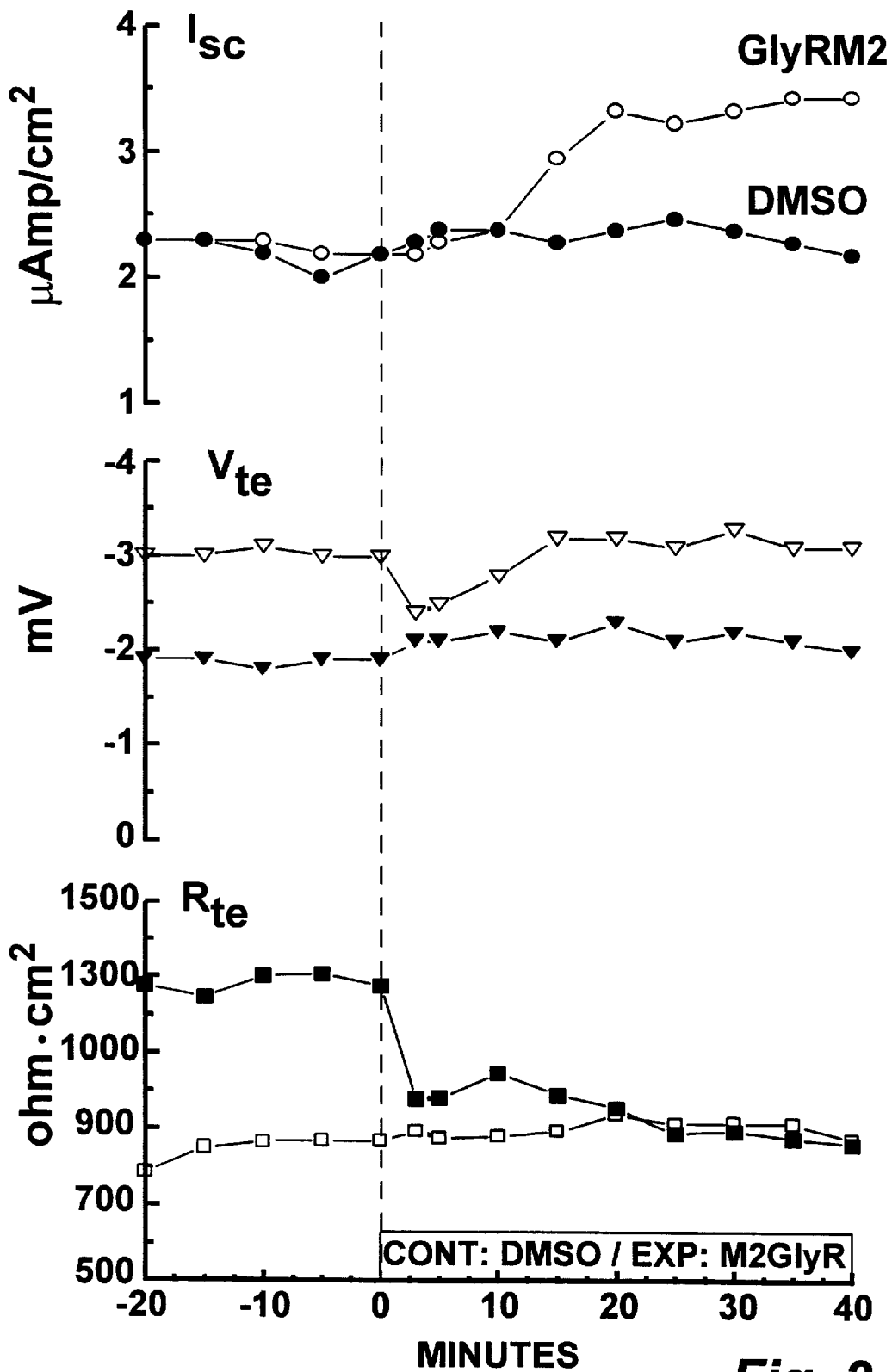
FIG. 2 shows plots illustrating the effect of M2GlyR and of dimethysulfoxide (DMSO) on paired monolayers.

The following examples set forth a synthetic channel assembly for transport of Cl⁻ through the residue. The preactivation, which consisted of incubation of 1-hydroxybenzotriazole (HOBt) in the presence of the condensing agent 2-(1 H-benzotriazol-1-yl)-1,1,3,3-tetramethyluronium hexafluorophosphate (HBTU), resulted in the formation of a highly reactive HOBt-amino acid ester. A ten-fold excess of amino acid (1.0 mmol) over resin sites was weighed out and transferred to a labeled plastic cartridge. Just prior to preactivation, the amino acid was dissolved in 2.1 ml of NMP in the cartridge. This activation reaction began upon the addition of 2.0–2.1 ml (0.9–0.95 mmol) of the 1:1 HOBt:HBTU in dimethylformamide (DMF) reagent. The amino acid was present in slight excess over the HOBt:HBTU to limit the possibility of undesirable side reactions. After the reaction was allowed to proceed for 10 min at room temperature, 1.0 ml of 2M N,N-diisopropylethylamine (DIEA) was delivered to the amino acid cartridge and mixed briefly by bubbling argon. The entire 5 ml solution was then transferred to the RV. This transfer initiated the coupling of the incoming amino acid to the resin-bound amino acid.

The coupling reaction proceeded for 25 min and was terminated by filtering off the soluble reactants. The resin was washed as described above and a second aliquot of preactivated HOBt ester-amino acid (prepared as described above) was added and allowed to react for 25 min. This second addition of the same amino acid was used to maximize the coupling efficiency of the amino acid to the resin. The first reaction usually resulted in about a 95% efficiency and the second reaction increased efficiency to about 99.5%. The remaining 0.5% of the sites were eliminated by a 5 min reaction with 5 ml of a solution containing the following reactants in NMP at the given concentrations: 0.5 M acetic anhydride, 0.125 M DIEA, and 0.015 M HOBt. The RV was again drained and resin was subsequently washed with NMP as described above. The coupling of one amino acid to the resin was then complete. By maintaining high coupling efficiencies for the amino acids and then capping any low reactivity sites during the synthesis, the number and diversity of failed or undesirable side products were significantly reduced, thus making the product easier to purify to homogeneity.

In order to add the next amino acid, the protocol outlined above was repeated with the appropriate N-Fmoc-protected amino acid. The entire sequence was assembled by the successive stepwise repetition of the deprotection, amino acid activation, and coupling steps.

The fully assembled resin-bound peptide was finally washed with dichloromethane (DCM) and dried overnight under reduced pressure. The dried product was weighed and the overall synthetic yield was calculated based on a calculated theoretical 100% efficiency. For a 0.1 mmol-scale synthesis, starting with 196 mg using a resin substitution of 0.510 mmol/g, the theoretical yield is 518 mg. The average dried weight from 10 separate syntheses was 505 mg giving a calculated yield of 97.5% overall with a per-step coupling efficiency of 99.88%.

The peptide was released from the resin and all side chain protecting groups were removed using a chemical cleavage reaction. In this reaction, 500 mg of peptide/resin was incubated with 9.0 mL of trifluoroacetic acid (TFA) in the presence of 0.5 mL of 1,2-ethanedithiol and 0.5 mL of thioanisole at room temperature for 200 min. The mixture containing the cleaved peptide and by-products was removed from the solid resin support by filtration. The peptide was then precipitated by the addition of cold (4° C.) t-butyl methyl ether. The peptide precipitate was harvested by centrifugation and the ether containing the bulk of the cleavage by-products was decanted off. The precipitate was washed with the cold ether and recentrifuged a total of three times. The washed peptide was then dissolved in 20% acetic acid in water and extracted three more times with ether. After each extraction, the ether layer was removed after a brief centrifugation. At this point, the aqueous layer was clear or slightly turbid. After these liquid-liquid extractions, the water layer was shell frozen in a dry ice/ethanol bath and then dried by lyophilization. While the synthesis was complete at this point, the peptide was not ready for administration to the cells.

The peptide produced above was purified to homogeneity by reversed-phase high-performance liquid chromatography (RP-HPLC). The dried crude peptide (5 mg) was dissolved in 1.0 mL of trifluoroethanol (TFE) (Aldrich Chemical Co., Milwaukee, Wis.). A 0.2 mL sample was injected onto a pre-equilibrated polystyrene based $C_4$ semi-prep RP-HPLC column (PLRP-S 300 Å, 7.5×50 mm; Polymer Laboratories, Amherst, Mass.). The column was equilibrated with 18% acetonitrile ($CH_3CN$) in deionized-distilled water containing 0. 1% TFA at a flow rate of 2.0 mL/min using a System Gold 125/166 computer-controlled HPLC instrument (Beckman Instruments, Fullerton, Calif.). After maintaining the 18% for three minutes post-sample injection, a programmed gradient from 18% $CH_3CN$ to 54% $CH_3CN$ over 10 min was then executed. The column was maintained at 54% for 7 min and was then jumped to 80% $CH_3CN$ followed by a 6 min hold prior to returning to the initial conditions. The desired product eluted at 40.5% $CH_3CN$ and was observed by measuring the change in optical absorbance at 215 mm. Multiple runs using the HPLC was required to purify all of the peptide sample. The fractions containing the peptide from successive runs were pooled and lyophilized to dryness.

To confirm that the correct sequence was assembled, an aliquot of the purified material was analyzed by both automated Edman sequencing and mass spectral analyses. For sequencing, 25 picomoles were applied to glass filter that was pretreated with Biobrene (Perkin Elmer, Norwalk, Conn.) and allowed to dry. The filter was then sequenced using an Applied Biosystems Model 473A pulsed-liquid protein sequencer (Perkin Elmer, Norwalk, Conn.). All reagents used on this instrument were obtained from the instrument manufacturer (Perkin Elmer, Norwalk, Conn.). The sequence obtained by this method indicated that the correct amino acids were added in the correct positions of the peptide. Mass spectral analysis was carried out using a Lasermat 2000 matrix-assisted laser-desorption ionization time of flight spectrometer (MALDI-TOF) (Finnigan Corp., San Jose, Calif.). The peptide (1 pmol in 1 $\mu$l of 40% $CH_3CN$ in water) was mixed with 1 $\mu$l of a 10 mg/ml solution of α-cyano-4hydroxycinnamic acid (Aldrich, Milwaukee, Wis.) dissolved in 60% acetonitrile ($CH_3CN$) in deionized-distilled water containing 0.1% TFA along with 1 $\mu$l of a 20 $\mu$M solution of the standard peptide, substance P (Bachem, Torrance, Calif.), with a known mass of 1348.6 Da for the MH+1 ion. After the sample was mixed, 1 $\mu$l was transferred to the etched center of a stainless steel sample slide and allowed to dry. Once dry the sample was placed in the instrument and the mass determined at the lowest power that yielded signal using the added standard to calibrate the instrument. A single observed mass was obtained for the purified M2GlyR peptide. This value was in agreement with the predicted value of 2304.66 Da. Together these two analyses indicated that the correct sequence was assembled, that there were not detectable modifications to the sequence, and that no detectable contaminants were present in the purified peptide sample.

EXAMPLE 2

Determination of Protein Concentrations. Protein concentrations were determined using a normalized micro BCA protein assay in which the color constant was matched to the albumin standard by amino acid analysis. A 100 pmol (by weight of lyophilized peptide) solution of M2GlyR was prepared in DSMO. Several aliquots were removed for gas phase hydrolysis in constant boiling 6M HCl for 24 hr at 110° C. Each data point was analyzed in triplicate. The amino acids were derivatized with PITC to form the PTC-amino acids on an Applied Biosystems Model 420 analyzer (Perkin Elmer, Norwalk, Conn.). Peaks were identified based on their retention times in reverse-phase HPLC (C-18, 2.1 mm ID×250 mm amino acid analysis column; Applied Biosystems, Perkin Elmer, Norwalk, Conn.). The mole-fractions for the amino acids proline, arginine, alanine, valine, and leucine were calculated and used to determine the concentration of the original sample. In a parallel experiment a micro-BCA protein assay (Pierce Chemical Co., Rockford, Ill.)was carried out on a separate aliquot of the original solution and compared to the albumin standard curve. The BCA-assay was then normalized to the value obtained by the more accurate amino acid analysis. For the M2GlyR sequence the BCA assay yielded a value that was 83% of that seen for the amino acid analysis. For subsequent concentration determinations, only the normalized BCA assay was performed. Each peptide yielded a different color constant with the BCA assay, but a reliable conversion factor was determined by performing one careful amino acid analysis along with the BCA assay. Also it was not uncommon for the weighed peptide to contain as little as 35% protein as determined by these other tests. The remaining weight is most likely salt.

EXAMPLE 3

Cell preparation. The MDCK subtype used was derived from original ATCC stock. The methods for carrying continuous subcultures and processing frozen cells have been previously described (52,62). Cells were routinely grown in plastic flasks and passaged every week. Standard growth medium contained a 50:50 mixture of Dulbecco's modified Eagles's medium no. 56–469 and Ham's F12 medium no. 56–659 (JRH Bioscience, Lenexa, Kans.), supplemented with 15 mM HEPES, 24 mM $NaHCO_3$, penicillin-streptomycin, and 5% FBS (JRH Bioscience, Lenexa, Kans.). The cells were incubated at 37° C. in an atmosphere of 5% $CO_2$ 95% room air until they reached 70–80% confluence. The cells were then suspended with the use of trypsin (0.05%) and used to grow monolayers on permeable supports.

To form monolayers, the cells were plated onto the upper surface of a permeant membrane that forms the bottom of a plastic well. Two types were used. One was the Transwell-Col insert (CoStar Co., Cambridge, Mass.) supported in a six-well tissue culture plate. The membranes were coated with Type I and Type III collagen, and were 24.5 mm in diameter. The other type was the Snapwell (Costar Co., Cambridge, Mass.) in which the membrane was coated by a mixture of the same collagen types. During incubation the medium was replaced at 48–72 hr intervals. Confluent monolayers form within 72 hrs. Experiments were performed on the monolayers 6–9 days after the initial plating. Net fluid secretion responses were optimal after six days.

EXAMPLE 4

Using chamber procedures. Confluent monolayers grown on Costar snapwell inserts (0.4 µm pore size, 12 mm dia) (Costar Co., Cambridge, Mass.) were mounted on diffusion chambers (Costar Co., Cambridge, Mass.) specifically designed to be used with the inserts. Each half chamber had a circular opening (9 mm dia) which was covered by the monolayer and contained 4 to 7 ml of bathing medium that was aerated and mixed by bubbling with a gas consisting of 5% $CO_2$ and 95% $O_2$. The temperature of the chambers, bathing medium, and monolayers were maintained at 37° C. Agar bridges containing 3 M KCl and connected to Ag-AgCl electrodes were used to measure transepithelial potential difference ($V_{sc}$). The tips of these bridges were placed close to the monolayer surface. Sections of platinum wire mesh were placed in the rear of the chambers to serve as the current electrodes. The electrical measurements were made with the use of a dual epithelial voltage clamp (EC-825; Warner Instruments, Hamden, Conn.). The instrument provided a variable potential source which was used to offset or cancel any mismatch in the electrode system and a compensating circuit to correct for current-induced potential drops in the chamber fluid during clamping (fluid resistance compensation). The device clamped the voltage across the monolayer at zero to measure $I_{sc}$ and periodically pulsed a current through the system to clamp the voltage at a chosen level in order to provide a measurement of $R_{sc}$. Values for $I_{sc}$ and $R_{tc}$ were corrected for the area of the exposed monolayer. Readings from the voltage clamp device were recorded on a polygraph.

EXAMPLE 5

Fluid secretion measurements. This technique has been previously described (51,52). The apical surface of the confluent monolayer grown on a Transwell was covered with 200 µl of fluid under a layer of mineral oil. A secretagogue was added to either the apical or the basolateral medium and 24 hrs later the entire contents of the apical compartment above the monolayer were aspirated, the aqueous phase separated by centrifugation, and the volume of secreted fluid was measured in a calibrated capillary tube. The rate of fluid secretion was expressed as vol/time/surface area of the monolayer. Fluid secretion was not due to hydrostatic pressure since the height of the liquid layer (including the oil) in the apical compartment was maintained higher than that in the basolateral compartment.

EXAMPLE 6

Alterations in transepithelial transport induced by M2GlyR. M2GlyR was first tested on confluent monolayers of MDCK cells grown on a permeant membrane and mounted in Using chambers. This subculture of MDCK cells has been used as a paradigm of a renal fluid secretory epithelium in an extensive study of fluid secretion mechanisms that participate in the growth of renal cysts in APKD; this cell line evidently uses the same type of Cl⁻ transport mechanisms to generate fluid secretion as those used by airway epithelia (52, 54, 58).

Initial experiments indicated that addition of 100 µM M2GlyR, dissolved in 100 µl DMSO, to the apical bathing medium caused a significant increase in short-circuit current ($I_{sc}$) and a reduction in transepithelial resistance ($R_{tc}$). Subsequent experiments indicated that a concentration of 25 µM M2GlyR was ineffective, 50 µM induced a slight effect on $I_{sc}$, and 150 µM was no more effective than 100 µM. Higher concentrations were not tested because of the limited solubility of the peptide. In all subsequent experiments a concentration of 100 µM was used.

Figures 3A, 3B:
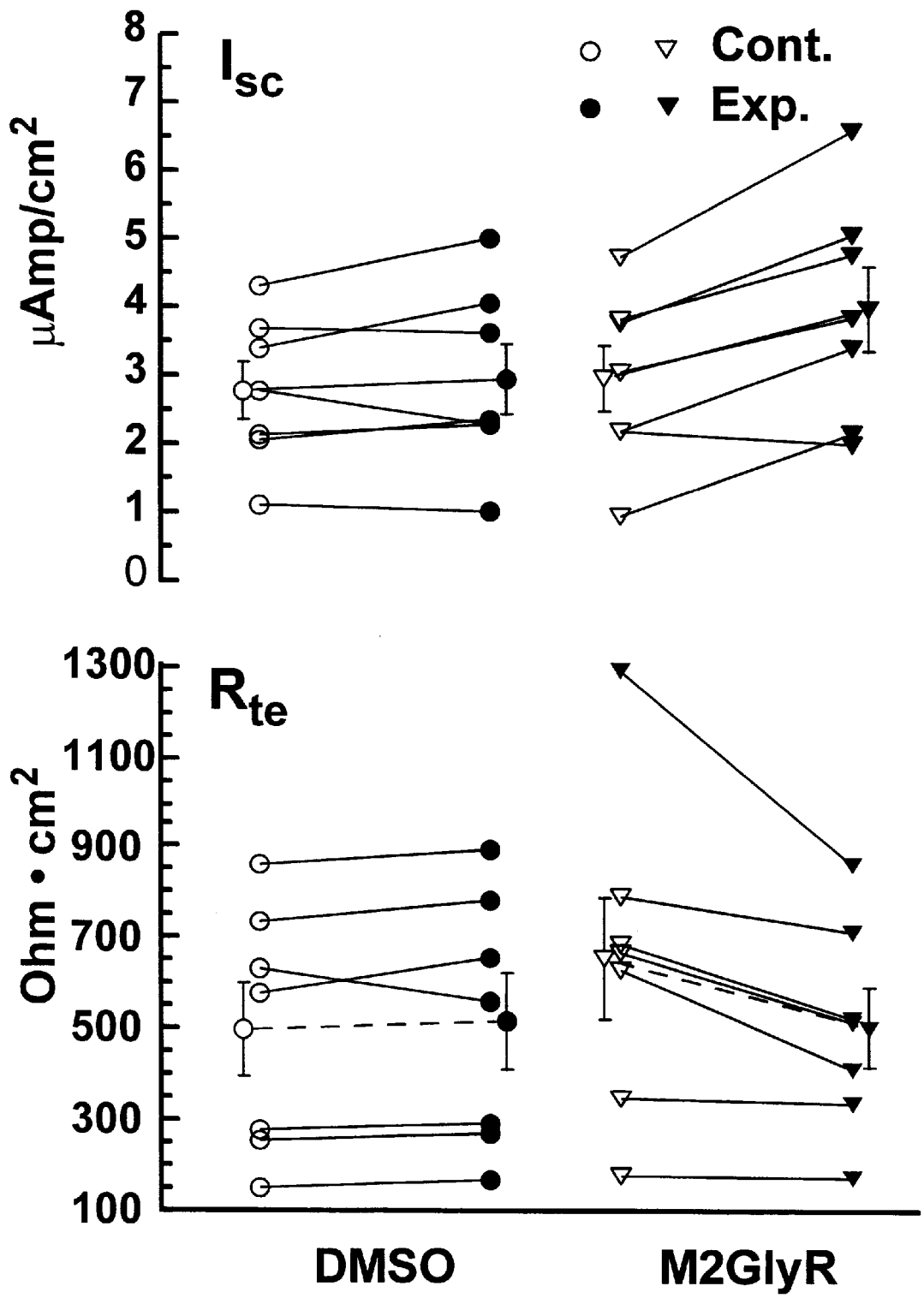
FIG. 3 shows plots illustrating the effect of DMSO and of M2GlyR on $I_{sc}$ and $R_{sc}$.

FIG. 2 presents the results of a typical experiment performed on paired monolayers. Following a 20 min. control period, 100 µM M2GlyR was applied to the apical bathing medium of one monolayer, and the vehicle, DMSO, was added to the apical bathing medium of the other monolayer. The $I_{sc}$ of the experimental monolayer began to rise 15 min later and reached a plateau level at 20 mins. There was a transient fall in $V_{tc}$ and a reduction in $R_{tc}$. DMSO exerted no effect on the three measurements. The results of seven of these experiments are summarized in FIG. 3. M2GlyR induced a 34.5% rise in $I_{sc}$ (p<0.01) and a 22.5% fall in $R_{tc}$ (p<0.05). In a larger series of 21 experiments on unpaired monolayers, 100 µM M2GlyR increased $I_{sc}$ 24.3% (from 3.5±0.6 to 4.4±0.5 µA/cm². p<0.0001) and reduced $R_{tc}$ 14.9% (from 655±57 to 557±48 ohm.cm², p<0.001). No permanent effect on $V_{tc}$ was noted.

The rise in $I_{sc}$, positive current from apex to base, could be due either to a rise in transepithelial active transport of a cation from apex to base (absorption), or to transport of an anion in the opposite direction (secretion). However as described below, it was found that M2GlyR also induced fluid secretion by the monolayers, a finding that is compatible with secretion of an anion but not with absorption of a cation.

EXAMPLE 7

Fluid secretion induced by M2GlyR. The effect of M2GlyR on fluid secretion by the MDCK monolayers was determined in sequential 24 hr periods. The results are summarized in Table 1 below. The effect of the vehicle, DMSO, was tested on 12 monolayers. A minimal rate of fluid secretion occurred in the control period; the addition of DMSO sufficient to bring the concentration of the apical fluid to 1% resulted in no significant change in that rate (paired t test, p>03). The effect of the peptide was tested on 28 monolayers. No net fluid transport occurred in the control period but the addition of 100 µM M2GlyR to the apical solution induced fluid secretion at a rate of 0.150±0.034 µl/cm² surface area/hr (paired t test, p<0.005). These data indicate that M2GlyR does induce fluid secretion by this secretory epithelium.

TABLE 1

Effect of M2GlyR (SEQ ID NO: 1) on fluid secretion.
Fluid Secretion, µL/hr/cm²

| DMSO monolayers, N = 12 | |
|---|---|
| Control | 0.082 ± 0.03 |
| 1% DMSO | 0.032 ± 0.03 |
| Difference | −0.050 ± 0.05 |
| M2GlyR monolayers, N = 28 | |
| Control | −0.012 ± 0.02 |
| 100 µM M2GlyR | 0.138 ± 0.04 |
| Difference | 0.150 ± 0.03* |

Values are means ± SE;
*p < 0.001.

EXAMPLE 8

Effect of Cl⁻ transport inhibitors. In order to determine if the effect of the peptide is indeed to stimulate Cl⁻ secretion, three series of experiments were performed. The basolateral Na-K-2Cl cotransporter is required to raise the intracellular Cl⁻ concentration above its electrochemical equilibrium in order to provide the driving force for Cl⁻ exit through the channel in the apical membrane. Thus the effect of basolateral addition of the cotransporter inhibitor, bumetanide (100 µM), on the stimulation of $I_{sc}$ caused by M2GlyR was tested. In five experiments the addition of the peptide increased $I_{sc}$ from 3.1±0.7 to 4.4±0.8 µA/cm² (p<0.01). The subsequent addition of bumetanide reduced $I_{sc}$ to 1.3±0.3 µA/cm² (p<0.001).

Figure 4:
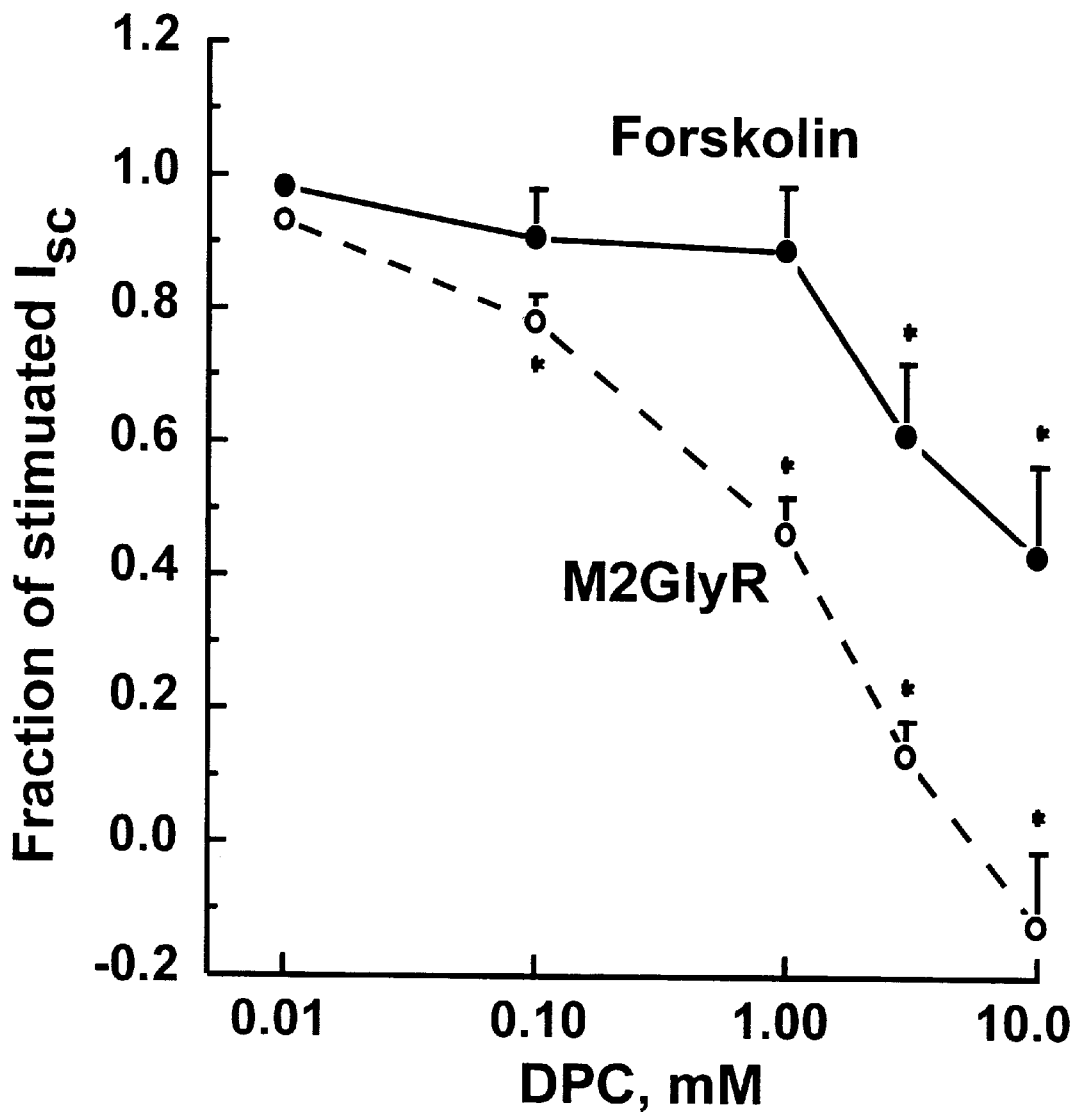
FIG. 4 shows plots illustrating the effect of diphenylamine carboxylate (DPC) on $I_{sc}$ response to forskolin and to M2GlyR.
Figure 5:
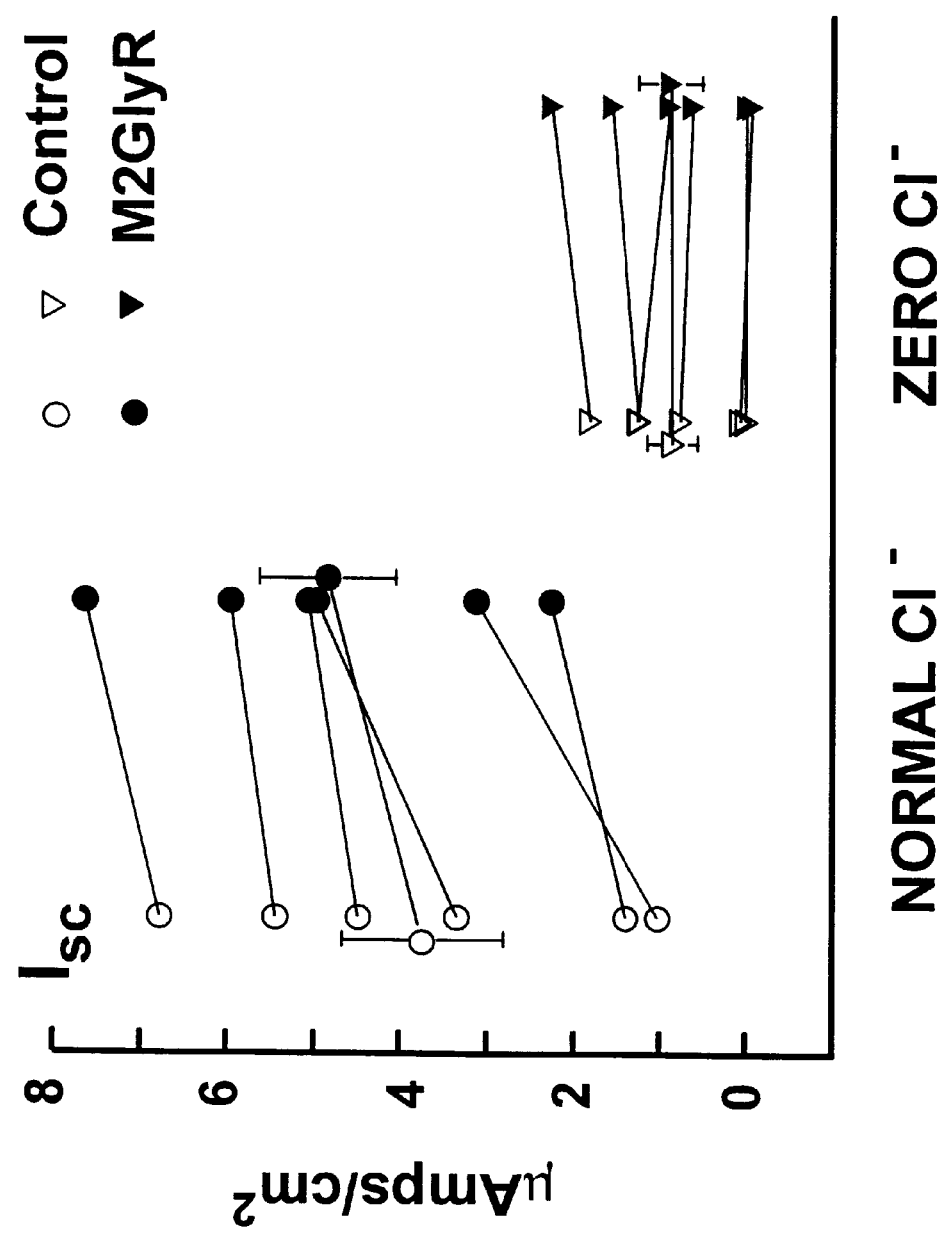
FIG. 5 shows plots illustrating the effect of M2GlyR on $I_{sc}$ in the presence and in the absence of Cl⁻.

The effect of a Cl⁻ channel blocker, diphenylamine-2-carboxylate (DPC) on M2GlyR-stimulated $I_{sc}$ was then tested. In four experiments, following the addition of M2GlyR, the concentration of DPC in tee apical bathing medium was sequentially increased from 0.01 µmM to 10mM. The results are presented in FIG. 4. A DPC concentration of 1 mM was more than sufficient to return $I_{sc}$ to the control level. These results were compared to those obtained in other experiments in which the adenylate cyclase agonist, forskolin, was used to stimulate Cl⁻ secretion via the native Cl⁻ channel. The results suggest that the channel formed by M2GlyR is more Sensitive to DPC than the native channel. In the last series of experiments the effect of the absence of Cl⁻ in the bathing media on M2GlyR-stimulated $I_{sc}$ was determined. Cl⁻ was replaced by cyclamate. Six experiments were performed on paired monolayers. The control monolayers were bathed by the normal Cl⁻-containing media. Following a control period, 100 µM M2GlyR was added to the apical bathing medium of both monolayers. The results are presented in FIG. 5. In the control period the $I_{sc}$ of the monolayers bathed in the zero Cl⁻ media was only 23% of the $I_{sc}$ measured in the monolayers immersed in the control media. M2GlyR stimulated the $I_{sc}$ of the control monolayers by 29% (p<0.01) but exerted no effect on the monolayers bathed in the 0 Cl⁻ solution (p>0.8).

The results of these three series of experiments indicate that the effect of M2GlyR is inhibited by a blocker of the Na-K-2Cl cotransporter and by a Cl⁻ channel blocker. In addition the peptide exerted no effect on the MDCK monolayers in the absence of Cl⁻ in the bathing media. These data demonstrate that the ability of the peptide to stimulate $I_{sc}$ and fluid secretion in this epithelium is due to stimulation of Cl⁻ secretion.

EXAMPLE 9

Delivery system for airway epithelium. The ability of M2GlyR to generate fluid secretion by secretory epithelium shows that this peptide may provide a therapeutic approach to the respiratory problems encountered by patients with CF. One of the problems associated with applying the tide to animals or humans is the method of delivery. M2GlyR has been successfully aerosolized in the presence and absence of surfactant using methods for aerosolizing proteins for delivery to the respiratory tract (59–61). For those experiments in which the surfactant was added, the peptide was mixed with three different surfactants: L9 (polyoxyethylene-9-lauryl ether), Tween-40 (polyoxyethylene sorbitan monopalmitate), and Tween-80 (polyoxyethylene sorbitan monooleate). The propellent for all experiments was dimethylether. The peptide was quite soluble in the propellent alone and upon aerosolization yielded particles primarily in the 5.0–7.5 micron range. In the presence of the surfactants the average size of the particle decreased with L9 and Tween-40 giving 2.5–5.0 micron particles and Tween-80 yielding 1.0–2.5 micron particles.

These experiments demonstrate that a drug delivery route to the respiratory tract is available. It is possible that surfactant may indeed be beneficial for delivery to the apical surface of airway epithelial cells by increasing the penetration of the peptide through the mucous layer.

EXAMPLE 10

Response of normal and CF epithelial cells to synthetic peptides. Three cell lines are utilized in evaluating the potential of synthetic peptides to induce Cl⁻ and fluid secretion in secretory epithelial cells that lack functional CFTR. These peptides include peptides having the amino acid sequences presented in Sequence ID Nos. 1 through 6.

CFPAC-1: This cell line was established from a pancreatic adenocarcinoma in a patient with CF(71). These cells share characteristics with pancreatic duct cells. Anion transport and single Cl⁻ channel activity can be induced in these calls by $Ca^{2+}$ ionophores but not by adenylate cyclase agonists or cAMP analogues. These cells contain the mutated gene that results in phenylalanine-508 deletion in the structure of CFTR.

CFPAC-PLJ and CFPAC-PLJ-CFTR: Amphotropic retroviruses were used to transduce cDNA for CFTR into CFPAC-1cells (72). The resulting cells, CFPAC-PLJ-CFTR, possess a cAMP-activated Cl⁻ conductance of 9 pS that is insensitive to the disulfonic stilbenes, DIDS and DNDS (72, 73). The CFPAC-1 cells were also transfected with control retrovirus to produce the CFPAC-PLJ cell line which was shown to not contain the cAMP-activated Cl⁻ conductance (72). Kersting et al. (74) have grown these cells on permeable supports (CFPAC-PLJ on cellagen membrane [ICN, Costa Mesa, Calif.]), and CFPAC-PLJ-CFTR on polycarbonate filters (Costar Co., Cambridge, Mass.). The CFPAC-PLJ monolayers exhibited a transepithelial resistance in the range of 900 ohmcm² and the resistance of the CFPAC-PLJ-CFTR monolayers was about a third of that. Fluid transport by these monolayers was successfully measured. The CFPAC-PLJ cells absorbed fluid and no net fluid transport was observed in the CFPAC-PLJ-CFTR in the absence of adenylate cyclase agonists (74).

These three cell lines are cultured in Iscove's modified Dulbecco's medium (Sigma, St. Louis, Mo.). The media is supplemented with 10% FBS (71). Monolayers of these cells are prepared as described above. The effect of forskolin and membrane permeant analogues of cAMP on the transepithelial electrical properties of the monolayers and on fluid secretion by the monolayers is characterized. The effect of M2GlyR is characterized in the same way. Various transport inhibitors are tried, notably amiloride.

EXAMPLE 11

Effect of peptides on animal models of cystic fibrosis. Experiments are performed on tissue from normal rats and on tissue from an animal model of CF. A method of delivery of the peptide to the airways of intact rats also is developed. Young adult, Sprague Dawley rats and the CFTR knockout mouse developed by Snouwaert et al (84) are used. The CFTR-/-animals have extensive gastrointestinal abnormalities. However, relatively little pulmonary involvement has been noted. When experiments are performed on tissue, the animals are sacrificed by peritoneal injection of an overdose of pentobarbital.

Fluid transport is determined in segments of the proximal small intestine using a gavimetrc technique. The segments are filled with a Ringer's solution containing no glucose or amino acids (to minimize fluid absorption) and bathed in Ringer's solution aerated with 5% $CO_2$–95% $O_2$ and maintained at 37° C. The segments are removed from the bath at intervals, gently blotted and rapidly weighed. Alternating segments of the same intestine are filled with a solution containing the vehicle, and a solution containing the peptide to be tested and their rates of fluid gain or loss are compared. Aerosols containing M2GlyR and other synthetic peptides are administered to conscious rats at varying doses and for varying periods of time. The rats are then observed for two hours and sacrificed. Their lungs are removed, weighed and, in some cases, are fixed, sectioned, and stained.

Intestinal fluid transport experiments are first performed on rats. Fluid transport in the presence and absence of the synthetic peptides are tested to determine if the peptides will generate fluid secretion by this intact tissue. Fluid transport in the presence and absence of forskolin are tested for purposes of comparison. Experiments with channel blockers are also performed. Similar experiments are performed on CF mice. CFTR +/+, +/–, and –/– animals are used. Experiments are performed with forskolin, other adenylate cyclase agonists, or permeant cAMP analogs. These experiments document the involvement of cAMP-activated channels in fluid secretion in each type of animal. Experiments are then performed with the synthetic peptides in the same manner as in the rats to determine their effect on fluid transport.

Conscious rats are used in airway delivery experiments. Aerosols with particles of different size and with or without various surfactants are tested. Experiments are performed with M2GlyR. During the exposure and in the period following exposure, the animals are observed for signs of excessive fluid secretion (such as frothing at the nares). After sacrifice, the lungs are weighed to determine if edema has occurred.

Conclusions

Monolayers of MDCK cells grown on a permeant membrane were mounted in Using chambers. Application of M2GlyR to the apical membrane resulted in an increase in positive short-circuit current ($I_{sc}$) from apex to base and a fall in the transepithelial resistance ($R_{tc}$). The subsequent application of the $Cl^-$ channel blocker, diphenylamine carboxylate (DPC), to the apical surface reduced $I_{sc}$. Basolateral addition of bumetanide, an inhibitor of the Na-K-2Cl cotransporter, caused the same effect. M2GlyR did not affect $I_{sc}$ when the monolayers were bathed in Cl-free media. These data demonstrate that the peptide induced $Cl^-$ secretion via a transcellular pathway. The alteration in ion transport affected fluid transport by the $MDCK^-$ monolayers. M2GlyR stimulated fluid secretion over 24 hr collection period. Thus, the peptide is not only capable of generating fluid secretion in this secretory epithelia, its effect is also relatively long-lasting.

These findings show that the peptide enters the apical membrane and assembles into oligomers that increase $Cl^-$ conductance. Since this subtype of MDCK cells maintains cell $Cl^-$ concentration above electrochemical equilibrium in the absence of secretory stimuli (58), the necessary gradient exists to drive $Cl^-$ from the cell into the apical medium. Evidently the cell maintains $Cl^-$ secretion via a $Cl^-$ entry mechanism residing in the basolateral membrane, most likely the Na-K-2Cl contransporter. The secretion of $Cl^-$ establishes the gradient for passive secretion of $Na^-$ via the paracellular pathway. The resulting osmotic gradient then drives fluid secretion.

EXAMPLE 12

In this example, certain physiological effects of wild type and lysine-modified peptides were determined.

Peptide synthesis. M2GlyR peptide (SEQ ID NO: 1) and related analogs (SEQ ID NOS: 7 and 24) were prepared using solid-phase peptide synthesis employing an automated base-labile Fmoc-strategy with a p-hydroxymethylphenoxymethyl polystyrene (HMP)-lysine resin (Applied Biosystems Model 431A peptide synthesizer, Perkin Elmer, Norwalk, Conn.). All solvents were reagent grade unless otherwise indicated. Protected amino acids were purchased from one or more of the following vendors (Perkin-Elmer, Bachem, Torrance, Calif.; Peninsula Laboratories, Belmont, Calif. and Peptides International, Louisville, Ky.). The Fmoc group was removed by 22% piperidine (v/v) in N-Methylpyrrolidinone (NMP). A condensing agent, 2-(1 H-beazotriazol-1-yl)-1,1,3,3-tetramethyluronium hexafluorophosphate (HBTU), was used to prepare highly reactive HOBt-amino acid esters, used in the coupling reaction to the resin (a ten fold excess of amino acid). The resin was washed and a second aliquot of the same preactivated HOBt ester-amino acid was added to ensure high coupling efficiencies. The remaining unreacted N-terminal sites were blocked with acetic anhydride.

Assembly of the entire sequence of the peptides was achieved by the successive step-wise repetition of the deprotection, amino acid activation and coupling steps. Fully assembled resin bound peptide was then washed with dichloromethane (DCM) and dried overnight under reduced pressure. The dried product was weighed and the overall synthetic yield was calculated. The peptide was cleaved from the resin with 90% trifluoroacetic acid (TFA), 5% 1,2-ethanedithiol plus 5% thioanisole. Unbound peptide was precipitated with t-butylmethyl ether, washed twice with ether and dissolved in 5% acetic acid. After three extractions of the aqueous layer with ether, the water layer was dried by lyophilization.

The prepared peptide was purified to homogeneity by reversed-phase high performance liquid chromatography (RP-HPLC) with a polystyrene based C4 semi-prep RP-HPLC column (PLRP-S 300A, 7.5 I.D.×50 mm, Polymer Laboratories, Amherst Mass.) and dissolved in 20% acetonitrile. The desired product was eluted by monitoring the optical absorbance at 215 nm and redried by lyophilization. To confirm that the correct sequence of the peptide had been assembled, an aliquot of the purified material was analyzed by both automated Edman sequencing (Applied Biosystems Model 473A pulsed-liquid protein sequencer; Perkin Elmer) and mass spectral analyses (Lasermat 2000 matrix assisted, laser desorption, ionization time of flight spectrometer (MALDI-TOF) (Finnigan Corp., San Jose Calif.). The 23 residue peptide, M2GlyR (SEQ ID NO: 1), has a mass of 2304.6 Da while the 27 amino acid sequences of C-$K_4$-M2GlyR (SEQ ID NO: 7) and a scrambled sequence, C-$K_4$-SCRAMBLED (SEQ ID NO: 24), have a mass of 2817.4 Da.

Cell culture protocol The procedure for maintaining the epithelial cell culture, Madin-Darby canine kidney cells (MDCK) has been described in detail (Grantham et al., 1989). Briefly, a subculture of MDCK cells, originally obtained from the American Type Culture Collection, were maintained as subconfluent monolayers on plastic in a 1:1 mixture of Dulbecco's modified Eagle's medium and Ham F12 (DME/F12: JRH Biosciences, Lenexa, Kans.) supplemented with 1% fetal bovine serum (FBS: HyClone, Logan, Utah) and 100 IU/mhL penicillin G and 0.1 mg/mL streptomycin (P/S). Cells were allowed to propagate on plastic until they were harvested by trypsinization. All media additives and drugs were purchased from Sigma Chemical (St Louis, Mo.) unless noted otherwise.

Measurement of fluid transport. The method for measuring fluid transport across confluent monolayers of epithelial cells has been previously described (Neufeld, et al.; 1991). MDCK cells (0.8 to $1.0 \times 10^6$ cells) were plated onto individual permeable cell culture supports (Transwell-Col, 24.5 mm diameter: CoStar Corp, Cambridge, Mass.). Confluent monolayers were obtained within 3 days and the fluid collection experiments were initiated on days 5 through 7. To begin the experiment, the fluid bathing the apical surface of the monolayers (upper surface of the Transwell) was removed by aspiration and 200 µL of defined media (DME/Ham's F 12, P/S, 5 µg/mL insulin, 5 µg/mL transferrin, and 5 ng/mL selenite (ITS), $5 \times 10^{-8}$ M hydrocortisone, and $5 \times 10^{-5}$ M triiodothyronine) was placed on the upper surface. The apical fluid was covered with 1.5 mL of sterile, water-saturated mineral oil to prevent evaporation of the fluid. The volume of the basolateral media (2.5 mL) was sufficient to prevent a hydrostatic pressure gradient across the monolayers. The monolayers were incubated for 24 hours at 37° C. In a humidified environment. After 24 hours, the fluid and oil were collected and the monolayer was rinsed with mineral oil to insure that the maximal amount of fluid was collected. The oil and fluid mixture was centrifuged and the fluid droplet at the bottom of the test tube was measured using calibrated microcapillary tubes(Drummond, Broomall, Pa.). The volume of this fluid, minus 200 µL (corrected for recovery), was used to calculate the rate of fluid transport during the 24 hours.

Electrical measurements. MDCK cells ($2.5 \times 10^5$) were plated on permeable supports (Snapwell, 12 mm dia.; Costar Corp), coated with a mixture of types I and III collagen (ICN, Costa Mesa, Ca.). The Snapwell supports were placed in a 6 well culture plate containing DME/F12+P/S and 1% FCS (0.4 mL in the upper part and 5 mL in the lower). MDCK monolayers were allowed to reach confluency and after 5 days of growth were mounted in Using chambers designed for cell culture (Costar). The position of the monolayer and the supporting membrane separated the apical and the basolateral compartments. Both sides of the monolayers were bathed in 5 mL of a Ringer's solution containing (in mM); 147 $Na^+$, 119 $Cl^-$, 20 $HCO_3^-$, 6 alanine, 5 $K^+$, 5 acetate, 5 glucose, 4 lactate, 2.5 $HPO_4^-$ 1.2 $Mg^{+2}$, 1.2 $SO_4^{-2}$ 1 citrate, 0.5 butyric acid and 14 raffinose. The media in each half-chamber was circulated by a bubble-lift method with a gas mixture of 95% $O_2$/5% $CO_2$ and maintained at 37° C. In experiments in which we removed chloride from the Ringer's solution, the molar equivalent of cyclamate was used.

The transepithelial voltage was measured using glass capillary tubes containing a plug of 5% agar in 3 M KCl and situated near each side of the cell layer. The glass tube was filled above the agar plug with 3 M KCl and Ag/AgCl electrodes were inserted into the KCl. Current electrodes consisted of a coil of platinum wire (30 gauge) located at the ends of each half-chamber. Transepithelial potential ($V_{tc}$); the short-circuit current ($I_{sc}$), the current necessary to clamp the voltage to zero; and the transepithelial resistance ($F_{tc}$) were measured at five minute intervals with a dual epithelial voltage clamp apparatus (Warner Instrument, Hamden, Conn.) as previously described in detail (Mangoo-Karim et al.; 1995). The average of the last two measurements in each period were used for comparison between pairs of monolayers and among each group.

In electrophysiological studies, niflumic acid, 5-nitro-2-(3-phenylpropylamino)-benzoate (NPPB, provided by SmithKline Beecham), diphenylamine-2-carboxylate (DPC, Fluka Chemika), and glibenclamide were dissolved in 100% ethanol. The maximal final concentration of ethanol, 0.5%, was without effect on $I_{sc}$.

Cyclic adenosine monophosphate measurements. Confluent monolayers of MDCK cells were incubated in defined media (1.7 mL apical and 2.5 mL basolateral) or defined media containing either 10 µM basolateral forskolin or 500 µM apical C-$K_4$-M2GlyR (SEQ ID NO: 7) for two hours. Monolayers were rinsed in $Ca^{+2}$-, $Mg^{+2}$-tree phosphate buffered saline (PBS), then treated with 5% trichloroacetic acid (TCA) to deactivate endogenous phosphodiesterases. TCA was removed by extraction with a mixture of water and ether. Intracellular cAMP remained in the aqueous phase. After the water and ether phases separated, the water phase was collected. Relative levels of intracellular cAMP were determined by radioimmunoassay (Biomedical Technology Inc, Stoughton, Mass.) using methods previously described (Krishna and Terranova; 1987).

Statistical analysis. Sequential measurements of the $I_{sc}$, $V_{tc}$, and $R_{tc}$ were compared by repeated measures analysis of variance (ANOVA) and the Student-Newman-Keuls (S-N-K) multiple comparison post-test. The Kruskal-Wallis Nonparametric ANOVA and the Dunn's multiple comparison test was used in determining statistical significance among the rates of fluid secretion and in the measurements of intracellular cAMP levels. Significant effects or changes were considered to have occurred when p<0.05.

Results

Electrical measurements. MDCK cells were grown as confluent monolayers on permeable supports and mounted in Using chambers. $I_{sc}$, $V_{tc}$ and $R_{tc}$ were measured at five minute intervals before and after the addition of 100 µM C-K$_4$-M2GlyR (SEQ ID NO: 7) to the apical media The upper panel of FIG. 6 displays a typical change in $I_{sc}$, measured in $\mu A/cm^2$, during a 45 minute exposure of C-K$_4$-M2GlyR (SEQ ID NO: 7). In the absence of the peptide, the MDCK monolayers exhibited a positive $I^{SC}$ (from the apical to the basolateral surface), consistent with previous results (Mangoo-Karim et al.; 1995). Five minutes after the application of the peptide, $I_{sc}$ began to increase and by 30 minutes had reached a level 3.3 $\mu A/cm^2$ above control. The addition of 100 µM basolateral bumetanide, an inhibitor of the Na$^-$/K$^-$/2Cl$^-$ cotransporter, blocked the peptide-generated current.

Figure 6:
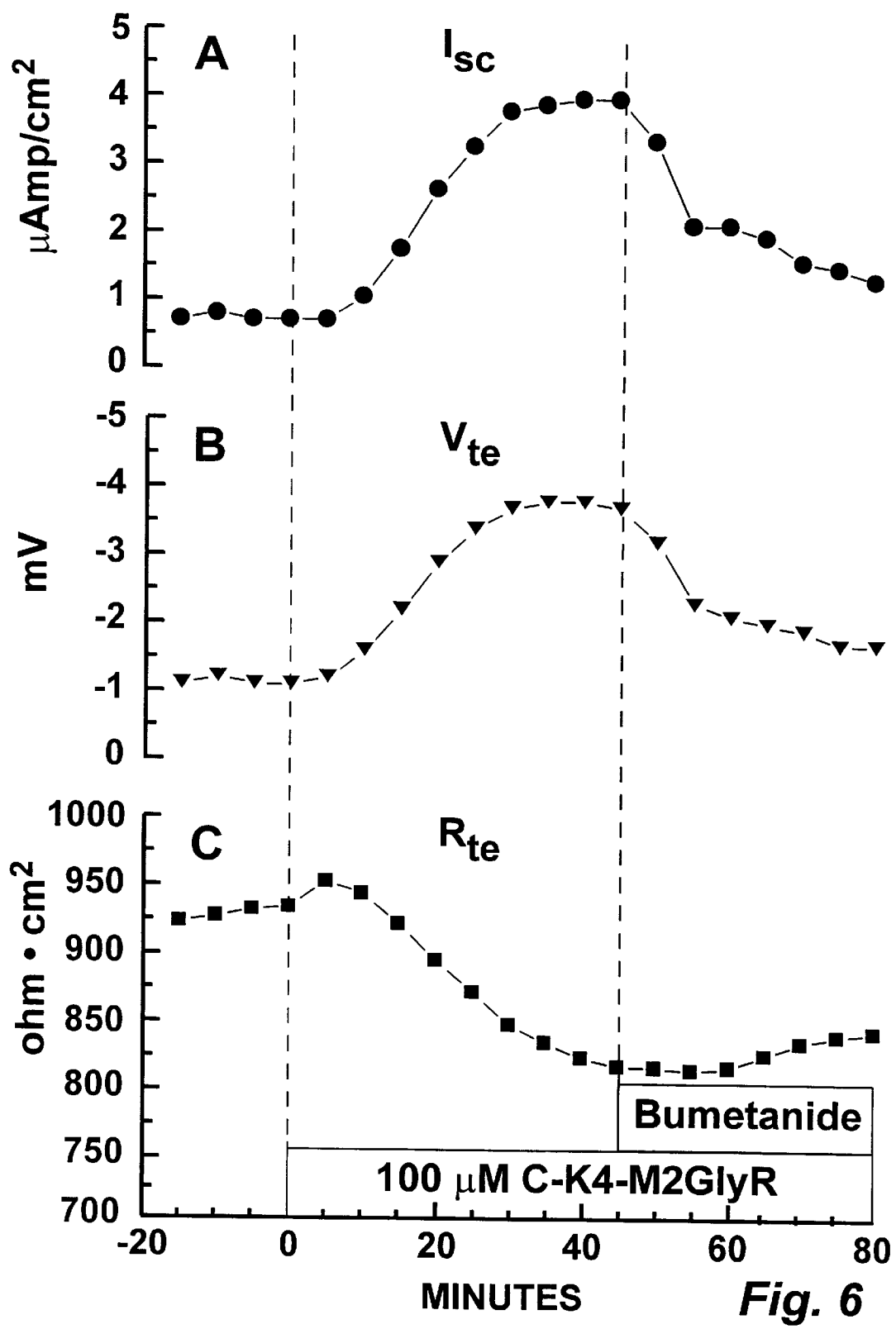
FIG. 6 is a three panel graph illustrating the effect of 100 μM apical C-K₄-M2GlyR (SEQ ID NO: 7) and the subsequent addition of 100 μM basolateral bumetanide on electrical measurements across MDCK monolayers.

An apically negative transepithelial potential difference ($V_{tc}$, mV) was recorded in the control period (panel B in FIG. 6). The addition of the peptide to the apical fluid hyperpolarized the monolayer by -2.7 mV. Bumetanide, reduced $V_{tc}$ towards the value recorded prior to the addition of the peptide. The resistance across the cell layer, $R_{tc}$, decreased by 112 Ohms.cm$^2$ with exposure to the peptide (panel C in FIG. 6). There was a modest increase in $R_c$ with the addition of bumetanide.

The results obtained in 28 monolayers treated with 100 µM C-K$_4$-M2GlyR (SEQ ID NO: 7) are summarized in Table 2. C-K$_4$-M2GlyR (SEQ ID NO: 7) significantly increased $I_{sc}$ from 0.8±0.1 to 3.3±0.4 $\mu A/cm^2$, p<0.0001, and hyperpolarized $V_{tc}$ from -1.5±0.4 to -3.5±0.6 mV, p<0.0001. $R_{tc}$ decreased from 1399±341 to 1013±171 Ohms.cm$^2$, p<0.05.

In other experiments (n=2), the duration of the effect induced by the peptide was tested. $I_{sc}$ remained relatively constant for the first two hrs after the addition of the peptide. After three hrs, the C-K$_4$(SEQ ID NO: 7)stimulated current was 90% of the current recorded at 60 minutes and decreased to 55% after four hrs. In washout experiments (n=3), $I_{sc}$ was measured after removing C-K$_4$-M2GlyR (SEQ ID NO: 7) from the bath. One hour after removal of the peptide, 39% of the stimulated current remained and after two hours, there was no persisting effect of the peptide.

Figure 7:
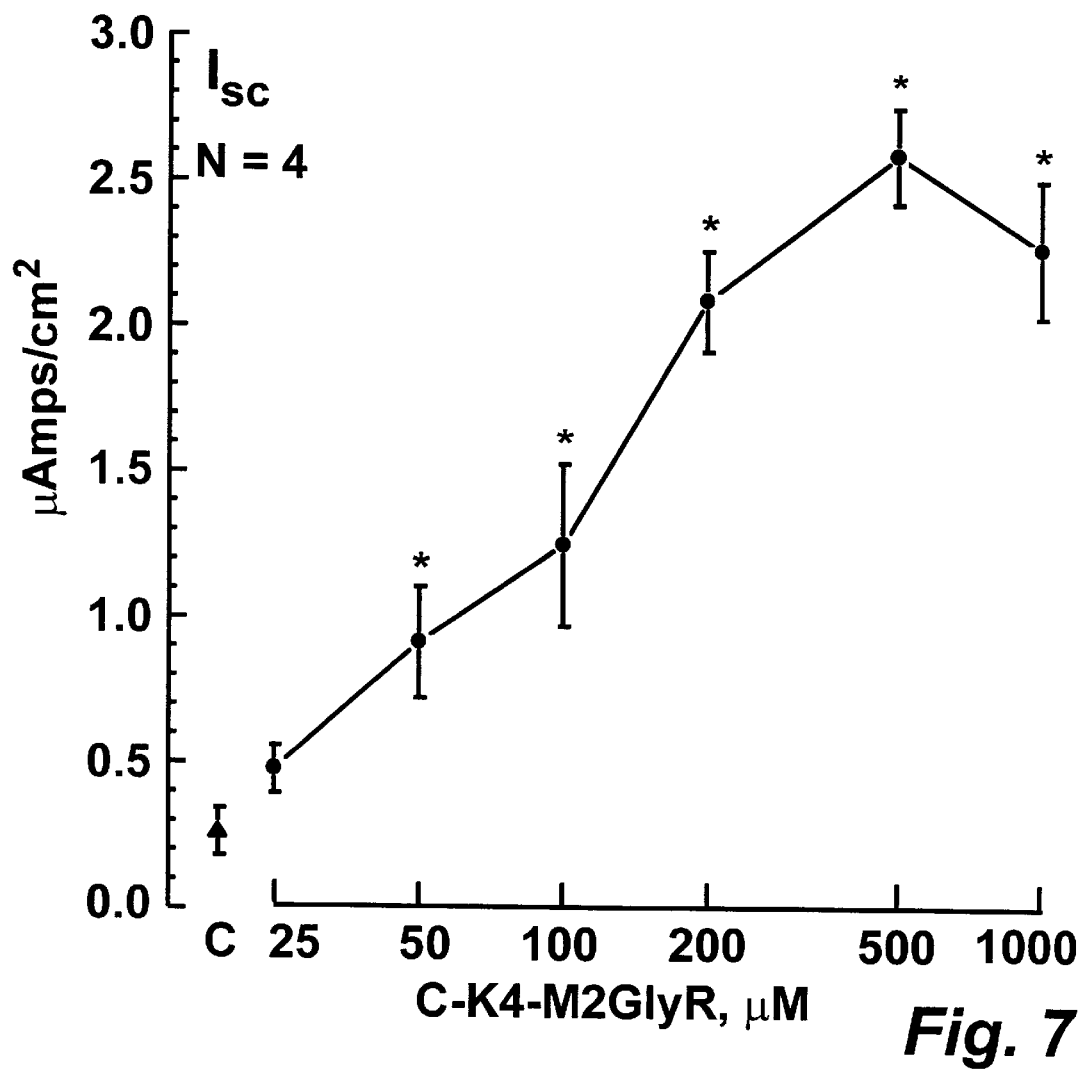
FIG. 7 is a graph illustrating the effect of varying doses of C-K₄-M2GlyR (SEQ ID NO: 7) on $I_{sc}$ in MDCK monolayers, wherein the concentration of the peptide applied to the apical surface was sequentially increased after the response to the previous addition had reached a steady state, and wherein the asterisk represents comparison to the control period, p<0.05.

The improved solubility of the C-K$_4$-M2GlyR (SEQ ID NO: 7) over the wild type sequence (M2GlyR) (SEQ ID NO: 1), permitted testing of the effect of higher doses of the peptide on $I_{sc}$ (see Example 13). The response to varying doses of C-K$_4$-M2GlyR (SEQ ID NO: 7) was determined in 4 experiments (FIG. 7). The first data point (C) is the average Isc measured at the end of the control period. The concentration of the peptide is plotted on a log scale ranging from 25 µM to 1 mM peptide. A significant increase in $I_{sc}$ occurred with doses at and above 50 µM. Short-circuit current increased by 235% with 50 µM; 359% with 100 µM; 856% with 500 µM and 737% with 1 mM peptide. Thus, the maximal stimulation averaged 2.3 µA above the baseline current with 500 MM C-K$_4$-M2GlyR (SEQ ID NO: 7). For most experiments, 100 µM peptide was used, since this concentration provided reliable stimulation and was more cost effective than higher doses.

To confirm that the increase in $I_{sc}$ induced by the addition of the C-K$_4$-M2GlyR (SEQ ID NO: 7) was not simply due to a non-specific effect of the peptide, the effect of C-K$_4$-M2GlyR (SEQ ID NO: 7) on $I_{sc}$ was compared to that of a scrambled sequence of the peptide, C-K$_4$-SCRAMBLED (SEQ ID NO: 24). The scrambled peptide consisted of a random sequence of the same 23 amino acids as M2GlyR (SEQ ID NO: 1) plus four lysine residues on the carboxyl-terminus. Four pairs of MDCK monolayers were treated with either C-K,-M2GlyR (SEQ ID NO: 7) or C-K$_4$-SCRAMBLED (SEQ ID NO: 24). $I_{sc}$ increased from 1.6 ±0.3 to 6.2±1.0 $\mu A/cm^2$, p<0.001, with the addition of 500 µM C-K$_4$-M2GlyR (SEQ ID NO: 7) to the apical media. The application of 500 uM C-K$_4$-SC LED (SEQ ID NO: 24) had no effect on $I_{sc}$ (1.6±0.3 to 1.3±0.4 $\mu A/cm^2$).

Effect of bumetanide. The effect of basolateral bumetanide on the electrical properties of eight monolayers treated with C-K$_4$-M2GlyR (SEQ ID NO: 7) are summarized in Table 3. The application of 100 µM C-K$_4$-M2GlyR (SEQ ID NO: 7) to the apical media increased the current from 1.3±0.4 to 3.2±0.8 $\mu A/cm^2$, p<0.001. Basolateral bumetanide (100 µM) decreased $I_{sc}$ to 1.4 $\mu A/cm^2$, p<0.001. Thus, bumetanide inhibited 97% of the peptide-generated $I_{sc}$. The changes in $V_{tc}$ were similar to the changes in $I_{sc}$. Bumetanide reduced the $V_c$ from -7.0±1.3 to -2.8±0.6 mV, p<0.001 (the latter value does not differ from the control). The effect of bumetanide on $R_{tc}$ was not significant.

Effect of Cl$^-$ channel blockers. We tested a variety of Cl$^-$ channel blockers on the $I_{sc}$ generated by apical application of C-K$_4$-M2GlyR (SEQ ID NO: 7). MDCK monolayers were treated with 100 µM C-K$_4$-M2GlyR (SEQ ID NO: 7) for 40 minutes, followed by the addition of 100 µM inhibitor to the apical media for 20 minutes. Table 4 displays the $I_{sc}$ in the control period and after the addition of peptide and the percent change in $I_{sc}$ with the exposure to each inhibitor. A negative change indicates a reduction in the current. The sensitivity sequence of the peptide-induced current to the Cl$^-$ channel blockers was niflumic acid≧NPPB>DPC>glibenclamide>>>DIDS. DIDS did not inhibit $I_{sc}$ in any of the five experiments. The increase in $I_{sc}$ with the addition of DIDS was not significant (p=0.07) and may be due to an effect on other transport mechanisms.

Figure 8:
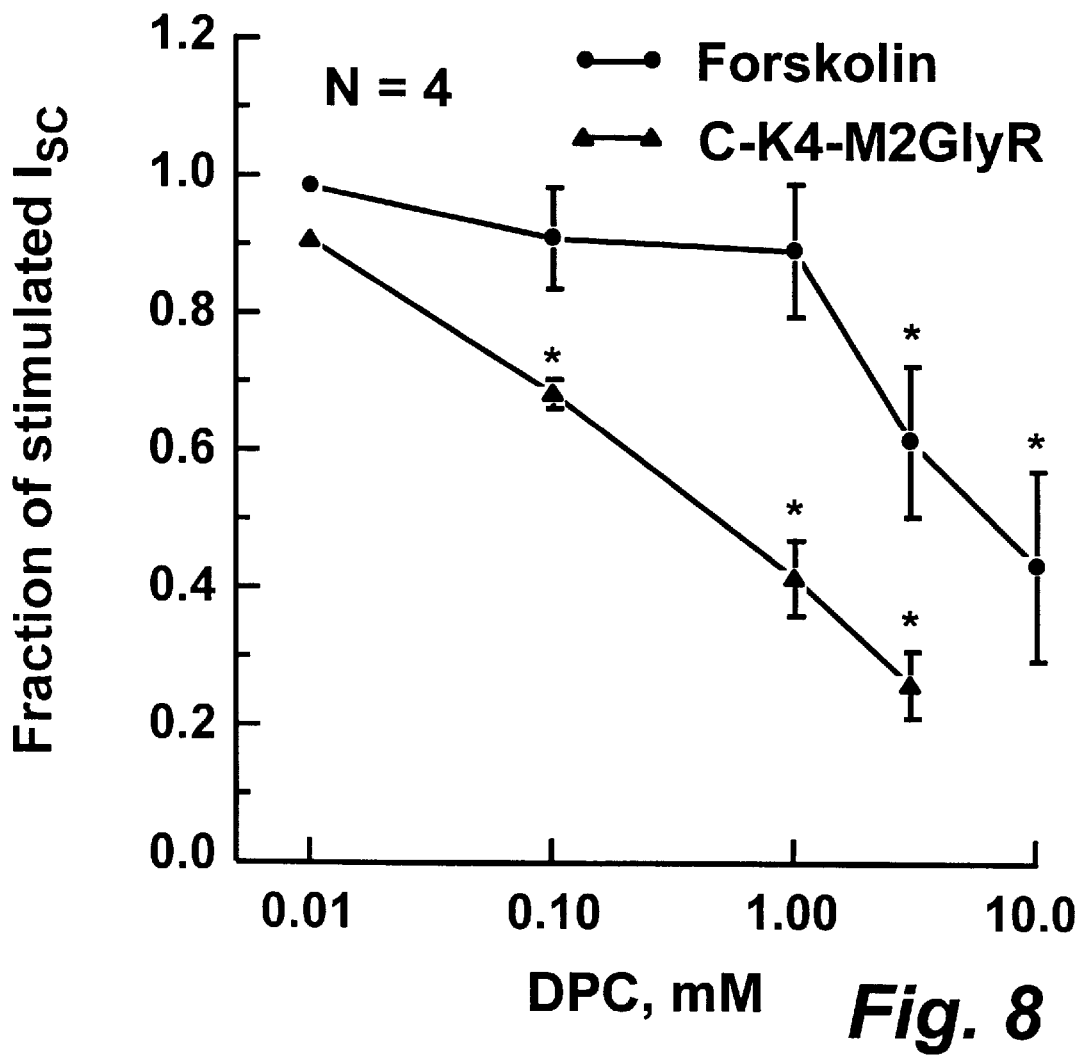
FIG. 8 is a graph illustrating the effect of varying doses of DPC on $I_{sc}$ stimulated by C-K₄-M2GlyR (SEQ ID NO: 7) or forskolin, wherein monolayers were exposed to the peptide for 40 minutes prior to the additions of DPC, where n=4 for each group and *p<0.05.
Figure 9:
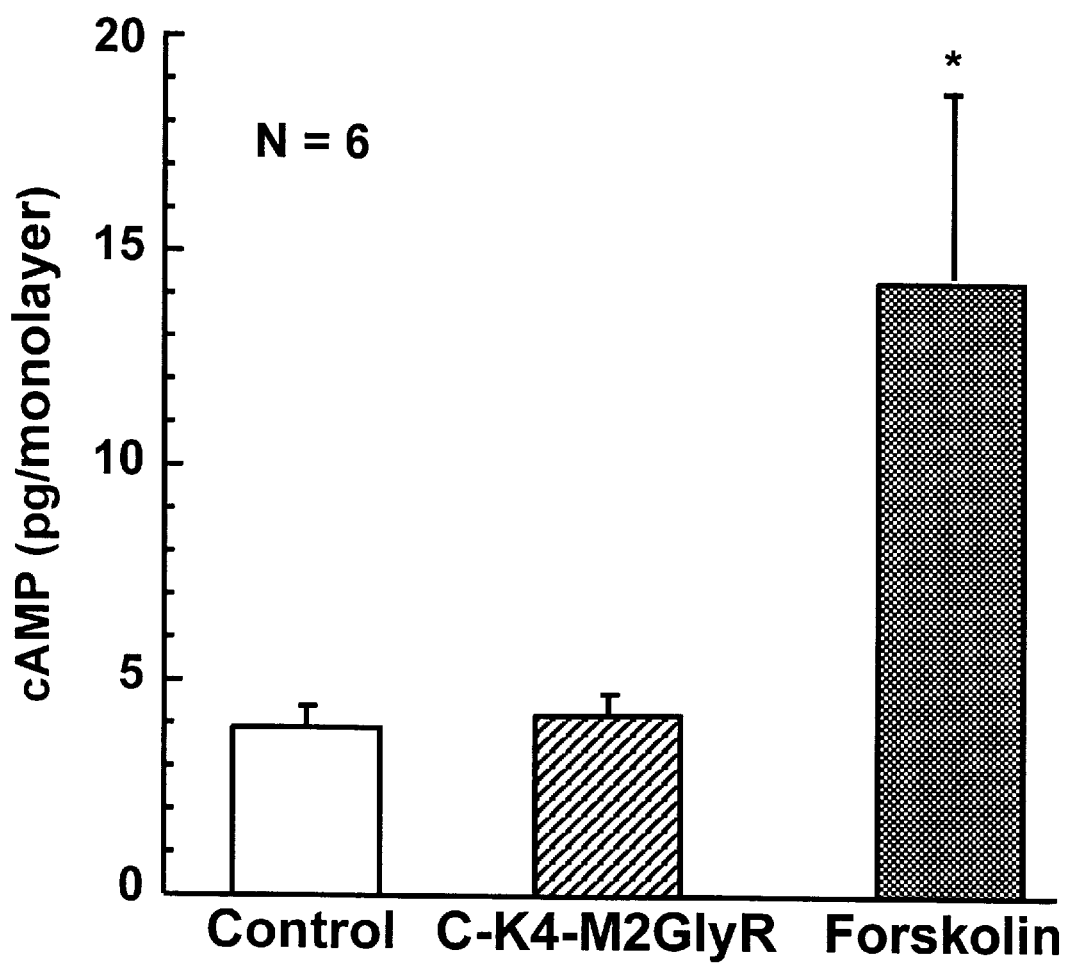
FIG. 9 is a graph illustrating the effect of C-K₄-M2GlyR (SEQ ID NO: 7) and forskolin on cAMP content of MDCK monolayers, wherein the monolayers were exposed to control media, 10 μM basolateral forskolin, or 500 μM C-K₄-M2GlyR (SEQ ID NO: 7) for 2 hours prior to extacting cAMP, and wherein n=6 for each experimental condition and *p<0.0 1.
Figure 11E:
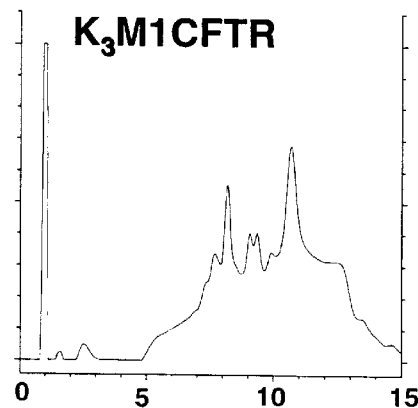
FIG. 11 is a series of seven HPLC chromatographs from a single chemical synthesis in which six lysine residues were sequentially added to the N-terminus of M1CFRT (SEQ ID NO: 25), forming SEQ ID NOS: 25, 26, 27, 28, 29, 30 and 31 from top to bottom and depicting increased solubility correlated with stepwise addition of five lysine residues and beyond.
Figure 11F:
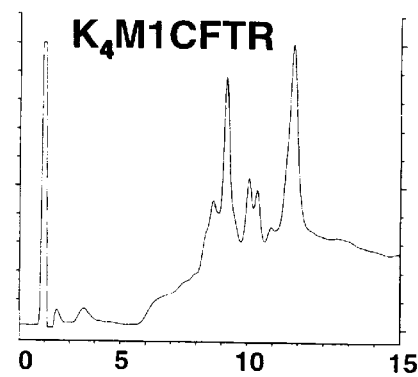
Figure 11G:
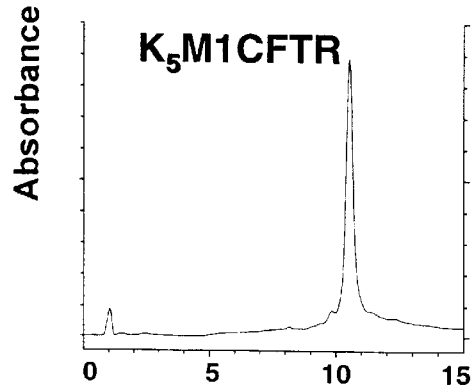
Figure 11H:
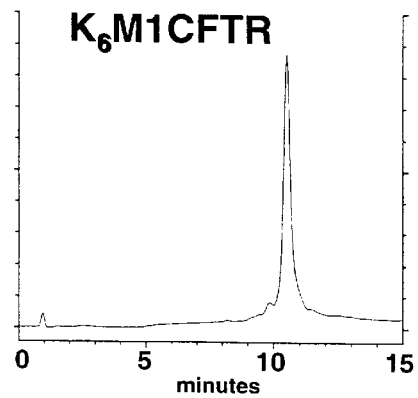

Previously, it was shown that the Cl$^-$ channel inhibitor DPC was effective in blocking the endogenous cAMP-dependent Cl$^-$ channels in MDCK cells (Mangoo-Karim et al.; 1995). Forskolin, an activator of adenylate cyclase, elevates intracellular cAMP and stimulates Cl$^-$ and fluid secretion by these cells (Mangoo-Karim et al., 1995; Neufeld et al.; 1991; Reeves and Andreoli, 1992; Simmons, 1993; Sullivan et al.; 1994). In FIG. 8, the effect of various concentrations of apical DPC on the current induced by C-K$_4$-M2GlyR (SEQ ID NO: 7) was compared with the current stimulated by forskolin. In four monolayers, the concentration of DPC at and above 100 µM significantly inhibited the peptide-generated Isis The fraction of stimulated current remaining after the addition of 100 μM, 1 mM and 3 mM DPC was 68±2%, 41±6% and 26±5%, respectively. In comparison, a dose of 3 mM DPC was required to significantly inhibit of the forskolin-stimulated current (DPC dose response to forskolin-stimulation in MDCK monolayers was previously published) (Mangoo-Karim, et al, 1995). This suggests that the channel formed by C-K$_4$-M2GlyR (SEQ ID NO: 7) is much more sensitive to DPC than the native cAMP-activated Cl⁻ channels. Extracellular Cl⁻ removal. The effect of C-K-M2GlyR (SEQ ID NO: 7) on the electrical properties of MDCK monolayers in the presence and absence of external Cl are summarized in Table 5. Five pairs of monolayers were mounted in Using chambers. Each pair was grown in the same culture plate and under identical growth conditions. The control monolayers were bathed in normal Ringer's solution (119 mM Cl⁻) and the other group was bathed on both sides of the cell layer with a chloride-free Ringer's solution containing cyclamate. In the control monolayers, 100 μM C-K$_4$-M2GlyR (SEQ ID NO: 7) increased $I_{sc}$ by 1.9±0.4 μA/cm², (p<0.01) and hyperpolarized the monolayer by −1.0±0.2 mV (p<0.02). Both $I_{sc}$ and $V_{tc}$ were reduced with basolateral bumetanide. In the zero-Cl⁻ group of monolayers, a negative $I_{sc}$ was recorded. The application of C-K$_4$-M2GlyR (SEQ D NO: 7) failed to stimulate $I_{sc}$ (−0.8±0.3 to −0.8±0.2 μA/cm²) or alter $V_{tc}$ (0.28±0.10 to 0.26±0.10 mV).

Fluid transport. Three groups of 12 MDCK monolayers were grown under identical conditions. The rates of fluid transport by each group were measured after treating the monolayers with control media, 500 μM apical C-K$_4$-M2GlyR (SEQ ID NO: 7) or 10 μM basolateral forskolin for 24 hrs (Table 6). Positive values represent net fluid secretion and negative values indicate fluid absorption. No significant net transport of fluid occurred in the control group (−0.02±0.01 μL/min/cm²). The group of monolayers incubated with 500 μM C-K$_4$-M2GlyR (SEQ ID NO: 7) on the apical surface secreted fluid at a rate of 0.13±0.02 μL/min/cm² (p<0.05). Monolayers stimulated with forskolin (10 pM) secreted fluid at a rate of 0.47±0.05 μL/min/cm² (p<0.001).

In other experiments, the effect of C-K$_4$-M2GlyR (SEQ ID NO: 7) was compared to a scrambled sequence of the peptide, C-K$_4$-SCRAMBLED (SEQ ID NO: 24). Each group contained four monolayers. The rate of fluid transport in the control group was 0.02±0.01 μL/min/cm². Monolayers treated with 500 μM C-K$_4$-M2GlyR (SEQ ID NO: 7) secreted fluid at a rate of 0.15±0.02 μL/min/cm², p<0.01; whereas the rate of fluid transport with the addition of 500 μM C-K$_4$-SCRAMBLED (SEQ ID NO: 24) was not different from the control group (0.02±0.01 μL/min/cm²).

Effect of basolateral C-K$_4$-M2GlyR (SEQ ID NO: 7). During Cl⁻ secretion the directional movement of Cl⁻ from the basolateral to apical media involves the transport of Cl⁻ into the cell across the basolateral membrane and the exit of Cl across the apical membrane. We proposed that the application of C-K$_4$-M2GlyR (SEQ ID NO: 7) to the basolateral surface would reduce Cl⁻ transport by allowing Cl⁻ to cycle across the basolateral membrane. The effect of the basolateral application of C-K$_4$-M2GlyR (SEQ ID NO: 7) was tested on forskolin-stimulated current in five monolayers. Forskolin (10 μM) increased $I_{sc}$ from 0.7+0.5 to 3.5 : 0.9 μ/cm², p<0.001. The addition of 100 μM C-K$_4$M2GlyR (SEQ ID NO: 7) to the basolateral surface of these monolayers reduced this current by 32.71±8.0% (p<0.02) at 40 minutes exposure and 52.6±14.3% (p<0.02) after 80 minutes.

Cyclic adenosine monophosphate measurements. Intracellular cAMP was measured by radioimmunoassay in monolayers treated with either control media, apical C-K$_4$-M2GlyR (SEQ ID NO: 7) or forskolin for 2 hrs. Intracellular cAMP levels in the MDCK cells treated with 500 μM peptide were not different from the level measured in the control monolayers (FIG. 6). In contrast, forskolin (10 μM) increased cAMP levels 266% above the control, confirming previous results (Grantham et al.; 1995).

TABLE 2

Effect of apical application of C—K$_4$-M2GlyR (SEQ ID NO: 7) on the electrical measurements of MDCK monolayers.

|  | $I_{SC}$, μA/cm² | $V_{tc}$, mV | $R_{tc}$, Ohms · cm² |
|---|---|---|---|
| Control | 0.8 ± 0.1 | −1.5 ± 0.4 | 1399 ± 341 |
| 100 μM SEQ ID NO: 7 | 3.3 ± 0.4* | −3.5 ± 0.6* | 1013 ± 171† |

Values are means ± S.E.;
n = 28.
$I_{SC}$, short-circuit current;
$V_{tc}$, transepithelial voltage;
$R_{tc}$, transepithelial resistance.
*comparison to the control period, p < 0.0001.
†p < 0.05.

TABLE 3

Effect of bumetanide on C—K$_4$-M2GlyR-generated (SEQ ID NO: 7) changes in electrical measurements of MDCK monolayers.

|  | $I_{SC}$, μA/cm² | $V_{tc}$, mV | $R_{tc}$, Ohms · cm² |
|---|---|---|---|
| Control | 1.3 ± 0.4 | −3.7 ± 0.9 | 3578 ± 925 |
| 100 μM SEQ ID NO: 7 | 3.2 ± 0.8* | −7.0 ± 1.3* | 2122 ± 386† |
| SEQ ID NO: 7 + 100 μM Bumetanide | 1.4 ± 0.4* | −2.8 ± 0.6* | 2145 ± 474 |

Values are means ± S.E;
n = 8.
C—K$_4$-M2GlyR (SEQ ID NO: 7) was applied to the apical surface; bumetanide was added to the basolateral media.
*comparison to previous period, p < 0.001.
†p < 0.05.

TABLE 4

Effect of chloride channel inhibitors on C—K$_4$-M2GlyR-generated (SEQ ID NO: 7) $I_{SC}$ across MDCK monolayers.

|  | ($I_{SC}$, μA/cm²) | | 100 μM inhibitor |
|---|---|---|---|
|  | control | SEQ ID NO: 7 | (percent change) |
| Niflumic acid, n = 5 | 0.7 ± 0.2 | 3.5 ± 0.2 | −57.1 ± 3.8%* |
| NPPB, n = 7 | 0.6 ± 0.3 | 3.48 ± 0.3 | −55.2 ± 4.5%* |
| DPC, n = 4 | 0.4 ± 0.1 | 2.3 ± 0.4 | −38.0 ± 0.8%* |
| Glibenclamide, n = 6 | 0.6 ± 0.3 | 3.5 ± 0.7 | −18.0 ± 3.1%† |
| DIDS, n = 5 | 0.6 ± 0.3 | 3.5 ± 0.8 | 46.3 ± 18.4%§ |

Various Cl* channel blockers were tested on short-circuit current ($I_{SC}$) generated by the apical application of 100 μM C—K$_4$-M2GlyR (SEQ ID NO: 7).
NPPB, 5-nitro-2-(3-phenylpropylamino)-benzoate;
DPC, diphenylamine-2-carboxylic acid;
DIDS, 4,4'-diisothiocyanostilbene-2,2'-disulfonic acid.
Concentration of the Cl* channel inhibitors was 100 μM (final maximal ethanol concentration, 0.5%). Values for $I_{SC}$ and the percent change in $I_{SC}$ with the addition of the inhibitor are expressed as means ± S.E.;
Negative changes indicate inhibition of the peptide-stimulated $I_{SC}$.
Significance was determined by one sample t test* p < 0.0001,
†p < 0.005,
§not significant.

TABLE 5

Effect of C—K$_4$-M2GlyR (SEQ ID NO: 7) on the electrical properties of MDCK monolayers in the presence and absence of extracellular chloride.

|  | $I_{SC}$, μA/cm$^2$ | $V_{tc}$, mV | $R_{tc}$, Ohms · cm$^2$ |
|---|---|---|---|
| Normal Cl* |  |  |  |
| Control | 0.2 ± 0.3 | −0.1 ± 0.1 | 500 ± 45 |
| 100 μM (SEQ ID NO: 7) | 2.1 ± 0.4* | −1.1 ± 0.2* | 459 ± 25 |
| Zero Cl* |  |  |  |
| Control | −0.8 ± 0.3† | 0.3 ± 0.1† | 417 ± 26§ |
| 100 μM (SEQ ID NO: 7) | −0.8 ± 0.2† | 0.3 ± 0.1† | 422 ± 26§ |

Values are means ± S.E;
n = 5.
Normal chloride concentration was 119 mM. In the zero chloride media, Cl* was replaced with 119 mM cyclamate. C—K$_4$-M2GlyR (SEQ ID NO: 7) was added to the apical media.
*comparison to previous period, p < 0.005.
†comparison to normal Cl* group, p < 0.05.
§not different from the value in normal Cl*.

TABLE 6

Effect of C—K$_4$-M2GlyR (SEQ ID NO: 7) and forskolin on fluid transport by MDCK monolayers.

|  | μL/hr/cm$^2$ |
|---|---|
| Control | −0.02 ± 0.01 |
| 500 μM apical (SEQ ID NO: 7) | 0.13 ± 0.02* |
| 10 μM basolateral forskolin | 0.47 ± 0.05*† |

Transephithelial transport of fluid by Madin-Darby canine kidney (MDCK) cells. Values are means ± S.E.;
n = 12. Positive values indicate the secretion of fluid and nagative numbers indicate fluid absorption. Significance was determined by the Kruskal-Wallis nonparametric ANOVA and Dunn's test.
*comparison to the control period, p < 0.05.
†comparison between the 2 experimental groups, p < 0.05.

Discussion

Peptide Synthesis. The brain glycine receptor is a chloride channel gated by the neurotransmitter, glycine. The second membrane-spanning region of the α-subunit has been predicted to be involved in the channel-forming portion of the receptor (Langosh et al.; 1991). Recent studies have shown that the synthetic peptide that corresponds to the 23 amino acid sequence of this region, M2GlyR (SEQ ID NO: 1), forms an anion-selective channel in lipid bilayers (Reddy et al. 1993). The positively charged arginine residues on the two ends of the peptide determine the anion selectivity of the channel. The anion channel blockers, 9-anthracene carboxylic acid and niflumic acid inhibited the open probability of the synthetic channel formed by M2GlyR (SEQ ID NO: 1). No channel activity could be recorded when Cl$^-$ in the solution was replaced with gluconate (Reddy et al., 1993).

The generation of Cl$^-$ transport by the insertion of extraneous, non-peptide Cl$^-$-conducting pores has been demonstrated. The insertion of the metalloporphyrin Cl$^-$ ionophore, tetraphenyl-21H,23H-porphine manganese (III) chloride, TPPMn(III), into the membrane of cultured mouse and human lung epithelial cells increased anion permeability and increased short-circuit current ($I_{sc}$), results consistent with the secretion of Cl$^-$ (El-Etri and Cuppoletti, 1996).

Epithelial fluid secretion. The mechanisms driving fluid secretion by a variety of secretory epithelia, such as in the trachea, pancreatic duct, salivary gland and the shark rectal gland, have been shown to involve the transepithelial secretion of chloride mediated by the second messenger, cAMP. Cl$^-$ enters the cell via a basolateral Na$^+$/K$^+$/2Cl$^-$ cotransporter, utilizing the electrochemical gradient for Na$^+$ established by the basolateral Na$^+$,K$^+$-ATPase and K$^+$ channels. Cyclic-AMP activated chloride channels on the apical membrane of these cells provide the conductive pathway for Cl$^-$ efflux; and K$^+$ and Na$^+$ exit the cell across the basolateral membrane. The hyperpolarization of the cell caused by the enhanced cycling of K$^+$ across the basolateral membrane augments the force driving the efflux of Cl$^-$ across the apical membrane. The movements of the two ions generate a lumen negative $V_{tc}$ that drives the paracellular movement of Na$^-$. The net addition of Na$^+$ and Cl$^-$ to the lumenal fluid increases the osmotic force causing fluid to be secreted.

MDCK epithelial cells were studied and have been shown to secrete fluid in response to adenylate cyclase agonists, such as forskolin. It was demonstrated that forskolin hyperpolarizes the apically negative $V_{tc}$ and increases a positive $I_{sc}$ in monolayers of MDCK cells. The polarity of the $V_{tc}$ and the direction of the fluid movement indicated that anion secretion was driving the secretion of fluid. The application of ouabain, an inhibitor of the Na$^+$,K$^+$-ATPase, to the basolateral surface blocked fluid secretion (Grantham et al., 1989; Sullivan et al., 1994). Basolateral administration of bumetanide, an inhibitor of the Na$^+$/K$^+$/2Cl$^-$ cotransporter, and apical application of DPC, a Cl$^-$ channel blocker, both inhibited fluid secretion, reduced $I_{sc}$ and depolarized $V_{tc}$ (Mangoo-Karim et al., 1995; Sullivan et al., 1994). These data clearly indicate that fluid secretion by this subculture of MDCK cells is driven by the same types of mechanisms utilized by other secretory epithelia (Liedtke, 1989).

In preliminary experiments, the wild type sequence, M2GlyR (SEQ ID NO: 1), produced interesting effects on anion and fluid transport. 100 μM M2GlyR (SEQ ID NO: 1) applied to the apical surface induced fluid secretion and increased positive $I_{sc}$ (apex to base), consistent with anion secretion. This increase in $I_{sc}$ was inhibited by basolateral bumetanide, apical DPC and the removal of bath Cl$^-$. However, the low water solubility of M2GlyR (SEQ ID NO: 1) limited the dose that could be used and caused aggregation of the peptide in solution leading to inconsistent results. For this reason, modified analogues of the peptide were synthesized to improve solubility while maintaining the channel forming properties. The addition of four to six lysine residues to M2GlyR (SEQ ID NO: 1) greatly improved the solubility of the peptide. The peptide sequence containing four lysine (K) residues attached to the carboxyl-terminus, C-K$_4$-M2GlyR (SEQ ID NO: 7), was selected for this study because of its high solubility (19.6 times the solubility of the wild type) (SEQ ID NO: 1) and reproducible effects.

Effect of C-K$_4$-M2GlyR (SEQ ID NO: 7) on electrical measurements. The application of C-K$_4$-M2GlyR (SEQ ID NO: 7) to the apical surface of MDCK monolayers induced the secretion of fluid, hyperpolarized $V_{tc}$ and increased positive $I_{sc}$ (apex to base). The direction of fluid transport and the increase in positive $I_{sc}$ are consistent with the secretion of an anion. The application of several Cl$^-$ channel inhibitors to the apical surface of these monolayers inhibited the increase in $I_{sc}$ and depolarized $V_{tc}$. The sensitivity sequence was niflumic acid≧NPPB>DPC>glibenclamide>>>DIDS. Niflumic acid and NPPB are very potent inhibitors of epithelial Cl$^-$ channels and produced the greatest reduction in $I_{sc}$ generated by C-K$_4$-M2GlyR (SEQ ID NO: 7). Niflumic acid was also shown to block the conductance obtained by the insertion of the wild type peptide into lipid bilayers (Reddy et al., 1993). These results are consistent with the inhibition of Cl$^-$ channel activitity. Blocking the entry of Cl$^-$ across the basolateral membrane with bumetanide also inhibited the peptide-induced current and depolarized $V_{tc}$ (Table 3). The effect of the peptide on $I_{sc}$ was completely abolished in experiments in which Cl⁻ was removed from the bathing media (Table 4).

Application of C-K$_4$-M2GlyR (SEQ ID NO: 7) to the basolateral surface of the MDCK monolayers reduced forskolin-stimulated $I_{sc}$. These data are also consistent with the formation of Cl⁻ channels, since basolateral channels would tend to promote the efflux of Cl⁻ across the basolateral membrane and reduce the transepithelial movement of Cl⁻.

In the 28 excrements summarized in Table 2, $I_{sc}$ began to increase 13.7±1.3 minutes after the addition of C-K$_4$-M2GlyR (SEQ ID NO: 1). This may represent the minimum time required for the insertion of the peptide into the apical membrane and the assembly of the helices into the tertiary structure of a channel. Data from other experiments indicated that $I_{sc}$ induced by the peptide remained elevated for at least four hours in the presence of the peptide and reversed within two hours after removing the peptide from the bathing solution.

Effect of C-$K_4$-M2GlyR (SEQ ID NO: 7) on fluid secretion. The rate of fluid secretion by MDCK monolayers was initially tested with the addition of 100 $\mu$M C-$K_4$-M2GlyR (SEQ ID NO: 7). The rate of fluid secretion by monolayers exposed to 100 $\mu$M C-$K_4$-M2GlyR (SEQ ID NO: 7)(0.04±0.02, n=8) was significantly different from the control monolayers (−0.03±0.02, n=9, p<0.02), however the magnitude of this rate of transport was very modest. The amount of peptide present in the 200 $\mu$L of media added to the apical surface of the monolayer was only 20 nanomoles, compared to 500 nanomoles in the $I_{sc}$ experiments (5 ml of 100 $\mu$M peptide). The total amount of peptide administered may have been insufficient to adequately treat the surface of the monolayers (surface area=4.71 $cm^2$). Monolayers exposed to 500 $\mu$M apical C-$K_4$-M2GlyR (SEQ ID NO: 7)(100 nanomoles) increased the rate of fluid secretion by 0.15 $\mu l/cm^2/hr$ above the rate of the control monolayers (Table 6). For comparison, monolayers stimulated by 10 $\mu$M basolateral forskolin secreted fluid at a rate of 0.47±0.05 $\mu l/hr/cm^2$, confirming previously reported results (Mangoo-Karim et al., 1995). Several studies have suggested that cAMP may directly stimulate the basolateral $Na^+/K^+/2Cl^-$ cotransporter, the process bringing $Cl^-$ into the cell, in addition to activating the apical $Cl^-$ conductance. This may explain the higher rate of fluid secretion and greater stimulation of the anion current with forskolin.

The apical addition of C-$K_4$-SCRAMBLED (SEQ ID NO: 24), a synthetic peptide consisting of a random sequence of the same amino acid composition as C-$K_4$-M2GlyR (SEQ ID NO: 7), had no effect on $I_{sc}$ and fluid transport. This confirms that the increase in fluid and anion secretion was not simply due to a non-specific effect of the peptide.

These results confirm that the synthetic peptide, C-$K_4$-M2GlyR (SEQ ID NO: 7) spontaneously inserts into the membrane of epithelial cells to generate $Cl^-$ and fluid secretion. Two lines of evidence suggest that the $Cl^-$ secretory pathway induced by the peptide differs in some respects from the pathway activated by adenylate cyclase agonists. First, anion secretion generated by C-$K_4$-M2GlyR (SEQ ID NO: 7) is more sensitive to DPC than secretion stimulated by forskolin. A dose of 100 $\mu$M DPC was sufficient to significantly reduce the peptide-induced current, whereas 3 mM was required to inhibit the forskolin current. Second, cellular cAMP was greatly increased by forskolin, but the levels measured after the addition of the maximal effective dose of C-$K_4$M2GlyR (SEQ ID NO: 7) were not different from the control values. Thus, the endogenous cAMP-dependent $Cl^-$ channels that are activated by forskolin arm not involved in $Cl^-$ secretion generated by the peptide. The application of bumetanide to the basolateral surface inhibited the increase in $Cl^-$ current induced by C-$K_4$-M2GlyR (SEQ ID NO: 7) indicating that the $Cl^-$ entry path across the basolateral membrane is the same as that for cAMP-activated secretion.

In summary, the results of this Example confirm that the synthetic peptide, C-$K_4$-M2GlyR (SEQ ID NO: 7) can spontaneously insert into the membrane of MDCK epithelial cells to form anion channels that are sensitive to several of the known $Cl^-$ channel inhibitors. The application of the peptide to the apical surface of MDCK monolayers induces the transcellular secretion of $Cl^-$ and fluid without activating the cAMP induced pathway. The insertion of exogenous $Cl^-$ channel forming peptides into the apical membranes of epithelial cells of cystic fibrosis patients may aid in restoring the ability of these cells to secrete fluid.

EXAMPLE 13

In this example, the water soluble derivative of M2GlyR (SEQ ID NO: 1) described in Example 12 was tested for bioactivity through measurements of $I_{sc}$, frequency of activity, percent inhibition by the blocking agent bumetanide, and diphenylamine-2-carboxylate (DPC) inhibition.

Peptide Synthesis: All peptides were prepared using Fmoc chemistries on an Applied Biosystems model 431 peptide synthesizer (Perkin Elmer, Norwalk, Conn.) at a synthesis scale of 0.1–0.2 mmole using p-hydroxymethylphenoxymethyl polystyrene (HMP) resin preloaded with the first amino acid and the degree of substitution calculated. For the peptide C-$K_4$-M2GlyR-CO-$NH_2$ (SEQ ID NO: 21) the resin 4-(2', 4'-dimethoxyphenyl-Fmoc-aminomethyl polystyrene (Fmoc-amide resin) was used with the degree of substitution calculated (0.64 mmol/g) (Perkin Elmer, Norwalk, Conn.). All solvents were reagent grade unless otherwise indicated and the protected amino acids are purchased from one or more of the following vendors (Perkin-Elmer, Norwalk, Conn.; Bachem, Torrance, Calif.; Peninsula Laboratories, Belmont, Calif. and Peptides International, Louisville, Ky.). For the sequential N-terminal modifications (N-$K_1$–$K_6$) (SEQ ID NOS: 14–19, respectively), aliquots were removed from a common synthesis of the M2GlyR (SEQ ID NO: 1) and M1CFTR (SEQ ID NO: 25) sequences after each lysine residue was condensed. For the C-terminal modifications separate syntheses had to be performed. All peptides were characterized through automated Edman degradation and MALDI-TOF-MS.

Solubility Studies: Saturated solutions of the crude peptides in Ringer's solution, pH 7.4: OSM=305 ($K_2HPO_4$—2.5 mM; $CaCl_2$—2.0 mM; $MgSO_4$—1.2 mM; Glucose—5 mM; Na-Acetate—5.0 mM; L-Alanine—6 mM; $Na_3$-Citrate—1.0 mM; NaCl—115 mM; Na-Lactate—4.0 mM; n-Butyric acid—0.5 mM; $NaHCO_3$—20 mM; & Raffinose—14.1 mM) were prepared by dissolving increasing amounts of peptide directly in 0.1 mL of the above solution until no more went into solution. Samples were centrifuged for 3 min at 15,000 ×g and the supernatant was analyzed for protein concentration using the Pierce BCA protein assay. With the higher lysine analogs, $K_4$–$K_6$, (SEQ ID NOS: 7, 17, 18, 19 and 21) a clear gel often formed at saturating concentrations. In those cases just enough fluid was added to these solutions to break the gels.

HPLC Studies: Reverse phase HPLC (PLRP-S300; 50×7.5 mm I.D.), with a linear 10 min. gradient from 20–70% acetonitrile in water containing 0.1% trifluoroacetic acid, was used to check for aggregation in the soluble peptide fractions (FIGS. 10 and 11) prepared above. Injection of 10 μL were made and elution from the column was monitored at 215 nm. HPLC purified samples were used for the in vitro assays and biophysical studies. The crude samples were dissolved in water containing 50% acetonitrile. Under these conditions the peptides did not aggregate to any great extent. These purified samples were taken to dryness under vacuum. NMR and CD samples were dissolved in water or $D_2O$ as required.

Bioactivity of modified peptides: We investigated the channel-forming activity of M2GlyR (SEQ ID NO: 1) and the lysine analogs (SEQ ID NOS: 1, 7, 9, 14–21) on monolayers of subtype of Madin-Darby canine kidney, MDCK, cells (Grantham ref) grown on permeable supports (Snapwell, 12 mm dia.; Costar Corp). MDCK monolayers were placed in Using chambers containing 5 mL of Ringer's media in the apical and basolateral compartments. Short circuit current (Isc), transepithelial potential (Vte) and transepithelial resistance (Rte) were monitored prior to and after the addition of the peptide. The unmodified M2GlyR (SEQ ID NO: 1) and the N-K1-M2GlyR (SEQ ID NO: 14) were dissolved in dimethyl sulfoxide, DMSO, due to the low solubility of these peptides in aqueous solutions. The maximal final concentration of DMSO, 1%, was without effect on Isc. More soluble forms of M2GlyR were prepared as 2.5 mM stocks in Ringer's media. In inhibitor experiments, either basolateral bumetanide (100 uM) or apical diphenylamine-2-carboxylic acid (DPC, 3 mM) were added after $I_{sc}$ reached a steady state in the presence of the peptide. The lower solubility forms at their saturating concentrations and all higher solubility analogs at 5 mM. In other experiments after the channels had become fully activated, inhibition of the peptide induced channel activity was checked using either (100 μM) bumetanide (an inhibitor of the $Na^+/K^+/2Cl^-$ cotransporter) or (3 mM) diphenylamine-2-carboxylic acid (DPC), a known Cl- channel blocker.

CD and NMR Studies: Circular dichroism was used to monitor secondary structure of the N-$K_4$-M2GlyR (SEQ ID NO: 17) and the C-$K_4$ M2GlyR (SEQ ID NO: 7) with and without trifluoroethanol in water at 25° C. using a 0.1 mm pathlength cuvette. Spectra were recorded on a Jasco J-710 spectropolarimeter with Neslab RTE-111M circulator. Protein concentrations were determined using the Pierce BCA assay with bovine albumin used as the standard. The data was analyzed using software provided by the manufacturer.

NMR was used to examine aggregation. TOCSY spectra were generated in both $D_2O$ and $D_2O$ containing 30% deuterated TFE for the N-$K_0$-$K_6$ M2GlyR (SEQ ID NOS: 1, 14–19) series and C-$K_4$-M2GlyR (SEQ ID NO: 7). Peptide concentrations of 3 mM were used in these experiments. Spectra were recorded using 500 mHz Varian Utilityplus NMR.

Viscosity measurements: Peptide samples were dissolved in Ringer's solution, pH7.4, or water at the indicated concentrations to a final volume of 4.0 mL. Samples were vortexed for 150 seconds, centrifuged at 4000×g for 1 min, transferred to an Ostwald 100 viscometer immersed in a 37° C. circulating water bath and allowed to come up to temperature. The first time point was usually recorded at about t=10 min. At each incubation point, three readings were taken. In those experiments in which sheer was observed three time points were taken but the first value was used for the viscosity calculation. The aggregated peptides were analyzed by SDS-PAGE using 8% acrylamide gels. Aggregated samples (200 ng) were incubated with a loading buffer containing 4% SDS for five minutes prior to layering in the gel lanes. Heating was omitted because boiling had been shown to completely disrupt the aggregate. The protein bands were visualized using silver stain.

Several families of peptides (SEQ ID NOS: 7–21) based on the M2GlyR (SEQ ID NO: 1) and the M1CFTR sequences (SEQ ID NOS: 25–31) (Table 7) were prepared. The M2GlyR (SEQ ID NO: 1) sequence is classified as a channel-forming amphipathic helical segment while the M1CFTR (SEQ ID NO: 25) sequence is comprised almost exclusively of hydrophobic residues considered to be more typical of a transmembrane sequence. The M1CFTR (SEQ ID NO: 25) peptide associates with membranes but does not appear to form an ionic conducting channel such as M2GlyR (SEQ ID NO: 1) (Montal et al. 1994 ). The low intrinsic solubilities of the two unmodified transmembrane segments 1.4 mM for M2GlyR (SEQ ID NO: 1) and 0.26 mM for M1CFTR (SEQ ID NO: 25) in Ringer's solution, reflects their membrane origin. The amphipathic sequence, M2GlyR (SEQ ID NO: 1), has a higher hydrophobic moment and is somewhat more soluble than M1CFTR (SEQ ID NO: 25). Modifications that yielded net charges of ≦+3 at the N-terminus of M2GlyR (SEQ ID NO: 1) and ≦+6 at the N-terminus of M1CFTR (SEQ ID NO: 25) did not significantly improve the aqueous solubility of the sequence. The complete removal of charge from the N-terminus of M2GlyR (SEQ ID NO: 1) did not alter the solubility either. Reverse-phase HPLC, SDS-PAGE and TOCSY-NMR confirmed that these soluble samples are indeed comprised of aggregated peptide. The HPLC profiles for the M2GlyR (SEQ ID NO: 1) and M1CFTR (SEQ ID NO: 25) series are shown in the first panel of FIGS. 10 and 11, respectively. Aggregated peptides appear as multiple broad peaks that elute by an organic mobile phase over a wide range. Matrix-assisted laser desorption ionization, time of flight mass spectral analysis (MALDI-TOF-MS) of each peak reveals only the mass of the monomer. In SDS-PAGE studies the samples are treated with SDS but not heated. Several discrete bands between 40–60 kDa were observed. Boiling in SDS reduced the aggregates back to the monomer state (data not shown). With TOCSY-NMR, these samples yielded many poorly resolved and overlapping signals.

The incorporation of additional positive charges to the ends of these sequences does affect solubility. Solubility increases due to the addition of the third lysine for M2GlyR (SEQ ID NO: 16) (4.8 fold) and the fifth lysine for M1CFTR (SEQ ID NO: 18) (34 fold) appear cooperative in nature (FIG. 12). In addition to the increased solubility afforded by the incorporation of lysines at the N-terminus of the amphipathic sequence, the degree of aggregation present in the HPLC profiles, decreases (FIG. 10). The transition from aggregates to apparent monomer for the amphipathic peptide occurs gradually over the addition of N-$K_1$-$K_4$ (SEQ ID NOS: 14–17). The tracings for N-$K_4$-$K_6$ (SEQ ID NOS: 17–19) are superimposable. For the non-amphipathic M1CFTR N-$K_1$-$K_6$ (SEQ ID NOS: 25–31) series the increase in solubility (FIG. 12) and the reduction in aggregation (FIG. 10) occurred in a more dramatic fashion. Solubility and stabilization of the monomer occurred only upon addition of the fifth lysine (SEQ ID NO: 30).

To confirm the presence of the monomeric forms for the soluble peptides TOCSY-NMR was used. Base on the HPLC tracings it seemed reasonable to expect that N-$K_3$ through N-$K_6$-M2GlyR (SEQ ID NOS: 16–19) would all be monomeric. However the TOCSY-NMR spectra for the sequences qualitatively revealed different levels of aggregation with N-K$_3$ (SEQ ID NO: 16) appearing as aggregated as N-K$_1$ (SEQ ID NO: 14) and N-K$_2$ (SEQ ID NO: 15), N-K$_4$ (SEQ ID NO: 17) appearing to be a mostly monomer and K$_5$ and K$_4$ (SEQ ID NOS: 16–17) being judged to be essentially monomeric. Three spectra recorded using N-K$_0$(SEQ ID NO: 1), N-K$_3$ (SEQ ID NO: 16) and N-K$_5$-M2GlyR (SEQ ID NO: 18) are shown in FIG. 14. N-K$_4$-M2GlyR (SEQ ID NO: 17) gave a spectra that indicated the presence of both aggregated and monomeric forms (not shown).

Selected modifications at the C-terminus were also studied (Table 7). Not all of the C-terminal analogs of the N-terminal series were prepared due to the prohibitive cost. This C-terminal series added 2 to 4 positive charges. The effect of adding positive charge at the C-terminus was much more dramatic than that observed for the N-terminus (FIG. 13). The wild type sequence with its free C-terminus was used for the −1 net charge values for the C-terminal modification. Since no 0 or +1 C-terminal adduct was prepared the data points for −1 and +2 were not connected. The C-K$_3$ adduct (SEQ ID NO: 20) which has only a +2 charge due to the presence of the free carboxy-terminus, has a solubility equivalent to that seen for the +4 N-terminal adduct, N-K$_3$ (SEQ ID NO: 16), but less than that seen for N-K$_4$ (SEQ ID NO: 17). Placing 4 lysines at the C-terminus yields a net terminal charge of +3 at neutral pH whereas placing them at the N-terminus it generates a +5 charge. The paradox here, in which less charge at the C-terminus yields a peptide that is 2× more soluble is an important observation, suggesting that there is a site closer to the C-terminus that somehow influences the overall solubility of the peptide. The C-K$_4$ peptide (SEQ ID NO: 7) in fact had a solubility in excess of that seen for the +7 N-terminal adduct N-K$_6$ (SEQ ID NO: 19). The C-terminal +4 species (SEQ ID NO: 21) was generated by synthesizing the C-K$_4$ peptide (SEQ ID NO: 7) on a resin that generated the carboxamide at the C-terminus thus neutralizing the negative charge. This peptide was extremely soluble achieving 158 mg/mL (56.1 mM). This solubility represented a 40 fold increase in solubility over the non-modified peptide. TOCSY-NMR revealed that only the C-K$_4$ (SEQ ID NO: 7) and the C-K$_4$—CO—NH$_2$ (SEQ ID NO: 21) were predominantly monomeric. These results clearly indicate a positional effect for the added charge. Modifications at the C-terminus yielded substantially larger increases in solubility per unit added positive charge (FIG. 13).

Solubility studies were also performed on the Met14Cys mutant (SEQ ID NO: 8) which was also blocked at both termini. This mutant was eight times more soluble than the wildtype sequence. The HPLC profile of the saturated solution (not shown) was similar to that seen for the N-K$_3$ adduct (SEQ ID NO: 16) indicating the absence of large aggregates. The significance of this mutation will be discussed later.

Channel-forming activity of the modified N-K$_n$-M2GlyR sequences (SEQ ID NOS: 1, 14–19) was assessed using a subtype of Madin-Darby Canine Kidney (MDCK) cells. These cells were grown to confluent monolayers on permeable membranes. The monolayers were inserted into Ussing chambers and the applied external current required to drive the negative transepithelial potential difference to zero (short circuit current, $I_{sc}$) was measured as set forth in Example 12. The opening of native anion channels in the apical membrane of the cells or the insertion of foreign, anion channel-forming peptides results in an increase in positive current flow from the apical to the basolateral surface of these monolayers (Mangoo-Karim et al).

Because of its low solubility in aqueous media, the unmodified M2GlyR (SEQ ID NO: 1) was dissolved in dimethyl sulfoxide (DMSO). This solution was added to the medium bathing the apical surface of the monolayers in amounts that achieved a final concentration of 100 $\mu$M peptide and 1% DMSO. Even with the inclusion of organic solvents in the bathing solutions, an increase in $I_{sc}$ was recorded in only 65% of the monolayers tested. On the occasions that the wild type M2GlyR (SEQ ID NO: 1) produced reliable electrophysiological changes (Table 8), a reasonable increase in $I_{sc}$ occurred. This stimulated $I_{sc}$ was inhibited by the Na-K-Cl cotransporter blocker, bumetanide, applied to the basolateral surface and by the chloride channel blocker, diphenylamine-2-carboxylate (DPC) applied to the apical surface. These combined electro and pharmacological effects were deemed to be wild type activity and served as the standard for evaluating the modified sequences.

Peptide containing the addition of the 1, 2 or 3 lysines to the N-terminus (SEQ ID NOS: 14–16) had little channel-forming activity, however the addition of lysines 4, 5 and 6 (SEQ ID NOS: 17–19) exerted a dramatic effect. The frequency of producing chloride channel activity improved to a point that every experiment yielded increases in the short circuit current.

Comparing the channel activity of the wild type sequence (SEQ ID NO: 1) to that of the N-$K_4$ (SEQ ID NO: 17) revealed a substantial increase in the short-circuit current over that of unmodified M2GlyR (SEQ ID NO: 1) when applied at the same concentration. The modified wild type N-$K_4$-N-$K_6$ (SEQ ID NOS: 17–19) were tested for their response to bumetanide and DPC. As shown in the Table 8, the N-$K_4$ (SEQ ID NO: .17) was the only N-terminal modification that completely retained the pharmacological characteristics demonstrated by the unmodified M2GlyR peptide (SEQ ID NO: 1). The N-$K_4$ channel assembly (SEQ ID NO: 17) was inhibited when either chloride was omitted from the media (data not shown) or limited in the presence of bumetanide or the channel was directly blocked by DPC. The highly soluble N-$K_5$ (SEQ ID NO: 18) and N-$K_6$-M2GlyR (SEQ ID NO: 19) while yielding increased short circuit currents failed to respond appropriately in the presence of the two inhibitors. The N-$K_5$ (SEQ ID NO, 18) and N-$K_6$ (SEQ ID NO: 19) channel assemblies showed little inhibition when bumetanide was added suggesting that chloride selectivity may have been lost.

Channel forming activities for C-$K_3$ (SEQ ID NO: 20), C-$K_4$ (SEQ ID NO: 7) and C-$K_4$—CO—$NH_2$(SEQ ID NO: 21)analogs were also performed. Though soluble, C-$K_3$ (SEQ ID NO: 20) appeared aggregated by multi-dimensional TOCSY-NMR and had activity in the $i_{sc}$ experiment The C-$K_4$ analog (SEQ ID NO: 7), which was more soluble than the +7 charged N-$K_4$-M2GlyR sequence (SEQ ID NO: 19). The C-$K_4$—CO—$NH_2$ (SEQ ID NO: 21) which had the highest solubility of any of the M2GlyR adducts displayed lower activity which suggests that this form of the sequence has decreased affinity for the membrane. With regard to the parameters set out in Table 8 only C-$K_4$-M2GlyR (SEQ ID NO: 7) gave a substantial increase in $I_{sc}$ while retaining a near normal response to bumetanide and DPC.

One interesting mutation sequence met14cys (SEQ ID NO: 8) was also analyzed for activity and inhibition in the presence of bumetanide and DPC. These results ***.

For the in vitro assay controls two different scrambled M2GlyR sequences (SEQ ID NOS: 22–24) were generated, type I and type II (Table 7). The high content of beta structure promoting amino acid residues such as ile, val, gln, met and thr suggest that a stable beta structure might be formed. Type I was modeled such that beta-structure would be maximized and type II such that beta-structure would be minimized. In both cases any amphipathic structure was minimized as well. Upon standing at room temperature for about 30 min., the type I N-K$_4$-scrambled peptide (SEQ ID NO: 22) began to precipitate out of solution. The type II sequence (SEQ ID NO: 24) was much more soluble, 3.7 mM in Ringer's for the N-K$_4$-type I scrambled (SEQ ID NO: 23) compared to 88 mM for the C-K$_4$-type II scrambled (SEQ ID NO: 24).

The N-K$_5$-M1CFTR (SEQ ID NO: 30) (100 mM) peptide was also tested on MDCK cells and stimulated I$_{sc}$ by only 0.4 mA/cm$^2$ (N=2). Addition of the five lysines to M1CFTR (SEQ ID NO: 30), a sequence that previously had been shown to be unable to form channels has gained channel-forming activity with the lysine additions.

The sequences C-K$_4$-M2GlyR(SEQ ID NO: 7) and N-K$_4$-M2GlyR (SEQ ID NO: 17) were tested in fluid secretion experiments with incubations in aqueous buffer for 24 hr (see Example 12). C-K$_4$-M2GlyR (SEQ ID NO: 7) gave the most consistent and highest rates for water secretion by epithelial monolayers.

Figure 15A:
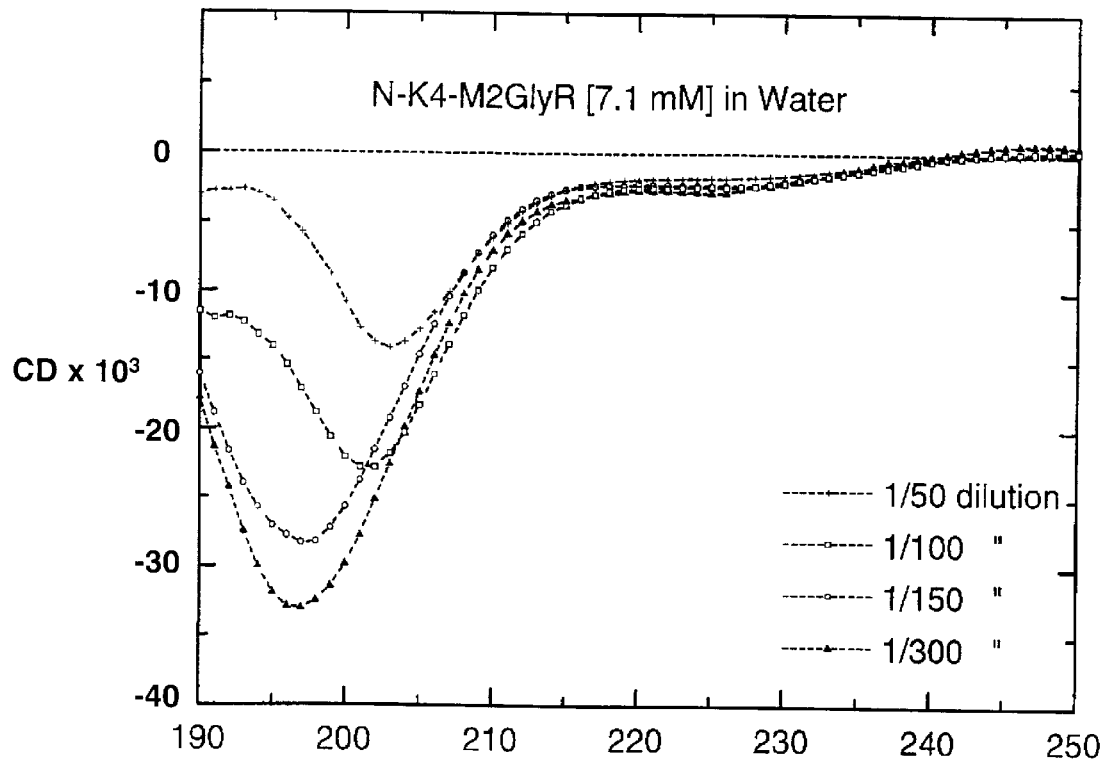
FIG. 15 is a series of two CD spectra for SEQ ID NOS: 17 and 7 from top to bottom in water at several dilutions.
Figure 15B:
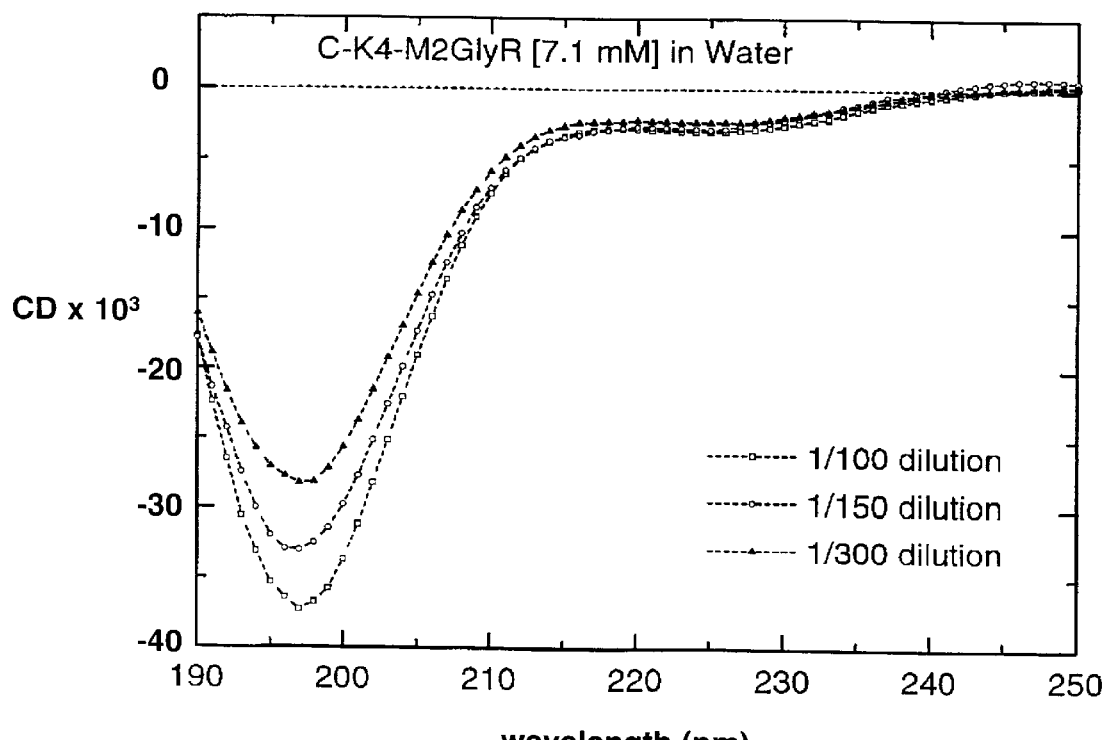
Figure 16:
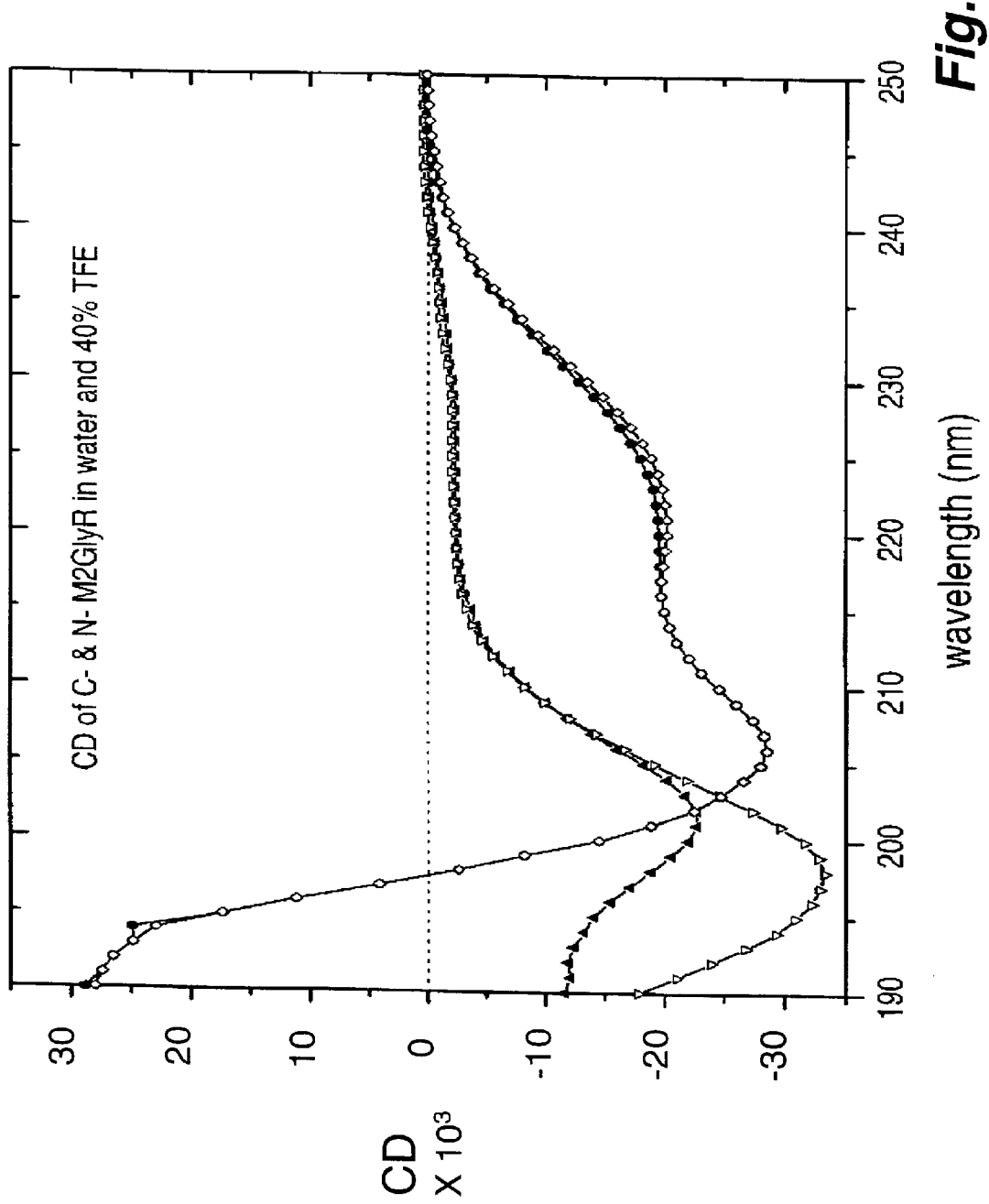
FIG. 16 is a CD spectrum of SEQ ID NOS: 17 and 7 in water and 40% trifluoroethanol (marked on the drawing as 17W and 7W for the water spectra and 17T and 7T for the trifluoroethanol spectra), showing that in trifluoroethanol, the peptides have similar structure.

Circular dichroism studies examining the secondary structure of N-K$_4$(SEQ ID NO: 17) and C-K$_4$ (SEQ ID NO: 7) were carried out. CD spectra were produced for dilute solutions of N-K$_4$ and C-K$_4$ (SEQ ID NOS: 7 and 17) in water (FIG. 15). The concentrations of the peptide employed for CD overlap the concentrations that produce increases in I$_{sc}$. The CD spectra reveal random coil for both at these active peptides. At increasing concentrations the N-K$_4$ adduct (SEQ ID NO: 17) shows what appears to be a shift toward formation of a-helix. No such concentration dependent structural change was observed with the C-K$_4$ (SEQ ID NO: 7). Helicity was induced by the addition of 40% trifluoroethanol (FIG. 16). At this TFE concentration the two peptides formed about the same amount of helix, estimated to be 60% based mean-residue elipticity at 222 nm (Chen et al. 1974).

Figure 17:
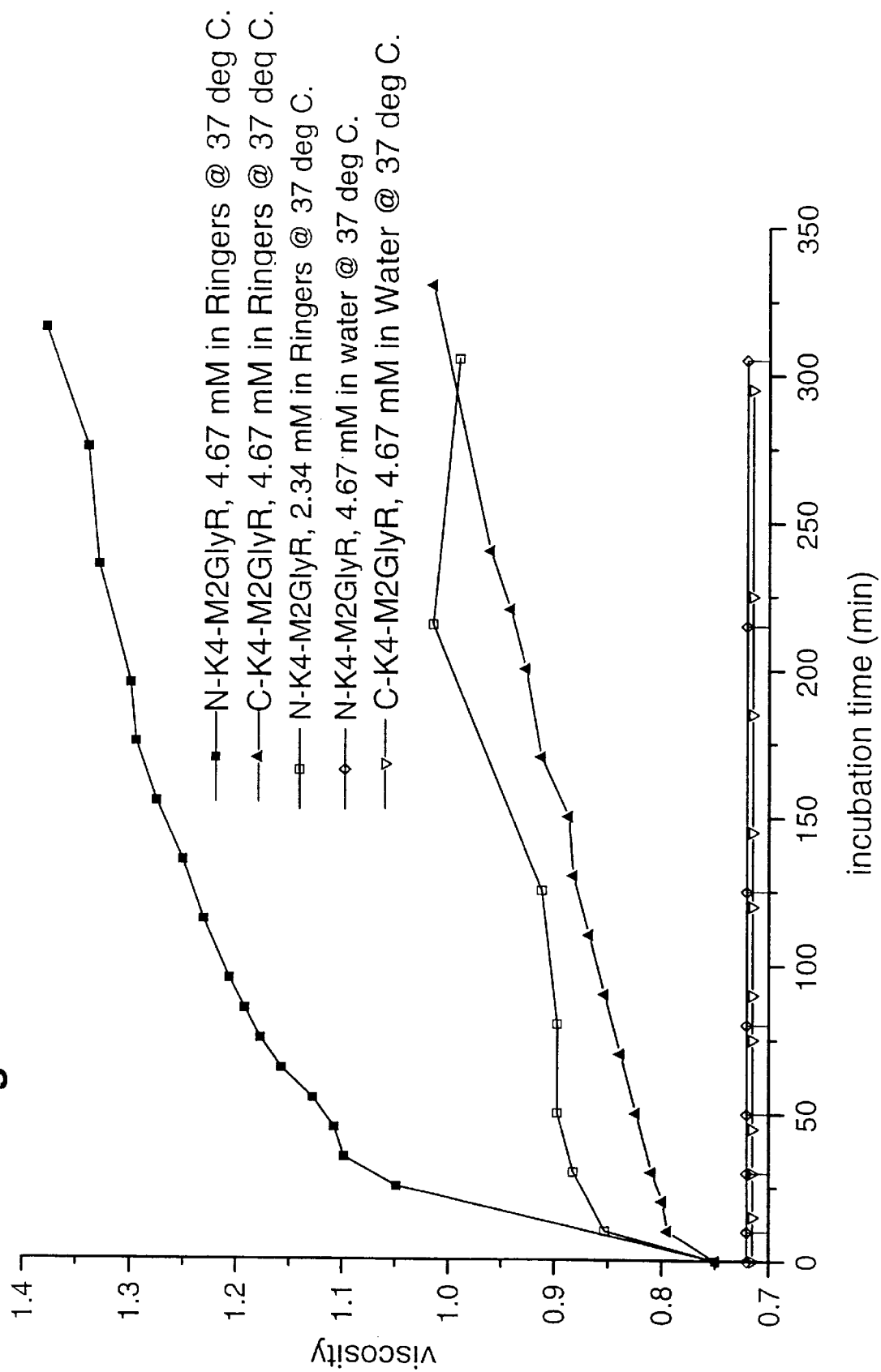
FIG. 17 is a graph showing the increase in viscosity versus incubation time for a series of sequences (SEQ ID NOS: 17 and 7) at two concentrations in Ringers solution and water.

The effects of the Ringer's media were tested by monitoring viscosity on C-K$_4$-M2GlyR (SEQ ID NO: 7) and N-K$_4$-M2GlyR (SEQ ID NO: 17). The time dependence on aggregation in Ringer's, at pH 7.4 and water is shown (FIG. 17). In water no aggregation is observed for either C-K$_4$-M2GlyR(SEQ ID NO: 7) or N-K$_4$-M2GlyR (SEQ ID NO: 17). However very different modes of aggregation are seen for C-K$_4$-M2GlyR (SEQ ID NO: 7) and N-K$_4$-M2GlyR (SEQ ID NO: 17) at 4.67 mM. At this concentration readily measurable rates are observed. C-K$_4$-M2GlyR (SEQ ID NO: 7) aggregation is best fit to a first order reaction while N-K$_4$-M2GlyR (SEQ ID NO: 17) is second order. At 2.33 mM N-K$_4$-M2GlyR (SEQ ID NO: 17) aggregates at a four fold slower rate. One experiment was performed that included 40% TFE along with the Ringers to test the rate of aggregation of helical segments as opposed to the random coils seen for Ringers alone.

These results suggested that Ringers stock solutions be prepared just before use and at the lowest possible concentration. In water, stock solutions of high concentration should be stable with regard to aggregation.

TABLE 7

Solubility Properties of Test Sequences

| SEQ ID NO: | Charge | mg Peptide/mL Ringers Solution | Concentration (mM) | Peptide MW |
|---|---|---|---|---|
| 7 | 1 | 3.3 | 1.4 | 2305 |
| 10 | 0 | 3.4 | 1.4 | 2353 |
| 11 | 1 | 4.1 | 1.68 | 2439 |
| 12 | 2 | 4.1 | 1.7 | 2391 |
| 13 | 3 | 4.3 | 1.7 | 2519 |
| 14 | 2 | 4.1 | 1.7 | 2433 |
| 15 | 3 | 6.9 | 2.3 | 2561 |
| 16 | 4 | 29.8 | 11.1 | 2689 |
| 17 | 5 | 37.8 | 13.4 | 3817 |
| 18 | 6 | 46.4 | 15.8 | 2946 |
| 19 | 7 | 64.9 | 21.1 | 3074 |
| 20 | 2 | 27.2 | 10.1 | 2689 |
| 7 | 3 | 77.8 | 27.5 | 2817 |
| 21 | 4 | 158 | 56.1 | 2815 |
| 8 | 0 | 25.5 | 11.0 | 2318 |
| 22 | 1 | 8.2 | 3.5 | 2305 |
| 23 | 5 | 10.3 | 3.7 | 2817 |
| 24 | 3 | 248.9 | 88 | 2817 |
| 25 | 2 | 0.69 | 0.263 | 2620 |
| 26 | 3 | 0.73 | 0.266 | 2748 |
| 27 | 4 | 0.73 | 0.25 | 2876 |
| 28 | 5 | 0.92 | 0.306 | 3004 |
| 29 | 6 | 1 | 0.319 | 3132 |
| 30 | 7 | 38.8 | 11.9 | 3260 |
| 31 | 8 | 72.1 | 21.3 | 3389 |

TABLE 8

Physiological Effects of Test Sequences

| SEQ ID NO: | Frequency of Activity | Isc Increase $\mu$A/cm$^2$ | Bumetanide % Inhibition | DPC % Inhibition |
|---|---|---|---|---|
| 1 | 65% (N = 37)[1] | 1.0 $\mu$A/cm2 (N = 24) | 100 (5/5)[2] | 100 (5/5) |
| 14 | 42% (N = 12) | 0.3 $\mu$A/cm2 (N = 5) | 100 (3/3) | 100 (2/2) |
| 15 | <10% | <1.0 $\mu$A/cm2 | N.A. | N.A. |
| 16 | 63% (N = 8) | 0.7 $\mu$A/cm2 (N = 5) | 44 (3/4) | 83 (3/3) |
| 17 | 97% (N = 58) | 1.2 $\mu$A/cm2 (N = 560) | 69 (27/29) | 97 (5/5) |
| 18 | 100% (N = 13) | 2.3 $\mu$A/cm2 (N = 13) | 37 (4/5) | 22 (5/6) |
| 19 | 100% (N = 10) | 3.3 (N = 10) | 10 (3/5) | 22 (4/5) |
| 20 | 91% (N = 11) | 1.0 (N = 10) | 99 (4/4) | 61 (5/6) |
| 7 | 100% (N = 94) | 2.7 (N = 94) | 77 (31/31) | 93 (5/5) |
| 21 | 100% (N = 14) | 1.2 (N = 14) | 99 (6/6) | 77 (5/5) |
| 8 | 25% (N = 4) | 0.25 (N = 1) | 100 (1/1) | — |

[1] equals number of membranes tested
[2] Number of membranes responding divided by number of membranes tested Discussion Example 12 suggested that the C-K$_4$-M2GlyR peptide (SEQ ID NO: 7) forms anion selective channels. Attempts to use the wild-type M2GlyR sequence (SEQ ID NO: 1) demonstrated a relatively low efficiency of incorporation from the aqueous solutions used in the electrophysiological experiments. Lysine residues were added one at a time to see when enough electrostatic charge was added to promote chain repulsion (monomers) compared to the hydrophobic attraction (aggregate) seen for M2GlyR (SEQ ID NO: 1).

Twenty-five separate peptides were synthesized and analyzed with regard to their aqueous solubility, degree of aggregation in water and bioactivity. The complete removal of charge from the N-terminus of M2GlyR did not alter the solubility, suggesting that the amphipathic character of the segment is driving its limited solubilization. If this is the case it would be expected that the peptides would form micelles in aqueous solvent with the hydrophobic faces of the helices clustering together to form an interior core and the hydrophilic faces directed out into solvent. The structurally analogous δ-toxin has been shown to form aqueous aggregates comprised of about 70 molecules (Kantor et al. 1972) and the alanine substituted prolyl$_{14}$-melittin formed aggregates containing about 50 molecules (John and Jähnig 1992). The hydrophobic surfaces of the peptide, that would be predicted to drive the membrane association, are made less accessible through their own self association (Fattal and Ben-Shaul 1993, Patro and Przybycien 1994).

Addition of lysines at the N-terminus of M2GlyR (SEQ ID NO: 1) increased solubility and decreased aggregation as judged by HPLC and TOCSY-NMR. Addition of the third lysine led to a cooperative effect that greatly enhanced solubility. The N-K$_3$ peptide (SEQ ID NO: 16) appeared to be monomeric by HPLC yet this fraction appeared aggregated by NMR and failed to reliably produce ion channels. These results revealed that HPLC profiles are not sensitive for detecting smaller aggregates. HPLC has previously been used to judge the amphipathic character of melittin deletion peptides (Blondelle and Houghton; 1991). By examining the resolution of the individual TOCSY resonances one can better estimate aggregation. Peptides N-K$_4$ through N-K$_6$ (SEQ ID NOS: 17–19) were highly soluble, contained differing percentages of monomer in water and always produced an increase in short circuit current (Isc). N-K$_4$-M2GlyR (SEQ ID NO: 17) was shown by NMR to be a mixture of monomer and aggregate. These two forms of the peptide must establish an equilibrium and if monomer is removed from the system by virtue of its membrane association into the membrane the equilibrium should be shifted toward monomer. This model suggests that in the case of N-K$_{0-3}$-M2GlyR (SEQ ID NOS: 1, 14–16) few monomers exist, otherwise activity would have been observed more often. The frequency of activity observed for the N-K$_4$-M2GlyR (SEQ ID NO: 17) channel was higher than that for the wild-type sequence. We ascribe the N-K$_4$-M2GlyR (SEQ ID NO: 17) activity to an increase in number of channels that form in the membrane as a direct consequence of having greatly increased monomer concentrations.

Only N-K$_4$ (SEQ ID NO: 17) was able to fully match the wild type sequence in terms of inhibition by DPC and bumetanide. The wild type sequence forms predominantly a five-helix bundle (Reddy et al.; 1993) and N-K$_4$ (SEQ ID NO: 17) appears to adopt that same geometry based on the physiological properties. In the case of N-K$_5$ (SEQ ID NO: 18) and N-K$_6$ (SEQ ID NO: 19) their still larger currents and lack of inhibition by bumetanide suggests a larger pore due most likely to a larger helical bundle ($\geq 6$). Increased pore size affects selectivity and the size of the ion that will pass.

The successful solubilization of the non-amphipathic M1CFTR sequence (SEQ ID NOS: 25–31) points to the general nature of this procedure. Most types of transmembrane sequences could be made soluble in aqueous buffers The major difference between the solubilization of M1CFTR (SEQ ID NO: 25) and M2GlyR (SEQ ID NO: 1) through the addition of lysine residues is the transition between insoluble and soluble forms. The solubility of M2GlyR (SEQ ID NO: 1) gradually increases up to the addition of the third lysine with a gradual decrease in the complexity of the HPLC elution pattern. The solubility of M1CFTR (SEQ ID NO: 25) however changes little through the addition of the fourth lysine, improving from 0.26 mM to only 0.32 mM. With the addition of the fifth lysine (SEQ ID NO: 30) a 37 fold increase in solubility is seen over that of the K-4 adduct (SEQ ID NO: 29). An equally dramatic shift in the HPLC elution pattern is seen. Since no TOSCY-NMR spectra were recorded for either N-K$_5$ (SEQ ID NO: 30) or N-K$_6$-M1CFTR (SEQ ID NO: 31) it is unclear whether the single peak seen in the HPLC represents monomer, small aggregates or both. Addition of the fifth lysine (SEQ ID NO: 30) does however produce a peptide that produces ion conducting channels suggesting the presence of monomers. Small increases in I$_{sc}$ were observed when this peptide was exposed to MDCK monolayers. No such channels were observed for the unmodified peptide (SEQ ID NO: 25) (Montal et al.; 1994) suggesting that the lysines may help the helices pack with a geometry more favorable for ionic conducting activity. Because of this new observed activity this sequence was deemed unsuitable to act as a control sequence and the scrambled sequences of the M2GlyR sequence (SEQ ID NO: 1) were used (SEQ ID NOS: 22–24).

Figure 18:
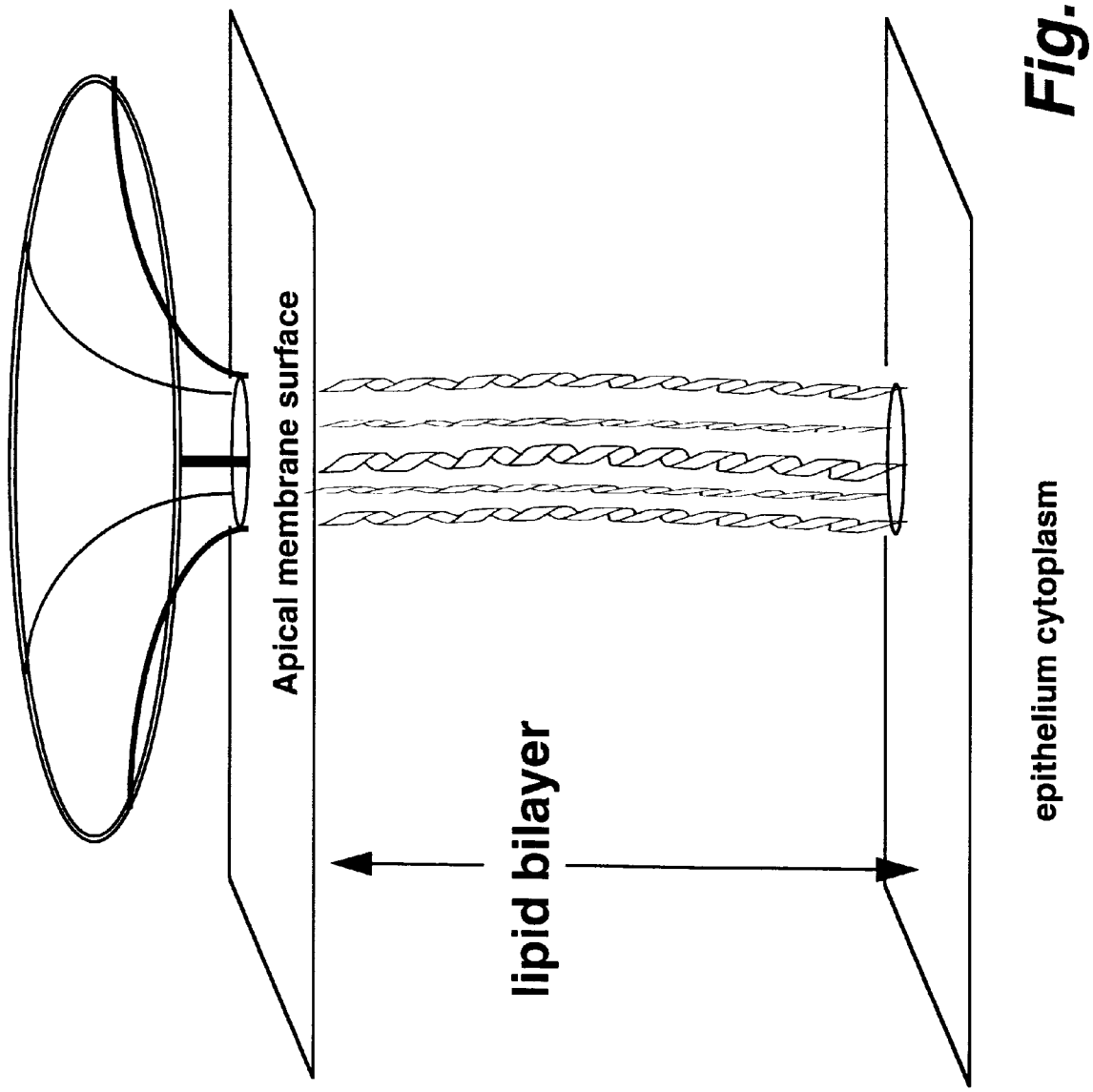
FIG. 18 is a schematic drawing of a representative channel assembly comprised of five helical peptides within a lipid bilayer.

Amphipathic peptides, which are generally monomeric and helical in organic solvents such as acetonitrile, trifluoroethanol or hexafluoroisopropanol (Iwamoto et al. 1994), aggregate when applied to an aqueous solution. Since most of the hydrophobic residues are sequestered in the aggregated state there is little opportunity for them to interact with and insert into membranes. Based on the earlier [Ala 14]-melittin work of Dempsey and co-worker (Dempsey et al. 1991, Dempsey 1992) none of these peptides should form channels due to electrostatic repulsion. As observed in CD the N-K4-M2GlyR sequence (SEQ ID NO: 17) is able to assume a helical structure in TFE and without the assistance of a proline hinge, readily form functional channels. We hypothesize that the lysine tails of the peptide bundles fan out on the surface of the phospholipid in a radial array like the petals of a flower due to electrostatic repulsion of the lysine tails. Others (Beschiaschvili and Bacueler 1991) measured the net charge on melittin bound to POPC vesicles using $^{31}$P NMR and found that they possess a net charge of +1.5, compared to the expected +5–+6. They cite other examples of this phenomenon and suggest that if the ionized groups are greater an 6–7 Å from the lipid the effective charge that the phospholipids experience would be reduced to a value close to that measured. Taking this factor into account we have modeled a five-helix bundle of the C-K$_4$ (SEQ ID NO: 7) or N-K$_4$ (SEQ ID NO: 17) bundle as shown in FIG. 18.

The non-equivalence of placing the same net charges at the C-terminus versus the N-terminus suggest that the peptide is asymmetric in one or more properties. The stabilization of helix dipoles by placement of positive charge at the C-terminus probably contributes little to the solubilization. CD of the N-K, (SEQ ID NO: 17) and C-K$_4$-M2GlyR (SEQ ID NO: 7) show them to be unstructured at concentrations where melittin has formed a four-helix tetramer (Wilcox and Eisenberg; 1992). The peptides appear to aggregate through a short stretch of sequence located near to the C-terminus. Based on a commercial Chou-Fasman prediction program, the sequence TMTTQ, located 13 residues in from the N-terminus and 7 from the C-terminus in the M2GlyR peptide (SEQ ID NO: 1), prefers an extended β-sheet conformation. It is believed that such a patch of amino acids could serve as a nucleation point for the aggregation process and by placing sufficient positive charge nearby, electrostatic repulsion would prevent this association. The solubility increase observed when the methionine residue is substituted by cysteine (SEQ ID NO: 8) supports this hypothesis. The presence of cysteine in that position reduced the beta forming potential of the peptide and only small aggregates form. It is believed that if the TMFTQ sequence is placed closer to the N-terminus, fewer lysines will need to be added to N-Kn adducts (SEQ ID NO: 14–19) to produce a more soluble, less aggregated peptide.

Finally with regard to activity, all peptide solutions that appear to contain some monomeric peptide, show activity. The presence of well resolved NMR-TOCSY signals that could be assigned to all residues correlated well with channel forming activity where as the HPLC profiles were not as precise. Not all active channels however were identical. The three sequences, N-$K_4$, C-$K_4$ and C-$K_4$—CO—$NH_2$ (SEQ ID NOS: 17, 7 and 21), because of their solubility and activity properties, appear to be optimum sequences for therapeutic uses.

EXAMPLE 14

Figure 19:
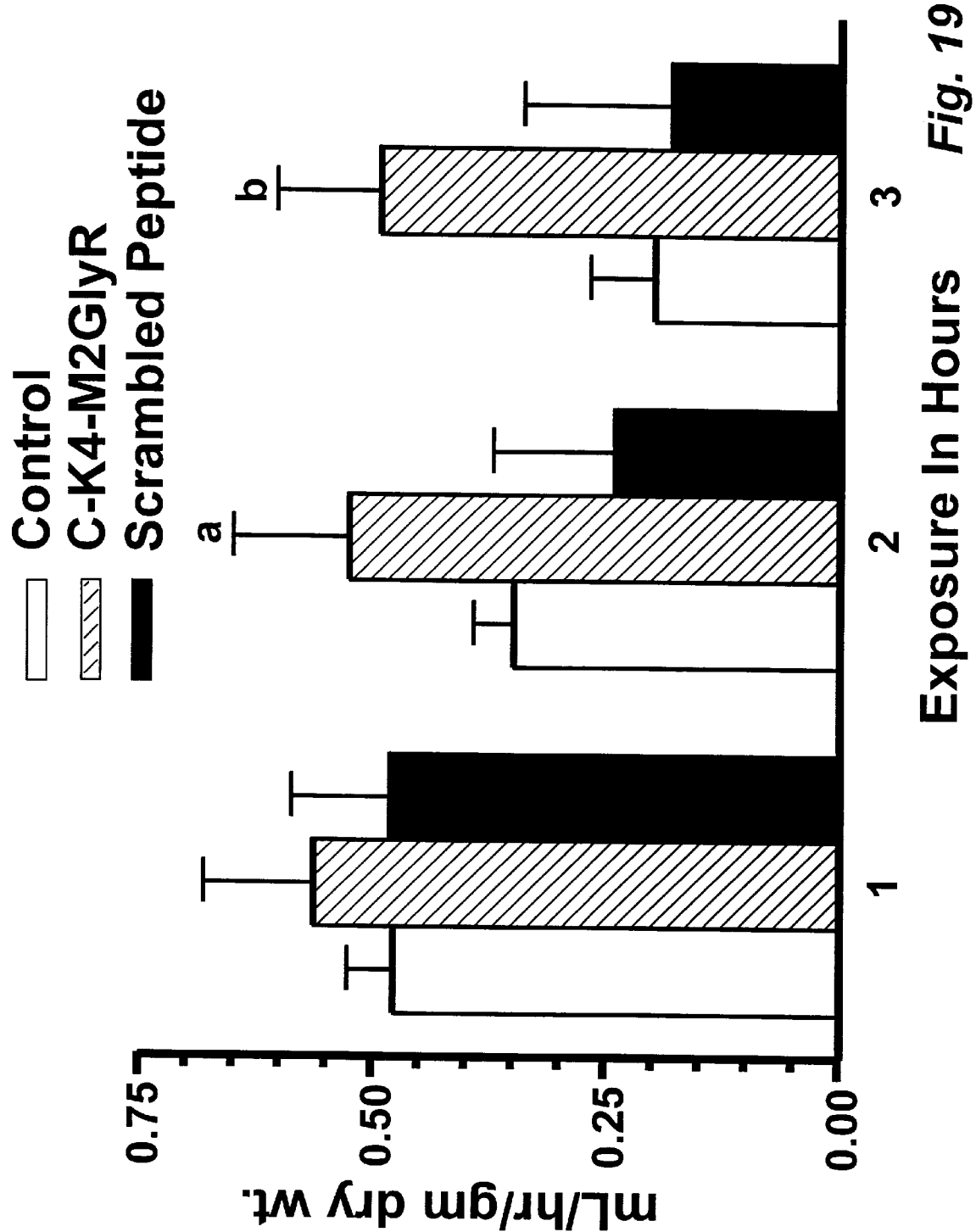
FIG. 19 is a graph illustrating the effect of C-K₄-M2GlyR (SEQ ID NO: 7) and C-K₄-M2GlyR SCRAMBLED (SEQ ID NO: 24) on fluid secretion by rat small intestinal segments, wherein n=4 for each condition, comparison between C-K₄-M2GlyR (SEQ ID NO: 7) and C-K₄-M2GlyR SCRAMBLED (SEQ ID NO: 24) p<0.05, [b] comparison between C-K₄-M2GlyR (SEQ ID NO: 7) and control, p<0.05.

The effect of C-$K_4$-M2GlyR (SEQ ID NO: 7) on fluid transport in rat intestine was tested. The small intestine was removed from a rat that was fasted for 12 hrs. The intestinal contents were flushed out and the intestine was divided into three groups of four segments each approximately 3 cm in length. The first segment of each group served as a control, the second segment contained 200 $\mu$M C-$K_4$-M2GlyR (SEQ ID NO: 7) and the third segment contained 200 $\mu$M of the scrambled peptide. The distal end of each segment was tied and cut free, the segment was filled with 100 $\mu$L of a Ringer's solution containing no organic substrates, and the proximal end was tied. The segments were lightly blotted on filter paper and weighed and then incubated for three one-hour periods in the Ringer's solution at 37° C. The segments were blotted and weighted at the end of each period and the weight change for each period was calculated. At the end of the experiment, the segments were dried at 95° C. for 48 hrs. The results of one such experiment are presented in FIG. 19. Fluid secreted into the segments are expressed as mL/gm dry wt of tissue. The results are not conclusive but they strongly suggest that the peptide is capable of stimulating fluid secretion in this intact epithelium in vitro.

EXAMPLE 15

Method

In this in vivo experiment, BALB/C mice were treated with a 100 $\mu$L bolus, intratracheally, of the N-$K_4$-M2GlyR (SEQ ID NO: 17) peptide dissolved in Ringers solution pH 7.4. For the control sequence, 100 $\mu$L of just the salt solution described above with blue dextran added to match the viscosity of the peptide solution. The boluses were delivered with a 200 $\mu$L blow-through of air through a 20 gauge blunt needle inserted into the trachea of anaesthetized mice. The treated mice received the same bolus volume containing the peptide at a concentration of 2.80 mM.

Results

During the experiment, the anesthetic generally wore off about an hour after treatment. The control mice were soon active and began taking food and drink within two hours of treatment. The treated mice were much slower to recover and took several hours even to turn upright. During recovery, they were warmed using a light positioned over the pen. While the treated animals were sedated, their breathing was labored and somewhat spasmodic. A less labored breathing was seen as the animals awoke. They finally began taking water and drink around the sixth hour. At 24 hours, they were still lethargic although breathing appeared normal.

In all experiments, surviving animals were sacrified at 3, 6 and 24 hours by cervical dislocation and the lung and airways removed and weighed. Those animals that succumbed earlier were necropsied as soon as possible with their lungs and airways removed and weighed, and the heart dissected away. After lungs were weighed, they were suspended in Formalin solution for fixation and delivered to the Histology/Pathology lab for microscopic examination. For the control, the resulting blue lungs were photographed to indicate penetration of blue dextran.

Figure 20A:
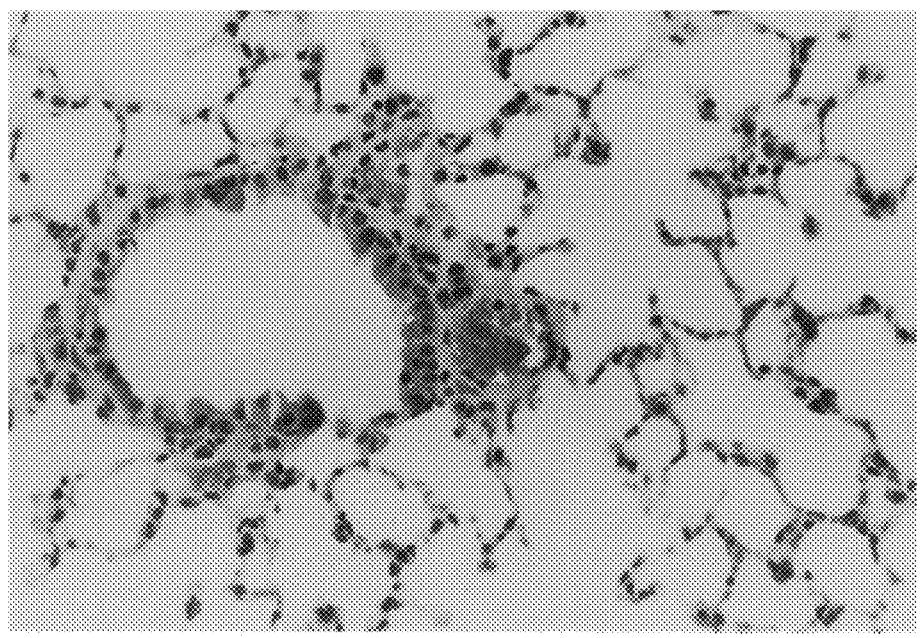
FIG. 20 is a comparative set of photographs derived from the mouse lung tissue studies described in Example 15.
Figure 20B:
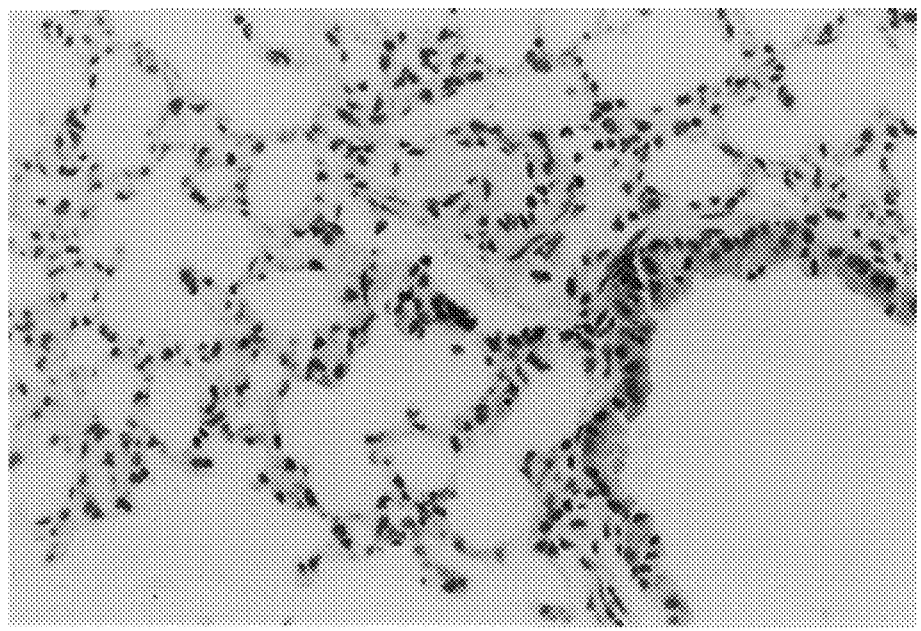

These experiments revealed increased lung weights for all treated mice (n=50 mice). Percent weight increase could be as much as 50%. Histopathology analysis of control and three-hour treated mice is illustrated in FIG. 20. The control photograph depicts a normal lung tissue with alveolar walls normal to slightly thickened in all sections with normal cellularity. Alveolar lumens are normal. Several moderate and large sized airways contain peribronchiolar and peribronchiolar lymphoid aggregates. These aggregatres are small to moderate in size. Similar small lymphoid aggregates are present around rare blood vessels.

The peptide treated photograph depicts alveloar walls that are slightly to moderately thickned throughout the parenchyma. In some areas, there are increased numbers of alveolar macrophages along with rare intralumenal neutrophils. In these areas and surrounding areas, there is sometimes a fine granular to fibrillar eosinophilic material present with alveolar lumens (edema). Large and moderate sized airways are occasionally cuffed by small aggregates of lymphocytes. Epithelium of moderate sized airways often have apical blebbing and a globular material along the mucosal surface. Several prominent pulmonary vessels have thickned amorphous muscular walls. Occasional pulmonary vessels contain slight to moderate perivascular edema. The appearance of the edema in the treated animals confirms that fluid is being fluxed out of the airway epithelium into the airways, and this is the desired phenotype for a cystic fibrosis therapeutic agent.

REFERENCES

The teachings of the following references are herein incorporated by reference:

1. Al-Awqati Q: Regulation of ion channels by ABC transporters that secrete ATP. Science 269: 805–806, 1995.
2. Langosch D, Hartung K, Grell E, Bamberg E, Betz H: Ion channel formation by synthetic transmembrane segments of the inhibitory glycine receptor—a model study. Biochim. Biophys. Acta 1063: 36–44, 1991.
3. Grove A, Iwamoto T, Montal M S, Reddy G L, Marrer S, Tomich J M, Montal M: Towards a unifing structural motif for the pore-forming structure of channel proteins. In: "Biotechnology of Cell Regulation" (Verna R and Nishizuka Y, eds) 4: 89–102, 1992.
4. Garcia-Calvo M, Ruiz-Gomez A, Vazquez J, Morato E, Valdivieso F, Mayor F Jr: Functional reconstitution of the glycine receptor. Biochemistry 28: 6405–6409, 1989.
5. Grenningloh G, Pribilla I, Prior P, Multhaup G, Beyreuther K, Taleb O, Betz H: Cloning and expression of the 58 kd β subunit of the inhibitory glycine receptor. Neuron 4: 963–970, 1990.
6. Grenningloh G, Schmieden V, Schofield P R, Seeburg P H, Siddique T, Mohandas T K, Becker C -M. Betz H: Alpha subunit variants of the human glycine receptor. primary structures, functional expression and chromosomal localization of the corresponding genes. EMBO 9: 771–776, 1990.
7. Schmieie V, Grenningloh G, Schofield P R, Betz H: Functional expression in *Xenopus oocytes* of the strychnine binding 48 kd subunit of the glycine receptor. EMBO 8: 695–700, 1989.
8. Bormann J, Hamill O P, Sakmann B: Mechanism of anion permeation through channels gated by glycine and γ-amino butyric acid in mouse cultured spinal neurones. J. Physiol. (Lond) 385: 243–286, 1987.
9. Twyman R E, MacDonald R L: Kinetic properties of the glycine receptor main- and sub-conductance stages of mouse spinal cord neurones in culture. J. Physiol. (Lond) 435: 303–331, 1991.
10. Reddy G L, Iwamoto T, Tomich J M, Montal M: Synthetic peptides and four-helix bundle proteins as model systems for the pore-forming structure of channel proteins II. Transmembrane segment M2 of the brain glycine receptor is a plausible candidate for the pore-lining structure: J. Biol. Chem. 268: 14608–14615, 1993.
11. Michel H: Crystallization of membrane proteins. Trends Biol. Sci. 8: 56–59, 1983.
12. Dempsey C E: The action of melittin on membranes. Biochim. Biophys. Acta 1031: 143–161, 1990.
13. Boheim G, Hanke W, Jung G: Alamethicin pore formation: voltage dependent flip-flop of alpha-helix dipoles. Biophys. Struct. Mech 9: 181–191, 1987.
14. Menestrin G, Voges K P, Jung G, Boheim G: Voltage-dependent channel formation by rods of helical polypeptides. J. Membr. Biol. 93: 111–113, 1986.
15. Vogel H, Nilsson L, Rigler R, Voges K P, Jung G: Structural fluctuations of a helical polypeptide traversing a lipid bilayer. Proc. Natl. Acad. Sci. U.S.A. 85: 5067–5071, 1988.
16. Millhauser G L: Reptation theory of ion channel gating. Biophys. J. 57: 857–864, 1990.
17. Lauger P: Internal motions in proteins and gating kinetics of ionic channels. Biophys. J. 53: 877–884, 1988.
18. Karle I L, Flippen-Anderson J L, Agarwalla S, Balaram P: Crystal structure of [Leu$^1$] zervamicin, a membrane ion-channel peptide: Implications for gating mechanisms. Proc. Natl. Acad. Sci. USA 88: 5307–5311, 1991.
19. Lee C Y: A possible biological role of the electron transfer between tyrosine and tryptophan-gating of ion channels. FEBS Lett 299: 119–123, 1992.
20. Thiaudiere E, Siffert O, Talbot J C, Bolard J, Alouf J E, Dufourcq J: The amphiphilic alpha-helix concept-consequences on the structure of staphylococcal δ-toxin in solution and bound to lipids. Eur. J. Biochem. 195: 203–213, 1991.
21. Rapaport D, Shai Y: Interaction of fluorescently labeled pardaxin and its analogs with lipid bilayers. J. Biol. Chem. 266: 23769–23775, 1991.
22. Schwarz G, Beschiaschvili G: Thermodynamic and kinetic studies on the association of melittin with a phospholipid bilayer. Biochim. Biophys. Acta 979: 82–90, 1989.
23. Goormaghtigh E, De Meutter J, Szoka F, Cabiaux V, Parente R A, Ruysschaert J M: Secondary structure and orientation of the amphipathic peptide GALA in lipid structures An infrared-spectroscopic approach. Eur. J. Biochem. 195: 421–429, 1991.
24. Molle G, Dugast J Y, Duclohier H, Daumas P, Heitz F, Spach G: Ionophore properties of a synthetic alpha-helical transmembrane fragment of the mitochondrial H$^+$ ATP synthetase of saccharomyces cerevisiae—comparison with alamethicin. Biophys. J. 53: 193–203, 1988.
25. Kennedy D F, Crisma M, Toniolo C, Chapman D: Studies of peptides forming $3_{10}$- and α-helices and β-bend ribbon structures in organic solutions and in model biomembranes by fourier transform infrared spectroscopy. Biochemistry 30: 6541–6548, 1991.
26. Oiki S, Danho W, Madison V, Motal M: M2δ, a candidate for the structure lining ionic channel of the nicotinic cholinergic receptor. Proc. Natl. Acad. Sci. U. S. A. 85: 8703–8707, 1988a.
27. Esposito G, Carver J A, Boyd J, Campbell I D: High-resolution $^1$H NMR study of the solution structure of alamethicin. Biochemistry 26: 1043–1050, 1987.
28. Wade D, Boman A, Wahlin B, Drain C M, Andreu D, Boman H G, Merrifield R B: All D-amino acid-containing channel-forming antibiotic peptides. Proc. Natl. Acad. Sci. U.S.A 87:4761–4765, 1990.
29. Shai Y, Hadari Y R, Finkels A: ph-Dependent pore formation properties of pardaxin analogues. J. Biol. Chem 266: 22346–22354, 1991.
30. Shai Y. Bach D, Yanovsky A: Channel formation properties of synthetic pardaxin and analogs. J. Biol. Chenm 265: 20202–20209, 1990.
31. Oiki S, Danho W, Montal M: Channel protein engineering: synthetic 22-mer peptide from the primary structure of the voltage-sensitive sodium channel forms ionic channels in lipid bilayers. Proc. Natl. Acad. Sci. U.S.A. 85: 2392–2397, 1988b.
32. Schohtz J M, York E J, Stewart J M, Baldwin R L: A neutral, water soluble, alpha-helical peptide: the effect of ionic strength on the helix-coil equilibrium. J. Am. Chem. Soc. 113: 5102–5104, 1991.
33. Wu Y, Huang H W, Olah G A: Method of oriented circular dichroism. Biophys. J. 57: 797–806, 1990.
34. Ludtke S J, He K, Wu Y, Huang H W: Cooperative membrane insertion of magainin correlated with its cytolytic activity. Biochim. Biophys. Acta 1190: 181–184, 1994.
35. Sansom M S P, Kerr I D, Mellor I R: Ion channels formed by amphipathic helical peptides—a molecular modelling study. Eur. J. Biochem. 20, 229–240, 1991.
36. Eisenmen G, Villarroel A, Montal M, Alvarez O: Energy profiles for ion permeation in penameric protein channels: from viruses to receptor channels. In: progress in cell research, edited by Ritchie, J. M., Magistretti, P. J. and Bolis, L. Elsevier Science Publishing: 195–211, 1990.
37. Aqvist J, Warshel A: Energetics of ion permeation through membrane channels—solvation of Na$^+$ by gramicidin A. Biophys. J. 56: 171–182, 1989.
38. Wilcox W, Eisenberg D: Thermodynamics of melittin tetramerization determined by circular dichroism and implications for protein folding. Protein Science 1: 641–653, 1992.
39. Lee K H, Fitton J E, Wuthrich K: Nuclear magnetic resonance investigation of the conformation of delta-haemolysin bound to dodecylphosphocholine micelles. Biochim. Biophys. Acta 91: 144–153, 1987.
40. Zagorski M G, Norman D G, Barrow C J, Iwashita T. Tachibana K, Patel D J: Solution structure of Pardaxin P-2. Biochemistry 30: 8009–8017, 1991.
41. Bechinger B, Kim Y, Chirlian L E, Gesell J, Neumann J M, Montal M, Tomich J M, Zasloff M, Opella S J: Orientation of amphipathic helical peptides in membrane bilayers determined by solid-state NMR spectroscopy. J. Biomolec. NMR 1: 167–173, 1991.
42. Grove A, Tomich J M, Montal M: A molecular blueprint for the pore-forming structure of voltage-gated calcium channels. Proc. Nati. Acad. Sci. USA 88: 6418–6422, 1991.
43. Grove A, Tomich J M, Iwamoto T, Montal M: Design of a functional calcium channel protein: inferences about an ion channel-forming motif derived from the primary structure of voltage-gated calcium channels. Protein Sci. 2: 1918–1930, 1993.

44. Montal M, Montal M S, Tomich I M: Synporins N—synthetic proteins that emulate the pore structure of biological ionic channels. Proc. Natl. Acad. Sci. USA 87: 6929–6933, 1990.

45. Iwamoto T, Grove A, Montal M S, Montal M, Tomich J M: Chemical synthesis and characterization of peptides and oligomeric proteins designed to form transmembrane ion channels. Int. J. Pept. Protein Res. 43: 597–607, 1994.

46. Montal M S, Buehler L, Iwamoto T, Tomich J M, Montal M: Synthetic peptides and four-helix bundle proteins as model systems for the pore-forming structure of channel proteins: I transmembrane segment M2 of the nicotinic cholinergic receptor channel is a key pore-lining structure. J. Biol. Chem. 268: 14601–14607, 1993.

47. Grove A, Tomich J M, Iwamoto T, Montal M: *Drugs in Development Proc.* of Santa Fe Nimodipine Symposium Vol.2 (Scriabine, A. Ed.) Neva Press: (in press), 1994.

48. Eisenberg D: Three-dimensional structure of membrane and surface proteins. Annu. Rev. Biochem. 53: 594–616, 1984.

49. Kersh G J, Tomich J M, Montal M: The M2δ transmembrane domain of the nicotinic cholinergic receptor forms ion channels in human erythrocyte membranes. Biochem. Biophys. Res. Comm. 162: 352–356, 1989.

50. Ye M, Grantham J J: The secretion of fluid by renal cysts from patients with autosomal dominant polycystic kidney disease. N. Engl. J. Med. 329: 310–313, 1993.

51. Grantham J J, Ye M, Gattone V H II, Sullivan L P: In vitro fluid secretion by epithelium from polycystic kidneys. J. Clin. Invest. 95: 195–202, 1995.

52. Mangoo-Karim R, Ye M, Wallace D P, Grantham J J, Sullivan L P: Anion secretion drives fluid secretion by monolayers of cultured human polycystic cells. Am. J. Physiol. 269: F381–F388, 1995.

53. Wallace D P, Grantham J J, Sullivan L P: Chloride and fluid secretion by cultured human polycystic kidney cells. (submitted).

54. Sullivan L P, Wallace D P, Grantham J J: Coupling of cell volume and membrane potential changes to fluid secretion in a model of renal cysts. Kidney InL 45: 1369–1380, 1994.

55. Ross K E, Ye M, Grantham J J, Caplan M J: Immunolocalization of ion transport proteins in human polycystic kidney epithelial cells. (abstract) J. Am. Soc. Nephrol. 5: 634, 1994.

56. Hanaoka K, Schwiebert E M, Wilson P D, Guggino W B: cAMP-activated chloride conductance in autosomal dominant polycystic kidney disease (APKD) cells in primary culture. (abstract) J. Am. Soc. Nephrol. 5: 286, 1994.

57. Davidow C J, Maser R L, Rome L A, Calvet J P, Grantham J J: The cystic fibrosis transmembrane conductance regulator (CFTR) mediates transepithelial chloride and fluid secretion by human autosomal dominant polycystic kidney disease (APKD) epithelium in vitro. (submitted).

58. Macias W L, McAteer J A, Tanner G A, Fritz A L, Armstrong W M: NaCl transport by Madin Darby canine kidney cyst epithelial cells. Kidney Int. 42: 308–319, 1992.

59. Brown A R, Pickrell J A: Chamber for testing metered-dose propellant-driven aerosols of immunologically relevant proteins. J. Immunol. Methods 176: 203–212, 1994.

60. Brown A R, Slusser J G: Propellant-driven aerosols of functional proteins as potential therapeutic agents in the respiratory tract. Immunopharnacology 28: 241–257, 1994.

61. Brown A R, Pickrell J A: Propellant-driven aerosols for delivery of proteins in the respiratory tract. J. Aerosol Med. 8: 43–58, 1995.

62. Grant M E, Neufeld T K, Cargoe E J Jr, Welling L W, Grantham J J: Arginine vasopressin stimulates net fluid secretion in a polarized subculture of cyst-forming MDCK cells. J. Am. Soc. Nephrol. 2: 219–227, 1991.

63. Venglarik C J, Bridges R J, Frizzel R A: A simple assay for agonist-regulated Cl and K conductances in salt-secreting epithelial cells. Am. J. Physiol. 259: C358–C364, 1990.

64. Biwersi J, Verkman A S: Cell-permeable fluorescent indicator for cytosolic chloride. Biochem. 30: 7879–7883, 1991.

65. Bell D, McDermott B J: Use of the cyclic AMP antagonist, Rp-cAMPS, to distinguish between cyclic AMP-dependent and cyclic AMP-independent contractile response in rat ventricular cardiomyocytes. J. Mol. Cell Cardiol. 26: 1439–1448, 1994.

66. Garvin J L, Spring K R: Regulation of apical membrane ion transport in Necturus gallbladder. Am. J. Physiol. 263: C187–C193, 1992.

67. Engelebretsen, D R, Alewood, P F: Boc SPPS of two hydrophobic peptides using a "solubilizing Tail" strategy: dodecaalanine and chemotactic protein $10^{42-55}$. Tetrahedron Letts. 37:8431–34.

68. El-Etri, M., and J. Cuppoletti. Metalloporphyrin chloride ionophores: induction of increased anion permeability in lung epithelial cells. Am. J Physiol. 270: L386–L392, 1996.

69. Grantham, J. J., M. Uchic, E. J. Cragoe, Jr., J. Komnhaus, J. A. Grantham, V. Donoso, R. Mangoo-Karim, A. Evan, and J. McAteer. Chemical modification of cell proliferation and fluid secretion in renal cysts. *Kidney Int.* 35:1379–1389, 1989.

70. Krishna, A., and P. F. Terranova. Relationships between LH stimulation in vitro and progesterone, androstenedione and cyclic AMP synthesis in preantral follicles of the cyclic hamster. *J. Endocr*. 114: 55–63, 1987.

71. Liedtke, C. M. Regulation of chloride transport in epithelia. *Annu. Rev. Physiol*. 51: 143–160, 1989.

72. Neufeld, T. K., M. E. Grant, and J. J. Grantham. A method to measure the rate of net fluid secretion by monolayers of cultured renal epithelial cells. *J. Tiss. cult. Meth*. 13: 229–234, 1991.

73. Reeves, W. B., and T. E. Andreoli. Renal epithelial chloride channels. *Annu. Rev. Physiol.* 54: 29–50, 1992.

74. Simmons, N. L. Renal epithelial $Cl^-$ secretion. *Exp Physiol*: 78, 117–137, 1993.

We claim:

1. A peptide selected from the group consisting of SEQ ID NOS: 7–21.

2. The peptide of claim 1, said sequence being SEQ ID NO: 7.

3. A peptide being a segment of a native channel protein, said peptide being soluble in water to a level of at least 10 mM, said peptide having at least one end thereof modified with the addition of polar amino acid residues to alter the net charge thereof and improve its solubility, and said peptide being selected from the group consisting of SEQ ID NOS: 7–21.

4. A method of altering the flux of water across an epithelial cell presenting first and second spaced apart surfaces, said method comprising the steps of:

providing from 3–6 peptides capable of forming a channel assembly for transport of anions through said epithelial cell, each of said peptides being selected from the group consisting of SEQ ID NOS: 7–9 and 17 and contacting said peptides with said first surface of said epithelial cell, and causing said peptides to alter the flux of water across said cell surface.

* * * * *

UNITED STATES PATENT AND TRADEMARK OFFICE
CERTIFICATE OF CORRECTION

PATENT NO. : 6,077,826
DATED : June 20, 2000
INVENTOR(S) : John M. Tomich, Takeo Iwamoto, Lawrence P. Sullivan It is certified that error appears in the above-identified patent and that said Letters Patent is hereby corrected as shown below:

[63] Please insert after the word "abandoned" the following:

-- which claims benefit from the Provisional Patent Application Serial No. 60/045,790, filed January 25, 1996, which was converted from a non-provisional application, S/N 08/591,381, filed January 25, 1996, now abandoned, the teachings of which are incorporated herein by reference. --

Signed and Sealed this

Twenty-eighth Day of August, 2001

Attest:

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
       (A) LENGTH: 23 amino acids
       (B) TYPE: amino acid
       (C) STRANDEDNESS:
       (D) TOPOLOGY: linear (ii) MOLECULE TYPE: peptide (iii) HYPOTHETICAL: NO (v) FRAGMENT TYPE: internal (vi) ORIGINAL SOURCE:
       (F) TISSUE TYPE: Brain (xi) SEQUENCE DESCRIPTION: SEQ ID NO:1:

```
Pro Ala Arg Val Gly Leu Gly Ile Thr Thr Val Leu Thr Met Thr Thr
1               5                   10                  15

Gln Ser Ser Gly Ser Arg Ala
            20
```

(2) INFORMATION FOR SEQ ID NO:2:

(i) SEQUENCE CHARACTERISTICS:
       (A) LENGTH: 23 amino acids
       (B) TYPE: amino acid
       (C) STRANDEDNESS:
       (D) TOPOLOGY: linear (ii) MOLECULE TYPE: peptide (iii) HYPOTHETICAL: NO (v) FRAGMENT TYPE: internal (vi) ORIGINAL SOURCE:
       (F) TISSUE TYPE: Brain (xi) SEQUENCE DESCRIPTION: SEQ ID NO:2:

```
Pro Ala Arg Thr Val Phe Gly Val Thr Thr Val Leu Thr Met Thr Thr
1               5                   10                  15

Leu Ser Ile Ser Ala Arg Asn
            20
```

(2) INFORMATION FOR SEQ ID NO:3:

(i) SEQUENCE CHARACTERISTICS:
       (A) LENGTH: 22 amino acids
       (B) TYPE: amino acid
       (C) STRANDEDNESS:
       (D) TOPOLOGY: linear (ii) MOLECULE TYPE: peptide (iii) HYPOTHETICAL: NO (v) FRAGMENT TYPE: internal (vi) ORIGINAL SOURCE:
       (F) TISSUE TYPE: Epithelium (xi) SEQUENCE DESCRIPTION: SEQ ID NO:3:

-continued

```
Arg Ser Ile Ala Ile Tyr Leu Gly Ile Gly Leu Cys Leu Leu Phe Ile
1               5                   10                  15

Val Arg Thr Leu Leu Leu
            20
```

(2) INFORMATION FOR SEQ ID NO:4:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (vi) ORIGINAL SOURCE:
        (F) TISSUE TYPE: Epithelium (xi) SEQUENCE DESCRIPTION: SEQ ID NO:4:

```
Lys Gly Ile Ile Leu Arg Lys Ile Phe Thr Thr Ile Ser Phe Cys Ile
1               5                   10                  15

Val Leu Arg Met Ala Val
            20
```

(2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (vi) ORIGINAL SOURCE:
        (F) TISSUE TYPE: Epithelium (xi) SEQUENCE DESCRIPTION: SEQ ID NO:5:

```
Tyr Ile Phe Val Ala Thr Val Pro Val Ile Val Ala Phe Ile Met Leu
1               5                   10                  15

Arg Ala Tyr Phe Leu Gln
            20
```

(2) INFORMATION FOR SEQ ID NO:6:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (vi) ORIGINAL SOURCE:
        (F) TISSUE TYPE: Epithelium (xi) SEQUENCE DESCRIPTION: SEQ ID NO:6:

```
Arg Val Gly Ile Ile Leu Thr Leu Ala Met Asn Ile Met Ser Thr Leu
1               5                   10                  15

Gln Trp Ala Val Asn Ser Ile
            20
```

(2) INFORMATION FOR SEQ ID NO:7:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (vi) ORIGINAL SOURCE:
        (F) TISSUE TYPE: Brain (xi) SEQUENCE DESCRIPTION: SEQ ID NO:7:

```
Pro Ala Arg Val Gly Leu Gly Ile Thr Thr Val Leu Thr Met Thr Thr
1               5                   10                  15

Gln Ser Ser Gly Ser Arg Ala Lys Lys Lys Lys
            20                  25
```

(2) INFORMATION FOR SEQ ID NO:8:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (vi) ORIGINAL SOURCE:
        (F) TISSUE TYPE: Brain (ix) FEATURE:
        (A) NAME/KEY: Modified-site
        (B) LOCATION: 1
        (D) OTHER INFORMATION: /note= "N-terminus is capped with
           Acetyl group, and C-terminus is capped with Amide group."

(xi) SEQUENCE DESCRIPTION: SEQ ID NO:8:

```
Pro Ala Arg Val Gly Leu Gly Ile Thr Thr Val Leu Thr Cys Thr Thr
1               5                   10                  15

Gln Ser Ser Gly Ser Arg Ala
            20
```

(2) INFORMATION FOR SEQ ID NO:9:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (iii) HYPOTHETICAL: YES (v) FRAGMENT TYPE: internal

```
        (vi) ORIGINAL SOURCE:
              (F) TISSUE TYPE: Brain (ix) FEATURE:
              (A) NAME/KEY: Modified-site
              (B) LOCATION: 1
              (D) OTHER INFORMATION: /note= "N-terminus is capped with
                  Acetyl group, and C-terminus is capped with Amide group."

(xi) SEQUENCE DESCRIPTION: SEQ ID NO:9:

Pro Ala Arg Val Gly Leu Gly Ile Thr Thr Val Leu Thr Pro Thr Thr
1               5                  10                  15

Gln Ser Ser Gly Ser Arg Ala
            20

(2) INFORMATION FOR SEQ ID NO:10:

(i) SEQUENCE CHARACTERISTICS:
              (A) LENGTH: 23 amino acids
              (B) TYPE: amino acid
              (C) STRANDEDNESS:
              (D) TOPOLOGY: linear (ii) MOLECULE TYPE: peptide (iii) HYPOTHETICAL: NO (v) FRAGMENT TYPE: internal (vi) ORIGINAL SOURCE:
              (F) TISSUE TYPE: Brain (ix) FEATURE:
              (A) NAME/KEY: Modified-site
              (B) LOCATION: 1
              (D) OTHER INFORMATION: /note= "N-terminus is capped with
                  Acetyl Group."

(xi) SEQUENCE DESCRIPTION: SEQ ID NO:10:

Pro Ala Arg Val Gly Leu Gly Ile Thr Thr Val Leu Thr Met Thr Thr
1               5                  10                  15

Gln Ser Ser Gly Ser Arg Ala
            20

(2) INFORMATION FOR SEQ ID NO:11:

(i) SEQUENCE CHARACTERISTICS:
              (A) LENGTH: 24 amino acids
              (B) TYPE: amino acid
              (C) STRANDEDNESS:
              (D) TOPOLOGY: linear (ii) MOLECULE TYPE: peptide (iii) HYPOTHETICAL: NO (v) FRAGMENT TYPE: internal (vi) ORIGINAL SOURCE:
              (F) TISSUE TYPE: Brain (ix) FEATURE:
              (A) NAME/KEY: Modified-site
              (B) LOCATION: 1
              (D) OTHER INFORMATION: /note= "N-terminus is capped with
                  Acetyl group.  Xaa at position 1 represents
                  diaminopropionic acid (DAP)."

(xi) SEQUENCE DESCRIPTION: SEQ ID NO:11:

Xaa Pro Ala Arg Val Gly Leu Gly Ile Thr Thr Val Leu Thr Met Thr
1               5                  10                  15
```

Thr Gln Ser Ser Gly Ser Arg Ala
            20

(2) INFORMATION FOR SEQ ID NO:12:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (vi) ORIGINAL SOURCE:
        (F) TISSUE TYPE: Brain (ix) FEATURE:
        (A) NAME/KEY: Modified-site
        (B) LOCATION: 1
        (D) OTHER INFORMATION: /note= "Xaa at position 1
            represents diaminopropionic acid (DAP)."

(xi) SEQUENCE DESCRIPTION: SEQ ID NO:12:

Xaa Pro Ala Arg Val Gly Leu Gly Ile Thr Thr Val Leu Thr Met Thr
1               5                   10                  15

Thr Gln Ser Ser Gly Ser Arg Ala
            20

(2) INFORMATION FOR SEQ ID NO:13:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (vi) ORIGINAL SOURCE:
        (F) TISSUE TYPE: Brain (ix) FEATURE:
        (A) NAME/KEY: Modified-site
        (B) LOCATION: 2
        (D) OTHER INFORMATION: /note= "Xaa at position 2
            represents diaminopropionic acid (DAP)."

(xi) SEQUENCE DESCRIPTION: SEQ ID NO:13:

Lys Xaa Pro Ala Arg Val Gly Leu Gly Ile Thr Thr Val Leu Thr Met
1               5                   10                  15

Thr Thr Gln Ser Ser Gly Ser Arg Ala
            20                  25

(2) INFORMATION FOR SEQ ID NO:14:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (vi) ORIGINAL SOURCE:
            (F) TISSUE TYPE: Brain (xi) SEQUENCE DESCRIPTION: SEQ ID NO:14:

Lys Pro Ala Arg Val Gly Leu Gly Ile Thr Thr Val Leu Thr Met Thr
1               5                  10                  15

Thr Gln Ser Ser Gly Ser Arg Ala
            20

(2) INFORMATION FOR SEQ ID NO:15:

(i) SEQUENCE CHARACTERISTICS:
            (A) LENGTH: 25 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (vi) ORIGINAL SOURCE:
            (F) TISSUE TYPE: Brain (xi) SEQUENCE DESCRIPTION: SEQ ID NO:15:

Lys Lys Pro Ala Arg Val Gly Leu Gly Ile Thr Thr Val Leu Thr Met
1               5                  10                  15

Thr Thr Gln Ser Ser Gly Ser Arg Ala
            20                  25

(2) INFORMATION FOR SEQ ID NO:16:

(i) SEQUENCE CHARACTERISTICS:
            (A) LENGTH: 26 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (vi) ORIGINAL SOURCE:
            (F) TISSUE TYPE: Brain (xi) SEQUENCE DESCRIPTION: SEQ ID NO:16:

Lys Lys Lys Pro Ala Arg Val Gly Leu Gly Ile Thr Thr Val Leu Thr
1               5                  10                  15

Met Thr Thr Gln Ser Ser Gly Ser Arg Ala
            20                  25

(2) INFORMATION FOR SEQ ID NO:17:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (vi) ORIGINAL SOURCE:
            (F) TISSUE TYPE: Brain (xi) SEQUENCE DESCRIPTION: SEQ ID NO:17:

Lys Lys Lys Lys Pro Ala Arg Val Gly Leu Gly Ile Thr Thr Val Leu
1               5                   10                  15

Thr Met Thr Thr Gln Ser Ser Gly Ser Arg Ala
            20                  25

(2) INFORMATION FOR SEQ ID NO:18:

(i) SEQUENCE CHARACTERISTICS:
            (A) LENGTH: 28 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (vi) ORIGINAL SOURCE:
            (F) TISSUE TYPE: Brain (xi) SEQUENCE DESCRIPTION: SEQ ID NO:18:

Lys Lys Lys Lys Lys Pro Ala Arg Val Gly Leu Gly Ile Thr Thr Val
1               5                   10                  15

Leu Thr Met Thr Thr Gln Ser Ser Gly Ser Arg Ala
            20                  25

(2) INFORMATION FOR SEQ ID NO:19:

(i) SEQUENCE CHARACTERISTICS:
            (A) LENGTH: 29 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (vi) ORIGINAL SOURCE:
            (F) TISSUE TYPE: Brain (xi) SEQUENCE DESCRIPTION: SEQ ID NO:19:

Lys Lys Lys Lys Lys Lys Pro Ala Arg Val Gly Leu Gly Ile Thr Thr
1               5                   10                  15

Val Leu Thr Met Thr Thr Gln Ser Ser Gly Ser Arg Ala
            20                  25

(2) INFORMATION FOR SEQ ID NO:20:

(i) SEQUENCE CHARACTERISTICS:
            (A) LENGTH: 26 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (vi) ORIGINAL SOURCE:
             (F) TISSUE TYPE: Brain (xi) SEQUENCE DESCRIPTION: SEQ ID NO:20:

Pro Ala Arg Val Gly Leu Gly Ile Thr Thr Val Leu Thr Met Thr Thr
1               5                   10                  15
Gln Ser Ser Gly Ser Arg Ala Lys Lys Lys
            20                  25

(2) INFORMATION FOR SEQ ID NO:21:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (vi) ORIGINAL SOURCE:
            (F) TISSUE TYPE: Brain (ix) FEATURE:
            (A) NAME/KEY: Modified-site
            (B) LOCATION: 27
            (D) OTHER INFORMATION: /note= "C-terminus is capped with
                Amide group."

(xi) SEQUENCE DESCRIPTION: SEQ ID NO:21:

Pro Ala Arg Val Gly Leu Gly Ile Thr Thr Val Leu Thr Met Thr Thr
1               5                   10                  15
Gln Ser Ser Gly Ser Arg Ala Lys Lys Lys Lys
            20                  25

(2) INFORMATION FOR SEQ ID NO:22:

(i) SEQUENCE CHARACTERISTICS:
            (A) LENGTH: 23 amino acids
            (B) TYPE: amino acid
            (C) STRANDEDNESS:
            (D) TOPOLOGY: linear (ii) MOLECULE TYPE: peptide (iii) HYPOTHETICAL: NO (vi) ORIGINAL SOURCE:
            (F) TISSUE TYPE: Brain (xi) SEQUENCE DESCRIPTION: SEQ ID NO:22:

Ser Leu Thr Val Thr Ala Arg Gln Arg Val Thr Pro Ser Leu Ser Ile
1               5                   10                  15
Thr Ala Met Gly Thr Gly Gly
            20

(2) INFORMATION FOR SEQ ID NO:23:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide

```
        (iii) HYPOTHETICAL: NO (vi) ORIGINAL SOURCE:
             (F) TISSUE TYPE: Brain (xi) SEQUENCE DESCRIPTION: SEQ ID NO:23:

Lys Lys Lys Lys Ser Leu Thr Val Thr Ala Arg Gln Arg Val Thr Pro
1               5                  10                 15

Ser Leu Ser Ile Thr Ala Met Gly Thr Gly Gly
            20                  25

(2) INFORMATION FOR SEQ ID NO:24:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (iii) HYPOTHETICAL: NO (vi) ORIGINAL SOURCE:
             (F) TISSUE TYPE: Brain (xi) SEQUENCE DESCRIPTION: SEQ ID NO:24:

Ile Leu Ala Ser Thr Arg Ser Gln Thr Gly Arg Met Ala Leu Ser Gly
1               5                  10                 15

Thr Thr Thr Pro Gly Val Val Lys Lys Lys Lys
            20                  25

(2) INFORMATION FOR SEQ ID NO:25:

(i) SEQUENCE CHARACTERISTICS:
            (A) LENGTH: 24 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (vi) ORIGINAL SOURCE:
             (F) TISSUE TYPE: Lung (xi) SEQUENCE DESCRIPTION: SEQ ID NO:25:

Arg Phe Met Phe Tyr Gly Ile Phe Leu Tyr Leu Gly Glu Val Thr Lys
1               5                  10                 15

Ala Val Gln Pro Leu Leu Leu Gly
            20

(2) INFORMATION FOR SEQ ID NO:26:

(i) SEQUENCE CHARACTERISTICS:
            (A) LENGTH: 25 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal
```

(vi) ORIGINAL SOURCE:
              (F) TISSUE TYPE: Lung (xi) SEQUENCE DESCRIPTION: SEQ ID NO:26:

Lys Arg Phe Met Phe Tyr Gly Ile Phe Leu Tyr Leu Gly Glu Val Thr
1               5                   10                  15

Lys Ala Val Gln Pro Leu Leu Leu Gly
            20                  25

(2) INFORMATION FOR SEQ ID NO:27:

(i) SEQUENCE CHARACTERISTICS:
              (A) LENGTH: 26 amino acids
              (B) TYPE: amino acid
              (C) STRANDEDNESS:
              (D) TOPOLOGY: linear (ii) MOLECULE TYPE: peptide (iii) HYPOTHETICAL: NO (v) FRAGMENT TYPE: internal (vi) ORIGINAL SOURCE:
              (F) TISSUE TYPE: Lung (xi) SEQUENCE DESCRIPTION: SEQ ID NO:27:

Lys Lys Arg Phe Met Phe Tyr Gly Ile Phe Leu Tyr Leu Gly Glu Val
1               5                   10                  15

Thr Lys Ala Val Gln Pro Leu Leu Leu Gly
            20                  25

(2) INFORMATION FOR SEQ ID NO:28:

(i) SEQUENCE CHARACTERISTICS:
              (A) LENGTH: 27 amino acids
              (B) TYPE: amino acid
              (C) STRANDEDNESS:
              (D) TOPOLOGY: linear (ii) MOLECULE TYPE: peptide (iii) HYPOTHETICAL: NO (v) FRAGMENT TYPE: internal (vi) ORIGINAL SOURCE:
              (F) TISSUE TYPE: Lung (xi) SEQUENCE DESCRIPTION: SEQ ID NO:28:

Lys Lys Lys Arg Phe Met Phe Tyr Gly Ile Phe Leu Tyr Leu Gly Glu
1               5                   10                  15

Val Thr Lys Ala Val Gln Pro Leu Leu Leu Gly
            20                  25

(2) INFORMATION FOR SEQ ID NO:29:

(i) SEQUENCE CHARACTERISTICS:
              (A) LENGTH: 28 amino acids
              (B) TYPE: amino acid
              (C) STRANDEDNESS:
              (D) TOPOLOGY: linear (ii) MOLECULE TYPE: peptide (iii) HYPOTHETICAL: NO (v) FRAGMENT TYPE: internal

```
        (vi) ORIGINAL SOURCE:
              (F) TISSUE TYPE: Lung (xi) SEQUENCE DESCRIPTION: SEQ ID NO:29:

Lys Lys Lys Lys Arg Phe Met Phe Tyr Gly Ile Phe Leu Tyr Leu Gly
1               5                   10                  15

Glu Val Thr Lys Ala Val Gln Pro Leu Leu Leu Gly
            20                  25

(2) INFORMATION FOR SEQ ID NO:30:

(i) SEQUENCE CHARACTERISTICS:
              (A) LENGTH: 29 amino acids
              (B) TYPE: amino acid
              (C) STRANDEDNESS:
              (D) TOPOLOGY: linear (ii) MOLECULE TYPE: peptide (iii) HYPOTHETICAL: NO (v) FRAGMENT TYPE: internal (vi) ORIGINAL SOURCE:
              (F) TISSUE TYPE: Lung (xi) SEQUENCE DESCRIPTION: SEQ ID NO:30:

Lys Lys Lys Lys Lys Arg Phe Met Phe Tyr Gly Ile Phe Leu Tyr Leu
1               5                   10                  15

Gly Glu Val Thr Lys Ala Val Gln Pro Leu Leu Leu Gly
                20                  25

(2) INFORMATION FOR SEQ ID NO:31:

(i) SEQUENCE CHARACTERISTICS:
              (A) LENGTH: 30 amino acids
              (B) TYPE: amino acid
              (C) STRANDEDNESS:
              (D) TOPOLOGY: linear (ii) MOLECULE TYPE: peptide (iii) HYPOTHETICAL: NO (v) FRAGMENT TYPE: internal (vi) ORIGINAL SOURCE:
              (F) TISSUE TYPE: Lung (xi) SEQUENCE DESCRIPTION: SEQ ID NO:31:

Lys Lys Lys Lys Lys Lys Arg Phe Met Phe Tyr Gly Ile Phe Leu Tyr
1               5                   10                  15

Leu Gly Glu Val Thr Lys Ala Val Gln Pro Leu Leu Leu Gly
                20                  25              30
```